United States Patent
Skadhauge et al.

(10) Patent No.: US 12,185,681 B2
(45) Date of Patent: Jan. 7, 2025

(54) METHODS FOR PREPARING MUTANT PLANTS

(71) Applicant: Carlsberg A/S, Copenhagen V (DK)

(72) Inventors: Birgitte Skadhauge, Copenhagen V (DK); Soren Knudsen, Copenhagen V (DK); Gustav Hambraeus, Copenhagen V (DK); Toni Wendt, Copenhagen V (DK); Magnus Rasmussen, Copenhagen V (DK); Jeppe Thulin Østerberg, Copenhagen V (DK); Ross Fennessy, Copenhagen V (DK)

(73) Assignee: Carlsberg A/S, Copenhagen V (DK)

( * ) Notice: Subject to any disclaimer, the term of this patent is extended or adjusted under 35 U.S.C. 154(b) by 0 days.

(21) Appl. No.: 17/715,723

(22) Filed: Apr. 7, 2022

(65) Prior Publication Data
US 2022/0312707 A1 Oct. 6, 2022

Related U.S. Application Data

(63) Continuation-in-part of application No. PCT/EP2020/078321, filed on Oct. 8, 2020.

(51) Int. Cl.
| | | |
|---|---|---|
| *A01H 1/04* | (2006.01) | |
| *A01H 1/02* | (2006.01) | |
| *A01H 6/46* | (2018.01) | |
| *C12N 15/10* | (2006.01) | |

(52) U.S. Cl.
CPC .............. *A01H 1/04* (2013.01); *A01H 1/026* (2021.01); *A01H 6/46* (2018.05); *C12N 15/1034* (2013.01)

(58) Field of Classification Search
None
See application file for complete search history.

(56) References Cited

U.S. PATENT DOCUMENTS

| | | |
|---|---|---|
| 6,326,145 B1 | 12/2001 | Whitcombe et al. |
| 7,622,280 B2 | 11/2009 | Holliger et al. |
| 7,838,053 B2 | 11/2010 | Breddam et al. |

FOREIGN PATENT DOCUMENTS

| | | |
|---|---|---|
| WO | 2001075167 A1 | 10/2001 |
| WO | 2009041810 A1 | 4/2009 |
| WO | 2010036352 A1 | 4/2010 |
| WO | 2018001884 A1 | 1/2018 |
| WO | 2019136518 A1 | 7/2019 |

OTHER PUBLICATIONS

Glowacka et al. Plant, Cell and Environment (2016), 39:908-917.*
Yang et al. Nature (2015), 523, p. 463-467.*
Uauy et al. Annu. Rev. Genet (2017) 51:435-454.*
Lee, G., et al., "Identification of Mutagenized Plant Populations," Current Technologies in Plant Molecular Breeding, chapter 7, pp. 205-239 (2015).
Bovina, et al., "Discovery of chemically induced mutations by TILLING," Plant mutation breeding and biotechnioology, pp. 257-268 (2012).
Broccanello, et al., "Comparison of three PCR-based assays for SNP genotyping in plants," Plants Methods, vol. 14, No. 28, pp. 1-8 (2018).
Chen, et al., "CRISPR-Cas12a target binding unleashes indiscriminate single-stranded DNAse activity," Science, vol. 27, pp. 436-439 (2018).
Chen, et al., "Development and characterization of a New TILLING Population of Common bread wheat," Plos One, vol. 7, No. 7, pp. 1-11 (2012).
Chi, et al., "Discovery of rare mutations in extensively pooled DNA samples using multiple target enrichment," Plant Biotechnology Journal, vol. 12, pp. 709-717 (2014).
Dobosy, et al., "RNase H-dependent PCR (rhPCR): improved specificity and single nucleotide polymorphism detection using blocked cleavable primers," BMC Biotechnology, vol. 11, No. 80, pp. 1-18 (2011).
Emrani, et al., "Reduction in sinapine content in rapeseed (*Brassica napus* L.) by induced mutations in sinapine biosyntheis genes," Molecular Breeding, vol. 35, No. 37, pp. 1-11 (2015).
Hein, et al., "Functional Validation in the Triticeae," Plant Genetics and Genomics, pp. 359-385 (2009).
Hindson, et al., "High-throughput droplet digital PCR system for absolute quantitation of DNA copy number," Analytical Chemistry, vol. 83, pp. 8604-8610 (2011).
Kleinhofs, et al., "Induction and selection of specific gene mutations in Hordeum and Pisum", Mutation Research, vol. 51, pp. 29-35 (1978).
Koornneef, "Classical mutagenesis in higher plants," Molecular Plant Biology, pp. 1-12 (2002).
Kurowska, et al., "TILLING: a shortcut in functional genomics," Journal of Applied Genetics, vol. 52, pp. 371-390 (2011).
Lu, et al., "Genome-wide Targeted Mutagenesis in Rice Using the CRISPR/Cas9 system," Molecular Plant, vol. 10, No. 9, pp. 1242-1245 (2017).
Szarejko, et al., "Creation of TILLING population in Barley after chemical mutagenesis with Sodium Azide and MNU," International Atomic Energy Agency, pp. 91-111 (2017).
Szurman-Zubrzycka, et al., "HorTILLUS—A Rich and Renewable Source of Induced Mutations for Forward/Reverse Genetics and Pre-breeding Programs in Barley (*Hordeum vulgare* L.)," Frontiers in Plant Science, vol. 9, No. 216, pp. 1-16 (2018).
Tiessen, et al., "Mathematical modeling and comparison of protein size distribution in different plant, animal, fungal and microbial species reveals a negative correlation between protein size and protein No., thus providing insight into the evolution of proteomes," BMC Research Notes, pp. 1-23 (2012).

(Continued)

*Primary Examiner* — Medina A Ibrahim
(74) *Attorney, Agent, or Firm* — McNeill PLLC

(57) ABSTRACT

The present invention provides methods of preparing plants, with specific predetermined mutation(s) in one or more NOI(s). The specific predetermined mutation(s) preferably may result in the identification of plants having desired traits.

18 Claims, 3 Drawing Sheets

Specification includes a Sequence Listing.

(56) References Cited

OTHER PUBLICATIONS

Tsai, et al., "Discovery of Rare Mutations in Populations: TILLING by Sequencing," Plant Physiology, vol. 156, No. 3, pp. 1257-1268 (2011).

Tsai, et al., "Production of a high-efficiency TILLING population through polyploidization," Plant Physiology, vol. 161, pp. 1604-1614 (2013).

Xu, et al., "Whole-genome strategies for marker-assisted plant breeding," Molecular Breeding, vol. 29, pp. 833-854 (2012).

Cousin, S., et al., "Draft genome sequence of Lactobacillus pasteurii CRBIP 24.76T," Genome Announcements, vol. 1, No. 4, p. e0060-13 (2013).

Nazarenko, I., et al., "A closed tube format for amplification and detection of DNA based on energy transfer," Nucleic Acids Research, vol. 25, No. 12, pp. 2516-2521 (1997).

Redei, G., et al., "Classical Mutagenesis," Methods in Arabidopsis Research, chapter 2, pp. 16-82 (1992).

Tyagi, S., et al., "Multicolor molecular beacons for allele discrimination," Nature Biotechnology, vol. 16, pp. 49-53 (1998).

Copending U.S. Appl. No. 18/536,784, of Toni Wendt et al., filed Dec. 12, 2023.

Whitcombe, D., et al., "Detection of PCT products using self-probing amplicons and fluorescence," Nature Biotechnology, vol. 17, pp. 805-807 (1999).

Hodgdon, A., et al., "Ontogeny of the Barley Plant as Related to Mutation Expression and Detection of Pollen Mutations," Environmental Health Perspectives, vol. 37, pp. 5-7 (1981).

Schreiber, M., et al., "A highly mutagenised barley (cv. Golden Promise) TILLING population coupled with strategies for screening-by-sequencing," Plant Methods, vol. 15, No. 99, pp. 1-14 (2019).

Tsuda, M., et al., "Construction of a high-density mutant library in soybean and development of a mutant retrieval method using amplicon sequencing," BMC Genomics, vol. 16, No. 1014, pp. 1-18 (2015).

\* cited by examiner

SEQUENCE LISTING

```
<160> NUMBER OF SEQ ID NOS: 12

<210> SEQ ID NO 1
<211> LENGTH: 15
<212> TYPE: DNA
<213> ORGANISM: Artificial sequence
<220> FEATURE:
<223> OTHER INFORMATION: Primer

<400> SEQUENCE: 1
ccggccgaga acaag                                                    15

<210> SEQ ID NO 2
<211> LENGTH: 15
<212> TYPE: DNA
<213> ORGANISM: Artificial sequence
<220> FEATURE:
<223> OTHER INFORMATION: Primer

<400> SEQUENCE: 2
cgtggtggtg gagac                                                    15

<210> SEQ ID NO 3
<211> LENGTH: 19
<212> TYPE: DNA
<213> ORGANISM: Artificial sequence
<220> FEATURE:
<223> OTHER INFORMATION: Probe

<400> SEQUENCE: 3
aggaagacaa acctactgg                                                19

<210> SEQ ID NO 4
<211> LENGTH: 18
<212> TYPE: DNA
<213> ORGANISM: Artificial sequence
<220> FEATURE:
```

```
<223> OTHER INFORMATION: Probe

<400> SEQUENCE: 4
aggaaggcaa acctactg                                                 18

<210> SEQ ID NO 5
<211> LENGTH: 14
<212> TYPE: DNA
<213> ORGANISM: Artificial sequence
<220> FEATURE:
<223> OTHER INFORMATION: Primer

<400> SEQUENCE: 5
cgctgcttcg tcgg                                                     14

<210> SEQ ID NO 6
<211> LENGTH: 17
<212> TYPE: DNA
<213> ORGANISM: Artificial sequence
<220> FEATURE:
<223> OTHER INFORMATION: Primer

<400> SEQUENCE: 6
gagctaaaag cagcctc                                                  17

<210> SEQ ID NO 7
<211> LENGTH: 17
<212> TYPE: DNA
<213> ORGANISM: Artificial sequence
<220> FEATURE:
<223> OTHER INFORMATION: Probe

<400> SEQUENCE: 7
ctgtcctgaa acaccga                                                  17

<210> SEQ ID NO 8
<211> LENGTH: 16
<212> TYPE: DNA
<213> ORGANISM: Artificial sequence
<220> FEATURE:
<223> OTHER INFORMATION: Probe

<400> SEQUENCE: 8
ctgtcctgga acaccg                                                   16

<210> SEQ ID NO 9
<211> LENGTH: 17
<212> TYPE: DNA
<213> ORGANISM: Artificial sequence
<220> FEATURE:
<223> OTHER INFORMATION: Primer

<400> SEQUENCE: 9
tattggagtg gtcggtc                                                  17

<210> SEQ ID NO 10
<211> LENGTH: 21
<212> TYPE: DNA
<213> ORGANISM: Artificial sequence
<220> FEATURE:
<223> OTHER INFORMATION: Primer

<400> SEQUENCE: 10
cactttcatg gcaaacataa t                                             21
```

```
<210> SEQ ID NO 11
<211> LENGTH: 23
<212> TYPE: DNA
<213> ORGANISM: Artificial sequence
<220> FEATURE:
<223> OTHER INFORMATION: Probe

<400> SEQUENCE: 11
ataatccctt gaaattttcc aag                                              23

<210> SEQ ID NO 12
<211> LENGTH: 22
<212> TYPE: DNA
<213> ORGANISM: Artificial sequence
<220> FEATURE:
<223> OTHER INFORMATION: Probe

<400> SEQUENCE: 12
ataatccctt ggaattttcc aa                                               22
```

METHODS FOR PREPARING MUTANT PLANTS

CROSS-REFERENCE TO RELATED APPLICATIONS

This application is a Continuation-in-Part of International Application No. PCT/EP2020/078321, filed Oct. 8, 2020, which claims the benefit of priority to European Application No. 19202380.2, filed Oct. 10, 2019, the contents of each of which are incorporated by reference herein in their entirety for any purpose.

SEQUENCE LISTING

This application contains a Sequence Listing which has been submitted electronically in ASCII format and is hereby incorporated by reference in its entirety. Said ASCII copy, created on Apr. 7, 2022, is named 2022-04-07_01130-0019-00US_Sequence listing_ST25-final.txt and is 2,422 bytes in size.

FIELD OF THE INVENTION

The present invention provides methods of preparing organisms, for example plants or microorganisms, with specific predetermined mutation(s) in one or more nucleotides of interest (NOI(s)). The specific predetermined mutation(s) preferably may result in the identification of organisms having desired traits.

BACKGROUND OF THE INVENTION

Genetic variation is responsible for almost all phenotypic and genotypic differences in a breeding population. Genetic variation occurs naturally, commonly through environmental stresses that act on an organism, such as through increased exposure to solar radiation, extreme soil conditions or other abiotic or biotic stresses. This stress-induced variation is one of the drivers of natural diversity, adaptation and evolution of organism.

Conventional breeding utilizes this genetic variation to develop locally adapted crops. One way to increase genetic variation beyond what is already in a breeding population is to enhance the level of exposure to stress to actively induce additional genetic variation. This has been successfully done over the last 90 years via mutation breeding, which resulted in thousands of commercial crop cultivars that have beneficial traits based on the induced genetic variation. This type of mutation induction is typically exploited through the establishment of a unique breeding population, consisting of mutagenized germplasm, which then functions as source for the identification of traits and further providing parental organisms for genetic crosses with existing elite breeding lines. A notable characteristic of a mutagenized breeding population is that the population encompasses vastly increased genetic variation as compared to a natural population. To achieve a high mutation frequency, a mutagenesis treatment is often selected that causes a significant proportion of the treated material to die as a consequence of the accumulation of too many mutations with detrimental phenotypic effects. In order to select the optimal mutagenesis treatment one typically prepares a series of mutation treatments and compares the capacity of the treated organism to germinate under normal conditions. This is typically referred to as a kill-curve. A kill-curve is used as a tool to determine at what concentration and treatment duration 50% of the mutagenized material dies. This treatment is then used to generate a mutagenized breeding population, e.g. of cereal grains.

Mutation treatments can be carried out with various chemicals or radiation dosages. Both the time of the exposure to the mutagen and the relative concentration of the mutagen determine the final effect on the organism. This treatment is largely dependent on the organism.

The choice of mutagen may depend on the nature of the organism to be mutated, as some mutagens work better in some organisms than others. The time of exposure can also range from few hours to many hours and chemical concentration loads can differ depending on the exposure time, the nature of the organism, the tissue and the chemical mutagen.

In plants, induced mutations are typically heterozygous and cause a chimeric plant genotype in the initially mutagenized crop. This means that the grains harvested from a mutagenized regenerative part of a plant, such as a mutagenized seed, the M1 regenerative parts, have a high degree of genetic diversity. Therefore, mutagenized breeding populations are typically represented by M2 regenerative parts or regenerative parts (such as seeds) from later generations. In this way, most of the offspring from a plant segregate according to Mendelian genetics for two alleles only (mutant and wild type) to allow homozygous recessive mutations to be expressed (visible) at the phenotypic level. This also enables breeders to use screening techniques that are characterised by low sensitivity. As screening techniques have developed further, breeders have started to utilize the increased sensitivities of screening tools, by combining DNA of several M2 regenerative parts such as seeds or plants for the screening. While known means of screening for genetic variations in mutagenized populations were limited to screening of pools of 5-10 plants (heteroduplex analysis, Sanger sequencing, high resolution melt curve analysis), today some of these pools can be as big as 100 DNA samples when analysed with advanced sequencing technologies. However, despite notable advances, challenges remain not only with the preparation of numerous, separate DNA samples, but also with the identification of potential mutant plants that may enter a breeding program with a number of background mutations, i.e. those irrelevant to the trait of interest, but potentially affecting additional crop characteristics, such as crop yield and propagation characteristics.

There is no clear definition of a saturated crop mutation library, but the principle idea for a mutagenized breeding population is that several mutated alleles for every gene are represented in the totality of the population. In order to keep the library size small, each member of the population will have to carry mutations in several genes. In a typical barley library, each member of the population carries 100-200 mutations in coding regions. These additional coding mutations are the primary concern for the breeder after the desired trait has been identified. A truly saturated mutation library would include a mutant allele for every amino acid in every gene. In order to achieve that, the mutation frequency or the mutation density would have to be higher or the population bigger. However, markedly lower plant fitness remains a limiting factor related to the utilization of libraries prepared with increased mutation doses. Additionally the labor and time involved in assembling a library of several thousand individuals and the cost of screening such a library are limiting the potential for expanding libraries. One approach to overcome the barriers mentioned above relates to the application of higher levels of mutagen when a library of mutants is established. In this respect the further decrease of plant fitness is limiting the increase of the mutation dose for each individual. Therefore, no truly saturated mutagenized libraries exists.

Following mutagenesis with a treatment that confers a high mutation density or a high mutation frequency, backcrossing the mutant crops to a wild-type or parent crop is usually performed in order to eliminate mutations which may have occurred in other parts of the genome. This can help eliminate "side-effects" resulting from unwanted off-target mutations.

SUMMARY OF THE INVENTION

Hitherto it has been the aim of plant breeders to use breeding populations with as high a mutation rate or frequency as possible, in order to increase the probability of identifying plants carrying a specific trait. Similar strategies have been employed by microbiologists developing improved microorganisms. In contrast, the present invention provides methods to reduce the number of coding mutations per individual in a mutagenized breeding population. In other words, the invention provides methods allowing use of a population of organisms having a low rate of mutagenesis. Said organisms may for example be plants or regenerative parts thereof or microorganisms.

Following mutagenesis with a treatment that confers a high mutation density or a high mutation frequency, backcrossing mutant crops to a wild-type or parent crop is usually performed in order to eliminate mutations which may have occurred in other parts of the genome. This can help eliminate "side-effects" resulting from unwanted off-target mutations. In practical settings, the improvements of breeding issues as described herein translate into radically fewer phenotypic disadvantages in organisms of a breeding population. There will be fewer of those induced mutations, which over time, i.e. subsequent to the actual mutant identification process, confer challenging or even disadvantageous phenotypes—particularly mutations that confer phenotypic disadvantages in response to environmental stresses related to temperature and precipitation challenges. In addition, the mutants identified with the present methods can be expected to have increased viability, as they may avoid the generation of mutations which may only become apparent or relevant long time after the mutants have been obtained. Plants carrying many mutations may appear to be as viable as the parent plant at first, but may under certain conditions, e.g. drought, cold, excess rain, etc., reveal that they contain additional, as-yet unrecognized mutations which may be challenging to viability.

Many microorganisms do not reproduce sexually, and thus backcrossing to a wild-type or parent is not possible. Accordingly, low mutagenesis is highly desirable. Nevertheless, rather harsh mutagenesis are methods are usually employed. For example, Chen et al., 2017 considered mutagenesis resulting in a survival rate of only 1% to be "mild" mutagenesis. In contrast, the present invention allows use of much lower rates of mutagenesis.

A low rate of mutagenesis may be expressed as a low number of non-synonymous mutations in coding regions. A low number of coding mutations per individual reduces the detrimental effects of additional mutations in mutagenized breeding populations. For chemical mutagens, the mutation density per organisms, for example per plant is dependent on the exposure time to the mutagen, the organism, for example the specific crop, the tissue, the nature and the concentration of the chemical mutagen. For a particular plant, libraries with individuals of low mutation densities can be developed by determining optimal concentration and/or exposure time to a particular chemical mutagen using a "kill-curve" examination. For the methods of the invention it is preferable to use a concentration and/or exposure time to a given mutagen, which do not result in loss of fitness or loss of viability of the mutagenized plant population. Ideally, each plant in the mutagenized plant population to be used with the methods of the present invention has between 1 and 30 non-synonymous mutations, i.e. mutations in coding regions causing an amino acid exchange in the translated protein.

Rather than looking at the number of non-synonymous mutations, a low rate of mutagenesis can also be expressed as a high percentage of genes, which are free of non-synonymous mutations. Thus, in some embodiments, a low rate of mutagenesis may be that at least 99%, such as at least 99.8%, for example at least 99.9% of the genes of the plant, e.g. in regenerative parts of generation M1 are free of non-synonymous mutations. In some embodiments, a low rate of mutagenesis may be that at least 95%, such as at least 96%, for example at least 97%, such as at least 98%, for example at least 99% of the genes of the microorganism are free of non-synonymous mutations What specifically can be considered a low rate of mutagenesis may differ from organism to organism. In fact, what can be considered a low rate of mutagenesis may differ from plant to plant, in particular based on the ploidy of the plant. Thus, plants with a high ploidy can generally tolerate a higher rate of mutagenesis, and thus a "low rate of mutagenesis" in such plants may be much higher than a "low rate of mutagenesis" in a diploid plant. In general, a low rate of mutagenesis in a diploid plant may be that at least 99.8%, preferably at least 99.9% of all genes in M1 are free of non-synonymous mutations. In general, a low rate of mutagenesis in a plants with a higher ploidy than two, e.g. in tetraploid or hexaploid plants, a low rate of mutagenesis may be that at least 98.0%, preferably at least 99.0% of all genes in M1 are free of non-synonymous mutations. Similarly, microorganisms with a higher ploidy can generally tolerate a higher rate of mutagenesis. Thus, a low rate of mutagenesis for haploid microorganisms is preferably that at least 99% of the genes of the haploid microorganism are free of non-synonymous mutations, whereas a low rate of mutagenesis for diploid microorganisms may be at least 95%, such as at least 97% of the genes of the diploid microorganism are free of non-synonymous mutations. Non-limiting examples of haploid microorganisms include most bacteria, whereas some yeasts (e.g. *Saccharomyces*) may be diploid.

A low rate of mutagenesis may also be expressed as a low mutation frequency. For example, in a diploid plant a low rate of mutagenesis may be a mutation frequency of 1 in at least 500,000, such as 1 in at least 750,000, for example 1 in at least 1,000,000. In a tetraploid plant a low rate of mutagenesis may be a mutation frequency of 1 in at least 70,000, such as 1 in at least 100,000, for example 1 in at least 300,000. In a hexaploid plant a low rate of mutagenesis may be a mutation frequency of 1 in at least 40,000, such as 1 in at least 80,000, for example 1 in at least 200,000.

A low rate of mutagenesis may also be expressed as a high survival rate after mutagenesis. For example, low mutagenesis may be mutagenesis resulting in a survival rate of at least 30%, preferably at least 40%, even more preferably at least 45%. Aforementioned survival rates are in particular relevant in embodiments of the invention relating to microorganisms.

A low rate of mutagenesis may be obtained by using mild mutagenesis conditions. For example, a library comprising plants of a given species having a given number of genes is submitted to random mutagenesis under specific conditions, e.g. a specific concentration of mutagen for a specific duration, as illustrated in examples 3-5 and 12-14. Mutants are identified e.g. in a given region of a given length as described herein. The number of mutants identified in that region can be used to calculate the mutation density for the given mutagenesis conditions used (concentration and time).

The mutation density can also be determined by sequencing at least all the open reading frames in all the mutagenized plants or regenerative parts thereof and counting the number of mutants obtained. Knowing the size of the genome, the mutation density can thus also be calculated.

The size of the library to be used depends typically on the number of genes for a given plant. For example, barley has ca. 30000 genes, which means that a mutant library consisting of individuals that each only contain 1 non-synonymous mutation in coding regions needs to contain at least 30000 individuals to provide a mutant allele for each gene. However, in a library prepared by random mutagenesis, the mutations will statistically not be completely equally distributed, and thus significantly more than 30,000 randomly mutagenized individuals are required to ensure a library comprising one mutant allele for each gene. If one considers that barley genes on average contain 1,000 codons, a library of at least 30 million individuals is required to identify one mutation in each codon of each gene. The present methods can be performed to screen large libraries while significantly reducing backcrossing time or alleviating the need for backcrossing altogether.

Alternatively, the optimal library size can be calculated based on the mutation frequency and the number of mutations screened for as described herein. In order to obtain an optimal library size, a given number of regenerative parts ($N_p$) should be subjected to mutagenesis. An optimal Np may be calculated based on the optimal library size, the GECN number and the rate of harvest of the organism, for example the plant species after mutagenesis.

In order to screen such large libraries, the invention provides a method of pooling organisms, e.g. plants of the mutagenized breeding population, followed by the use of highly sensitive detection methods, e.g. methods currently used in diagnostics relying on detection of rare DNA, e.g. circulating tumor DNA (ctDNA). Such methods include e.g. digital PCR (dPCR) and/or use of sophisticated oligonucleotide chemistries that are ultra-specific and capable of identifying and amplifying very rare PCR fragments in a complex mix of DNA molecules. Thus, the pool of organisms may be divided into sub-pools for screening. Optimal sub-pool sizes may be calculated based on GECN number and the detection sensitivity of the detection means employed.

The methods described herein represent the basis for high throughput screening procedures which are applicable for screening very large mutant libraries, which can be generated from elite varieties or advanced breeding lines, and for screening entire breeding populations or germplasm collections. The methods can also be used for identifying genetic variants in non-transformable crop species that are not amenable to genetic modification and gene editing procedures.

Thus, the invention provides a method for identifying a mutant plant of a predefined species carrying one or more mutation(s) in nucleotide(s) of interest [NOI(s)], in a predetermined target sequence, said method comprising the steps of:
a) providing regenerative parts of a parent plant of said species, wherein at least 5,000, such as at least 10,000, such as at least 15,000, such as at least 20,000, such as at least 25,000, such as at least 30,000 regenerative parts are provided;
b) subjecting said regenerative parts to a step of mutagenesis, preferably of random mutagenesis, thereby generating a pool of regenerative parts of generation M0 representing a plurality of genotypes;
c) growing said regenerative parts of generation M0 into mature plants of generation M1 and obtaining regenerative parts of generation M1 from said mature plants;
d) optionally repeating the previous step X times to obtain plants of generation M(1+X) comprising regenerative parts of generation M(1+X);
e) dividing regenerative parts of a plurality of generation M1 or M(1+X) plants into sub-pools, each sub-pool comprising regenerative parts representing a plurality of genotypes, wherein all regenerative parts from one given mature plant are placed in the same sub-pool;
f) preparing DNA samples, such as gDNA samples or cDNA samples obtained from mRNA samples, from each sub-pool;
g) identifying sub-pool(s) comprising DNA comprising the mutation(s) using sensitive detection means;
h) identifying regenerative parts within said sub-pool comprising said mutation, thereby identifying said mutant plant, wherein said step of mutagenesis leads to a rate of mutagenesis of 1 to 30 non-synonymous mutations per cell of a regenerative part of generation M1, preferably wherein the regenerative part is a vegetative tissue, a seed, a grain, a germline cell in a seed, a grain or an embryo of said plant, pollen or an embryo, preferably the regenerative part is a seed.

The invention also provides methods for identifying a mutant microorganism of a predefined species carrying one or more mutation(s) in nucleotide(s) of interest [NOI(s)], in a predetermined target sequence, said method comprising the steps of:
I. providing microorganisms of said species;
II. subjecting said microorganisms to a step of mutagenesis, preferably of random mutagenesis, leading to a low rate of mutagenesis, wherein said mutagenesis leads to a survival rate of at least 30%, thereby generating a pool of microorganisms representing a plurality of genotypes;
III. dividing said mutagenized microorganisms into physically separated sub-pools;
IV. subjecting each sub-pool to a step of reproduction so that each sub-pool in theory comprises more than one microorganisms of each genotype,
V. preparing DNA samples, such as cDNA samples prepared from mRNA samples or gDNA samples, from each sub-pool;
VI. identifying sub-pool(s) comprising DNA comprising the mutation(s) using sensitive detection means;
VII. identifying microrganisms within said sub-pool comprising said mutation.

DETAILED DESCRIPTION OF THE INVENTION

Definitions

Figure 1:
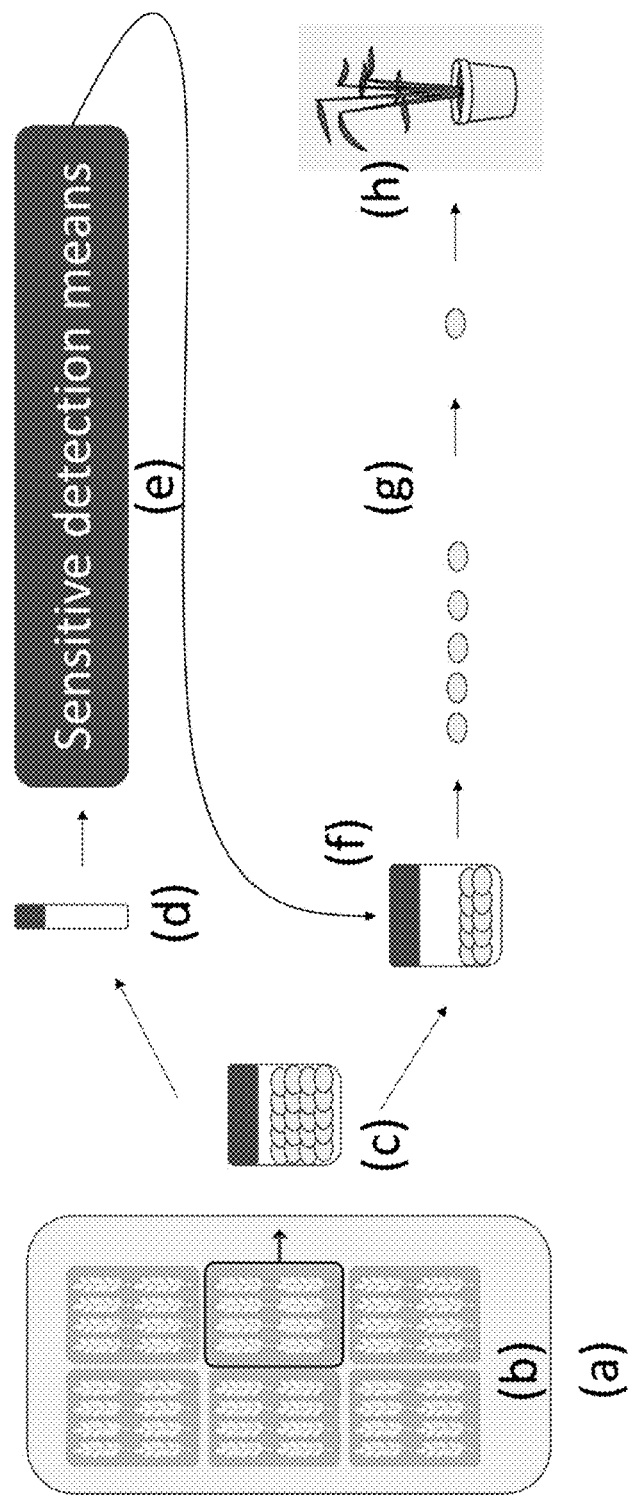
FIG. 1 Example of screening procedure. (a) Mutagenized regenerative parts, here seeds (M0), are grown to maturity in the field, (b) harvested in sub-pools of 300 plants and (c) seeds collected as bulk samples representing each pool. Bulk samples are split into fractions, one fraction (d) is utilized for DNA extraction, the other maintained as seed bank for further analysis. DNA from bulk samples (d) is analysed using sensitive detection means (e). The original pool of 300 plants that carried the mutation of interest is identified (f) and used for single seed analysis (g). (h) A mutant plant can be germinated from the identified seed.

The term "silent mutation" refers to a mutation occurring in a sequence, for example a genomic sequence of an organism, which does not result in a change of amino acid sequence. A silent mutation may thus be any mutation in a non-coding region of a genome, or it may be a mutation in a coding region of a genome, which does not change the amino acid sequence of the translation product. Synonymous mutations refer to a nucleotide substitution which does not alter the amino acid sequence of the translation product and are therefore a type of silent mutations.

The term "non-synonymous mutation" as used herein refers to a mutation occurring in a sequence, for example a genomic sequence of an organism, which does result in a change of amino acid sequence. A non-synonymous mutation thus occurs in coding regions and may thus be any mutation in a coding region of a genome which changes the amino acid sequence of the translation product, e.g. by encoding a different amino acid (e.g. missense mutations, read-through mutations), by introduction of a premature stop codon (nonsense mutations) and/or by introduction of a frameshift. The term will herein be used interchangeably with the term "coding mutation".

The term "mild mutagenesis" or "low mutagenesis" as used herein refers to a mutagenesis treatment resulting in a mutation density of 1 to 30 non-synonymous mutations (in coding regions, excluding introns), preferably as measured in a cell of a regenerative part, for example of generation M1. The mutation density can be measured by sequencing all open reading frames of the genome(s). What is considered "low mutagenesis" may be dependent on the type of plant or organism. Thus, the term "low mutagenesis" may in respect of diploid plants mean that in average at least 99.8%, preferably at least 99.9% of all genes are free of non-synonymous mutations in regenerative parts of generation M1 and in respect of plants of higher ploidy, "low mutagenesis" may mean in average at least 98.0%, preferably at least 99.0% of all genes are free of non-synonymous mutations in regenerative parts of generation M1. In respect of microorganisms, the term "low mutagenesis" may preferably mean that in average at least 95%, such as at least 96%, for example at least 97%, such as at least 98%, for example at least 99% of the genes of the microorganism are free of non-synonymous mutations. In particular, the term "low mutagenesis" may preferably mean mutagenesis of microorganism resulting in a survival rate of at least 30%, preferably at least 40%, even more preferably at least 45% of the microorganisms.

The term "mutation frequency"—abbreviated "Mf"—refers to the number of mutations within a given length of nucleic acid, for example the number of mutations obtained in a whole genome. In particular, the mutation frequency can be calculated as:

$$Mf = \frac{N_{nc}}{N_{na}}$$

wherein
$N_{nc}$ is the total number of nucleotide changes
$N_{na}$ is the number of nucleotides analysed.
In other words, $$Mf = \frac{1}{\text{'Number of nucleotides per mutation'}}$$

In embodiments of the invention, where the exact mutation frequency is not known, an estimated mutation frequency may used. Thus, the mutation frequency (Mf) may be the actual mutation frequency or an estimated mutation frequency.

The term "rate of mutagenesis" as used herein may refer to either the mutation density or the mutation frequency".

The term "allele" refers to a specific version or state of a gene. The term "mutant allele" as used here refers to a gene carrying one or more predetermined mutation(s) in the NOI(s). When the mutation is a deletion of an entire gene, the mutant allele may also be an allele lacking said gene.

The term "approximately" as used herein in relation to numbers refers to ±10%, preferably ±5%, for example to ±1%.

The term "blocking probe" as used herein refers to an oligonucleotide, which cannot be extended at the 3' end by a DNA polymerase. The blocking probe will in general be an oligonucleotide, which is identical or complementary to the target sequence, including the reference NOI linked to a blocking agent, which inhibits extension of the blocking probe by a DNA polymerase.

The term "coding region" or "coding sequence (CDS)" as used herein refers to a portion of DNA or RNA, excluding introns, which results in a protein upon translation.

The term "genotype" as used herein refers to an organism comprising a specific set of genes. Thus, two organism comprising identical genomes are of the same genotype.

An organism's genotype in relation to a particular gene is determined by the alleles carried by said organism. In diploid organisms the genotype for a given gene may be AA (homozygous, dominant) or Aa (heterozygous) or aa (homozygous, recessive).

The term "phenotype" as used herein is the composite of the organism's observable characteristics or traits.

The term "genetically effective cell number"—abbreviated "GECN"—refers to the number of cells of a plant that ultimately go on to form gametes. Such cells are herein also referred to as "germline cells". It is here regarded as the number of events that give rise to independent genotypes in the progeny. The GECN is important for calculating the expected diversity in a mutant population because each genetically effective cell will contribute different mutation events to the library. The GECN may for example be calculated as described herein below in Example 12. For the methods of the invention it is not required to use the actual GECN. Thus, GECN may be the actual GECN or an expected GECN. Most frequently, the GECN is at least 2, and thus the expected GECN may for example be 2. The GECN for a number of selected plants are provided in Table 1 below.

TABLE 1

| | |
|---|---|
| Brachypodium distachyon | ~4 |
| Avena sativa | 6 |
| Arabidopsis thaliana | 2 |
| Glycine max | 2 |
| Nicotiana plumbaginifolia | 2 |
| Medicago sativa | 3 |
| Linum usitatssimum | 4 |
| Zea mays | 4+ |
| Hordeum vulgare | 5-6 |
| Triticum aestivum | 5+ |
| Brassica napus | 4 |

In embodiments of the invention relating to other kinds of organism than plants, the GECN is considered to be 1. Thus, for microorganisms GECN is considered to be 1 in terms of the present invention.

The term "detection means for detecting nucleic acid sequences" refers to any detection means allowing detection of specific nucleic acid sequences. Thus, said detection means can detect mutations in nucleotides of interest and differentiate from wild type sequences. Many detection means are based on PCR.

The term "germination rate"—abbreviated "Gr"—refers to average germination rate of a given plant species after mutagenesis. To determine the germination rate a number of regenerative parts are incubated under conditions allowing growth, and the % of regenerative parts initiating growth is determined. By way of example, if the regenerative parts are seeds, a given number of seeds are incubated under conditions allowing germination, and the percentage of germinating seeds is determined after suitable incubation. If nothing else is indicated the germination rate is provided in %. For the methods of the invention it is not required to use the actual germination rate (Gr). Thus, the germination rate (Gr) may be the actual germination rate or an expected germination rate.

The term "harvest rate"—abbreviated "Hr"—refers to average number of organisms/regenerate parts, which can create progeny. If the organism is a plant, Hr refers to the average number of plants harvested per regenerative part subjected to mutagenesis. For some plants, the harvest rate is approx. equal to the germination rate. However, for other plant species, a much larger number of regenerative parts are sowed, compared to the number of plants actually harvested. If the organism is a microorganism, Hr refers to the % of live cells, which—after mutagenesis—can divide to create progeny. In general, when the organism is a microorganism, Hr is identical to the survival rate. If nothing else is indicated the harvest rate is provided in %. For the methods of the invention it is not required to use the actual harvest rate (Hr). Thus, the harvest rate (Hr) may be the actual harvest rate or an expected harvest rate.

The term "germline cells" refers to cells, which pass their chromosomes or heritable genetic material to their progeny, their offspring or the next generation.

The term "sensitive detection means" refers to detection means such that they allow detection of one mutant organism in a library of at least 300 organisms, even in cases where the mutant organism's genotype differs from the genotypes of the non-mutant organisms by at the most one nucleotide. Preferably they allow detection of one mutant genome in a library of 300 genomes.

The term "mutant detection probe" as used herein refers to an oligonucleotide optionally linked to detectable means, wherein the oligonucleotide is identical to, or complementary to, the target sequence, including the predetermined mutation of the NOI.

The term "PCR" as used herein refers to a polymerase chain reaction. A PCR is a reaction for amplification of nucleic acids. The method relies on thermal cycling, and consists of cycles of repeated heating and cooling of the reaction to obtain sequential melting and enzymatic replication of said DNA. In the first step, the two strands forming the DNA double helix are physically separated at a high temperature in a process also known as DNA melting. In the second step, the temperature is lowered allowing enzymatic replication of DNA. PCR may also involve incubation at additional temperature in order to enhance annealing of primers and/or to optimize the temperature(s) for replication. In a PCR, the temperature generally cycles between the various temperatures for a number of cycles.

The term "PCR reagents" as used herein refers to reagents, which are added to a PCR in addition to a sample and a set of primers. The PCR reagents comprise at least nucleotides and a nucleic acid polymerase. In addition, the PCR reagents may comprise other compounds such as salt(s) and buffer(s).

The term "dPCR" refers to digital polymerase chain reaction. It can be used to directly quantify and clonally amplify nucleic acids strands including DNA, cDNA or RNA. dPCR measures nucleic acids amounts in a more precise manner than PCR. In conventional PCR, one reaction is carried out per single sample. dPCR also relies on performing a single reaction within a sample, however the sample is compartmentalized, i.e. the sample is separated into a large number of partitions and the reaction is carried out in each partition individually.

The term "ddPCR" refers to droplet digital polymerase chain reaction. In ddPCR, one or more PCR amplifications are performed, wherein each reaction is separated into a plurality of water-oil emulsion droplets, so that PCR amplification of the target sequence may occur in each individual droplet. ddPCR is an example of a compartmentalized PCR.

The term "probability of success"—abbreviated "PS"—refers to the likelihood that a desired mutation can be identified from a given library of regenerative parts, which have been subjected to random mutagenesis. The skilled person may choose an appropriate probability of success. In general, it is preferred that the probability of success is at least 85%, preferably at least 90%, more preferably at least 95%, such as at least 98%.

The term "reproduction" as used herein refers to both sexual and asexual reproduction. Thus, reproduction may be multiplying an organism in a clonal manner (also known as "asexual reproduction"). Reproduction may also be generating progeny of an organism, wherein the progeny comprises allele(s) from the parent organism. Thus, reproduction of an organism comprising a mutant allele may refer to generating progeny of said organism, wherein the progeny comprises the mutant allele. Preferably, the mutant allele carries one or more of the mutation(s) in the NOI(s).

The term "regenerative parts of an organism" as used herein refers to any part of an organism which under the right conditions may grow into an entire organism. For example, if the organism is a plant, the term refers to any part of the plant, which may regenerate into a whole plant. Thus, the regenerative part of a plant may be any "propagating material" of said plant. The regenerative part of a plant may, for example, be a seed, a grain, a germline cell in a seed, a grain or an embryo of said plant, a vegetative tissue, pollen or an embryo of said plant. The term will herein be used interchangeably with the term "reproductive part". The term "germline cells" refers to cells which pass their chromosomes or heritable genetic material to their progeny, their offspring or the next generation.

The term "set of primers flanking a target sequence" as used herein refers to a set of two primers flanking a target sequence, so that one primer comprises a sequence identical to the 5' end of the target sequence (also referred to as "forward primer") and one primer comprises a sequence complementary to the 3' end of the target sequence (also referred to as "reverse primer"). The "set of primers" can amplify the target sequence when added to a PCR together with a nucleic acid comprising the target sequence and PCR reagents under conditions allowing amplification of said target sequence.

The term "target sequence" as used herein refers to any nucleic acid sequence within which it is desirable to generate or identify a mutation. Furthermore, the target sequence is preferably a nucleic acid sequence, which can be amplified by PCR technology using primers flanking the target sequence. In addition, the target sequence generally comprises one or more NOI(s). The invention provides methods for producing and/or identifying organism(s) carrying a mutation in said NOI. The target sequence may, for example, be a nucleic acid sequence associated with a specific trait.

The term "reference detection probe" as used herein refers to an oligonucleotide optionally linked to detectable means, wherein the oligonucleotide is identical or complementary to the target sequence, including the reference NOI. In general, the target sequence, including the reference NOI, corresponds to the target sequence prior to mutagenesis. The "reference detection probe" may also be referred to as "wild-type probe".

The term "barley" in reference to the process of making barley based beverages, such as beer, particularly when used to describe the malting process, means barley kernels. In all other cases, unless otherwise specified, "barley" means the barley plant (*Hordeum vulgare*, L.), including any breeding line or cultivar or variety, whereas part of a barley plant may be any part of a barley plant, for example an external plant structure such as leaves, stems, roots, flowers and grains, known as plant organs. It may also include any tissue or cells.

A "cereal" plant, as defined herein, is a member of the Poaceae plant family, cultivated primarily for their starch-containing seeds or kernels. Cereal plants include, but are not limited to barley (*Hordeum*), wheat (*Triticum*), rice (*Oryza*), maize (*Zea*), rye (*Secale*), oat (*Avena*), sorghum (*Sorghum*), and Triticale, a rye-wheat hybrid.

The term "grain quality" herein refers to the characteristics of a grain obtained from a plant such as a mutant plant. The term thus may refer to the moisture content of the grain, the grain weight, the percentage of discolored, broken or damage grains, the breakability of the grain, the milling quality, the protein content, the oil content, and/or the viability of the grain. Other intrinsic factors include color, composition, bulk density, odor and aroma, size and shape.

The term "% sterility" herein refers to the percentage of flowers in a plant population of a given genotype which do not produce seeds.

Method of Identifying a Mutant Plant

Herein is provided a method for identifying a mutant plant of a predefined species carrying one or more mutation(s) in nucleotide(s) of interest [NOI(s)], in a predetermined target sequence, said method comprising the steps of:

a) providing $N_p$ regenerative parts of a parent plant of said species, wherein $N_p$ is an integer of at least 5000,
b) subjecting said regenerative parts to a step of mutagenesis, preferably of random mutagenesis, thereby generating a pool of regenerative parts of generation M0 representing a plurality of genotypes;
c) growing said regenerative parts of generation M0 into mature plants, thereby obtaining regenerative parts of generation M1 from said mature plants;
d) optionally repeating the previous step X times to obtain plants of generation M(1+X) comprising regenerative parts of generation M(1+X);
e) dividing regenerative parts of a plurality of generation M1 or M(1+X) plants into sub-pools, each sub-pool comprising regenerative parts representing a plurality of genotypes, wherein all regenerative parts from one given mature plant are placed in the same sub-pool;
f) preparing DNA samples, such as cDNA samples prepared from mRNA samples or gDNA samples, from each sub-pool;
g) identifying sub-pool(s) comprising DNA comprising the mutation(s) using sensitive detection means;
h) identifying regenerative parts and/or progeny of regenerative parts within said sub-pool comprising said mutation, thereby identifying said mutant plant,
wherein said step of mutagenesis leads to a rate of mutagenesis of 1 to 30 non-synonymous mutations per cell of a regenerative part of generation M1.

It is to be understood that the present methods may in preferred embodiments be performed with seeds. However, the present methods may in some embodiments be performed with other regenerative parts of the parent plant than seeds, e.g. embryos of the parent plant may be used. In embodiments of the invention, wherein the plant is a cereal, seeds are the grains of said cereal.

The mutant plants of interest can be identified as described e.g. in examples 3-5 below, with the use of suitable PCR reagents. The PCR reagents, in general, comprise at least nucleotides and a nucleic acid polymerase. In addition, the PCR reagents may preferably also comprise one or more detection probes, e.g. a mutation detection probe and/or a reference detection probe as described herein above in the section "Detecting PCR product(s)".

Alternatively, mutants of interest may be identified by sequencing the entire genome of the mutagenized plants or regenerative parts thereof, as is known in the art. The mutation density can thus also be determined by sequencing at least all the open reading frames of some or all of the mutagenized plants or regenerative parts thereof and counting the number of mutants obtained. Knowing the size of the genome, the mutation density can thus also be calculated.

In addition to the steps outlined above, the methods of the invention may comprise one or more additional steps. The methods may, for instance, comprise a step of preparing said pool of regenerative parts such as seeds, e.g. by mutagenesis. Methods for preparing the pool of organisms are described herein below in the section "Pool".

The methods may also comprise a step of reproduction of one or more of said plants or regenerative parts, within the pool or within a sub-pool of plants or regenerative parts. This step may include cultivating said plants or regenerative parts, through one or more cycles.

In the following, reference is often only made to "seed", "crop" or "plant". However, the same considerations apply to methods using other regenerative parts of crops or plants. Each step of cultivation may result in progeny, which is not identical to the original plant, seed or other regenerative part. For example, after random mutagenesis of polyploid plants, most of the plants will carry any random mutation only on one allele, and thus be genetically heterozygous with respect to that mutation. For self-pollinating plants, generally, the progeny organisms comprise: (1) organisms without the mutation, (2) progeny organisms genetically heterozygous for the mutation and (3) progeny organisms genetically homozygous for the mutation. Thus, a pool of progeny of an original pool or plants or regenerative parts such as seeds, will not necessarily be identical to the original pool, but will, in general, at least represent any mutation in the NOI(s) present in the original pool—either as heterozygotic and/or homozygotic organisms. Thus, at least some of said progeny will comprise the mutant allele. Similarly, progeny of a sub-pool may not be identical to the original sub-pool, but will, in general, at least represent any mutation in the NOI(s) present in the original sub-pool, either in the form of heterozygotes or homozygotes.

Step e) of dividing the pool of regenerative parts into one more sub-pools may thus comprise a step of reproducing plants, or regenerative parts thereof. This may, for example, be performed simultaneously with dividing the pool into sub-pools. Alternatively, this may be done after dividing the pool into sub-pools. Thus, the methods of the invention may subsequent to step e) comprise a step of reproduction of the plants or regenerative parts thereof, within said sub-pools.

Similarly, the methods of the invention may subsequent to step f) comprise a step of reproduction of the plants or regenerative parts thereof such as seeds, within said fractions of sub-pools. However, in some embodiments of the invention, and in particular in embodiments of the invention, wherein the plant is a cereal, then it may be preferred that the methods do not comprise a step of reproduction of the plants, or regenerative parts thereof, between steps f) and g).

In some embodiments of the invention, the methods comprise a step of reproduction of the plants or regenerative parts thereof such as seeds, contained in the sub-pool or fraction thereof comprising the mutation in the NOI. Said step may be performed at any useful time, e.g. between steps h) and i) as outlined above.

The methods may also comprise a step of identifying a group of sub-pools comprising the mutation in the NOI. Said step may be performed at any useful time, but is frequently performed after step c) of the methods above—and may, for example, be performed as described in the section "Super-pools" herein below.

Method of Identifying a Mutant Microorganism

Herein is provided a method for identifying a mutant microorganism of a predefined species carrying one or more mutation(s) in nucleotide(s) of interest [NOI(s)], in a predetermined target sequence, said method comprising the steps of:

I. providing microorganisms of said species, wherein $N_p$ is an integer of at least 5000;
II. subjecting said microorganisms to a step of mutagenesis, preferably of random mutagenesis, leading to a low rate of mutagenesis, wherein said mutagenesis leads to a survival rate of at least 30%, thereby generating a pool of microorganisms representing a plurality of genotypes;
III. dividing said mutagenized microorganisms into physically separated sub-pools;
IV. subjecting each sub-pool to a step of reproduction so that each sub-pool in theory comprises more than one microorganisms of each genotype, V. preparing DNA samples, such as cDNA samples prepared from mRNA samples or gDNA samples, from each sub-pool;
VI. identifying sub-pool(s) comprising DNA comprising the mutation(s) using sensitive detection means;
VII. identifying regenerative parts and/or progeny of regenerative parts within said sub-pool comprising said mutation, thereby identifying said mutant plant.

It is preferred that the microorganisms are divided into sub-pools as soon as possible after mutagenesis, and in any event it is preferred that the microorganisms are not incubated under conditions allowing reproduction in the interim between mutagenesis and dividing microorganisms into sub-pools. This may for example be achieved by maintaining microorganisms suspended in water or buffer not containing any nutrients during mutagenesis, and until after the microorganisms have been divided into the sub-pools. Said buffer is in general free of carbohydrates and proteins, but may contain salts. Under such conditions, the microorganisms will in general not be able to reproduce.

It is to be understood that the present methods may in preferred embodiments be performed with a population of intact microorganisms. If the microorganism is a microorganism existing in different stages or forms, any stage or form may be employed.

The mutant microorganisms of interest can be identified as described e.g. in examples 13 and 14 below, with the use of suitable PCR reagents. The PCR reagents, in general, comprise at least nucleotides and a nucleic acid polymerase. In addition, the PCR reagents may preferably also comprise one or more detection probes, e.g. a mutation detection probe and/or a reference detection probe as described herein above in the section "Detecting PCR product(s)".

Alternatively, mutants of interest may be identified by sequencing the entire genome of the mutagenized microorganisms, as is known in the art. The mutation density can thus also be determined by sequencing at least all the open reading frames of some or all of the mutagenized microorganisms and counting the number of mutants obtained. Knowing the size of the genome, the mutation density can thus also be calculated.

Microorganisms may reproduce clonally in which case the progeny will have essentially the same genotype as the parent. However, some microorganisms may also reproduce sexually in which case progeny may not be identical to the parent. If the microorganism is polyploid, after random mutagenesis most of the microorganisms will carry any random mutation only on one allele, and thus be genetically heterozygous with respect to that mutation. Progeny may thus comprise: (1) progeny organisms without the mutation, (2) progeny organisms genetically heterozygous for the mutation and (3) progeny organisms genetically homozygous for the mutation. Thus, a pool may not necessarily be identical to the original pool after reproduction, but may represent any mutation in the NOI(s) present in the original pool—either as heterozygotic and/or homozygotic organisms. However, at least some of said progeny will comprise the mutant allele. Similarly, progeny of a sub-pool may not be identical to the original sub-pool, but will, in general, at least represent any mutation in the NOI(s) present in the original sub-pool, either in the form of heterozygotes or homozygotes.

The step of dividing the mutagenized microorganisms into physically separated sub-pools (step III) is preferably performed in a manner so that a total of LS viable microorganisms are divided into the sub-pools, wherein LS is an integer of at least 1500. This may for example be achieved by maintaining microorganisms suspended in water or buffer not containing any nutrients during and after mutagenesis, determining the survival rate and dividing the desired number of living cells into each sub-pool. The microorganisms may be transferred to a nutrient medium immediately before being divided into the sub-pools or after division into sub-pools. Preferably, microorganisms are transferred to a nutrient medium after they have been divided into sub-pools.

Since most microorganisms can easily be reproduced, it is frequently acceptable to mutagenize a much higher number of microorganisms than needed.

The step of subjecting each sub-pool to a step of reproduction may be performed in any useful manner. Typically, it involves incubating the microorganisms in a medium and at a temperature suitable for the particular microorganism. Said medium will depend on the particular microorganism, but it usually comprises at least a carbon source and at least a nitrogen source and possible various salts, minerals, buffers, vitamins and/or hormones.

Preferably, reproduction is performed in a manner so that each viable microorganism within the sub-pool is reproduced at least once. More preferably the sub-pools are reproduced in a manner, so that each sub-pool in theory comprises at least 2, such as at least 4, for example at least 10, such as in the range of 2 to 100 microorganisms of each genotype represented in the sub-pool.

In some embodiments of the invention, the methods comprise additional steps of reproduction of microorganisms contained in the sub-pool or fraction thereof comprising the mutation in the NOI. Said step may be performed at any useful time.

The methods may also comprise a step of identifying a group of sub-pools comprising the mutation in the NOI. Said step may be performed at any useful time, but is frequently performed after step V) of the methods above—and may, for example, be performed as described in the section "Super-pools" herein below.

Nucleotide of Interest (NOI)

The invention relates to methods for the identification of one or more organism, e.g. one or more plant(s) carrying mutation(s) in one or more nucleotides of interest. In particular, the methods allow identification of plant(s) carrying one or more predetermined mutation(s) in NOI(s). The NOIs may be inside coding regions or outside coding regions. Accordingly, the method allows identification of a plant carrying a specific mutation, while still relying on conventional breeding methods. The methods also allow identification of a microorganism carrying a specific mutation, while still relying on non-GMO methods. The mutation is preferably in a predetermined target sequence.

The mutation may be any mutation, wherein said one or more NOI(s) of interest differ from the corresponding NOI(s) in a reference sequence. Frequently, the reference sequence is a wild-type sequence. However, the reference sequence may also be any other sequence. Hence, the reference sequence may already comprise some mutations compared to a wild-type sequence, where said mutations may have occurred naturally or have been induced e.g. by mutagenesis.

The mutation may be any kind of mutation, e.g. a deletion, an insertion, a substitution or a mixture of the aforementioned. The mutation may be a synonymous mutation or a non-synonymous mutation. For example, the mutation may be (1) a mutation introducing a premature stop codon, (2) a mutation introducing a frameshift or (3) a mutation resulting in substitution of amino acid(s) in the translated protein.

The NOI(s) may be a single nucleotide or several nucleotides, and thus the NOI(s) may consist of at least one, such as 1, for example 2, such as 3, for example 4, such as 5, for example 6, such as 7, for example 8, such as 9, for example 10, such as from 10 to 20, for example from 20 to 50, such as more than 50 nucleotides.

In preferred embodiments of the invention, the NOI consists of a single nucleotide—in which case the mutation, for example, may be a substitution of a single nucleotide. Such mutations are also known as point mutations.

In other embodiments of the invention, the mutation may be a deletion of said NOI. In other embodiments, the mutation may be an insertion of one or more nucleotides between two nucleotides of interest.

In one embodiment, the reference sequence is a wild-type sequence, i.e. the most frequently naturally occurring sequence, and the mutation is thus a mutation compared to said wild-type sequence. In other embodiments, the reference sequence already comprises mutations, and the mutation is an additional mutation compared to said reference sequence.

In one embodiment, the mutation may be associated with a desirable trait within said species. Depending on the type of species, the desirable trait can be selected from a multitude of different traits. In embodiments of the invention, wherein the species is a domesticated plant, said trait could, for example, be enhanced viability, enhanced resistance to various environmental factors, enhanced growth, increased grain quality or higher yield. In embodiments of the invention, wherein the species is a plant or microorganism used for food, feed or beverage production, the trait could also relate to enhanced nutritional value, enhanced flavour properties, enhanced storage properties or enhanced usefulness for production of said food, feed or beverage. In embodiments of the invention, wherein the species is a microorganism, said trait could, for example, be enhanced viability, enhanced resistance to various environmental factors, enhanced growth or probiotic properties.

The NOI may be positioned in any target sequence in any nucleic acid. Frequently, the target sequence is part of a genomic DNA (gDNA) sequence. More preferably, the target sequence is part of a gDNA sequence. Thus, the mutation may be a mutation of the gDNA of said organism. The NOI may be positioned in any part of the gDNA, in both coding and non-coding regions. Frequently, the NOI may be positioned in any part of a gene, e.g. within a coding region (e.g. within an exon), in an intron or in regulatory regions of a gene, e.g. in promoters, terminators and/or introns. Preferably, the mutation is a coding or non-synonymous mutation.

Instead of genomic DNA, cDNA prepared from an mRNA sample may also be used to identify the desired mutation.

Plant

In preferred embodiments of the invention, the invention provides methods of identifying a plant carrying a predetermine mutation in NOI(s). The plant may be a green plant, e.g. a plant selected from the group consisting of flowering plants, conifers, gymnosperms, ferns, clubmosses, hornworts, liverworts, mosses and green algae. The plant may, for example, be a monocot or a dicot.

In particular, the plant may be a domesticated plant. Said domesticated plant may be any plant cultivated by humans, e.g. as a source of food, feed or as a raw material for production of goods or for aesthetic purposes.

In one preferred embodiment of the invention, the species is a cereal. A "cereal", as defined herein, is a member of the Graminae plant family, cultivated primarily for their starch-containing seeds or grains. Cereals include, but are not limited to, barley (*Hordeum*), wheat (*Triticum*), rice (*Oryza*), maize (*Zea*), rye (*Secale*), oat (*Avena*), sorghum (Sorghum) and the wheat-rye hybrid Triticale.

The plant may also be other domesticated plants, including tomato.

The parent plant may be a crop plant or a flowering plant, such as a plant belonging to the Brassicaceae family, the Fabaceae family, the Poaceae family, the Amaranthaceae family, the Asteraceae family, the Solanaceae family, the Rubiaceae family or the Orchidaceae family. In specific embodiments, the plant is barley. The present methods may be particularly advantageous for plants which are not easily amenable to genetic editing e.g. by transformation.

The parent plant may also be a tree or a shrub. The term "tree" here is used in its broadest sense as referring to a perennial plant with an elongated stem, or trunk, supporting branches and leaves in most species. The term thus encompasses plants such as banana trees or coconut trees. Shrubs are small to medium-sized perennial woody plants. The present methods are advantageous for identifying mutants of trees or shrubs. Trees and shrubs have a slow growth, hence it is particularly advantageous to bypass the needs of back-crossing for identifying mutants of interest, as this results in considerable shortening of the time required to identify such mutants. In general the present methods are particularly advantageous for any plant having a long reproduction cycle.

Microorganism

The present invention also relates to methods of identifying a mutant organism of a predefined species carrying one or more mutation(s) in nucleotide(s) of interest [NOI(s)], in a predetermined target sequence.

Said organism may for example be a microorganism. The microorganism may be any microorganism, but preferably the microorganism is a unicellular organism.

The microorganism may be a prokaryote, such as bacterium. Said bacteria may be either Gram negative or Gram positive bacteria. Examples of bacteria include those used in production of food, e.g. bacteria of a genus selected from the group consisting of *Acetobacter, Arthrobacter, Alactobacillus, Bacillus, Bifidobacterium, Brachybacterium, Brevibacterium, Carnobacterium, Corynebacterium; enterococcus, Gluconacetobacter, Hafnia, Halomonas, Kocuria, Lactobacillus, Lactococcus, Leuconostoc, Macrococcus, Microbacterium, Micrococcus, Pediococcus, Propionibacterium, Proteus, Pseudimonas, Psychrobacter, Staphylococcus, Streptomyces, Tetragenococcus, Weissella* and *Zymomonas*.

The species may also be an eukaryote, e.g. selected from the group consisting of yeast, fungi and algae.

In one embodiment, the species is selected from the group consisting of fungi. Thus, the species may be a unicellular or a multicellular organism. For example, the species may be a fungus of a genus selected from the group consisting of *Aspergillus, Candida, Cystofilobasidium, Cyberlindnera, Debaryomyces, Fusarium, Geotrichum, Issatchenkia, Kazachstania, Kloeckera, Klyveromyces, Mucor, Neurospora, Penicillium, Pichia. Rhiozopus, Rhodosporidium, Rhodotorula, Saccharomyces, Torulaspora, Torulopsis, Thrichosporon, Verticillium, Yarrowia* and *Zygotorulaspora*.

In particular, the species may be yeast, such as yeast selected from the group consisting of *Saccharomyces cerevisiae, Saccharomyces pastorianus, Saccharomyces bayanus* and *Saccharomyces uvarum*. Other yeasts of interest include Brettanomyces species, and the like.

When the microorganism is a microorganism, which exists both as haploid spores and polyploid cells (e.g. diploid cells), either the haploid spores or the diploid cells may be employed in the methods of this invention.

Pool

The methods of the invention comprise providing $N_p$ organisms. For example, the methods of the invention comprise providing $N_p$ microorganisms or $N_p$ regenerative parts of a given plant and mutagenizing said regenerative parts of said microorganisms or plant to obtain a pool of regenerative parts representing a plurality of genotypes. Said plant may, for example, be any of the plants described herein above in the section "Plant". The pool or regenerative parts thus refers to the mutagenized regenerative parts which are obtained from the regenerative parts provided in step a) of the present methods. Consequently, the pool of regenerative parts consists of the same number of regenerative parts as the number of regenerative parts provided in step a). For example, if 30,000 regenerative parts are provided in step a), the pool of (mutagenized) regenerative parts counts 30,000 mutagenized regenerative parts.

Thus, the pool of regenerative parts comprises a plurality of regenerative parts, which all belong to the same species, but which represent different genotypes of said plant. The pool may comprise more than one regenerative part of each genotype. However, the pool must comprise a plurality of regenerative parts of different genotypes.

In embodiments of the invention relating to microorganisms, it may be more relevant to determine the library size (LS) rather than the Np, because a very large number of microorganisms can in general easily be supplied. In so far as the methods relate to microorganisms, LS refers to the number of viable microorganisms, which are divided into the sub-pools.

Thus, in embodiments relating to microorganisms, $$Np \text{ is preferably at least} = \frac{LS * 100}{Hr},$$

wherein Hr is the survival rate after mutagenesis, however Np may be much higher.

As described in Examples 6 and 7 below, in order to obtain a certain probability of success, a certain optimal library size (OLS) may preferably be used. Optimal in this context means the optimal library size to get the desired probability of success. In embodiments, wherein the organism is a plant, the library size is the total number of different genotypes represented in the regenerative parts of generation M1 or M(1+x).

Regardless of the type of organism, the OLS is dependent on the mutation frequency and the number of mutations screened for. In preferred embodiments, the OLS is determined as described in Example 6 below.

Based on the OLS, an optimal number of organisms, e.g. regenerative parts to be mutagenised (Np) may be determined. If the organism is a plant, the optimal Np is dependent on the number of germline cells of the particular plant as well as on the rate of harvest after mutagenesis.

In particular, the optimal $N_p$ ($ON_p$) may be determined as described in Example 7 below.

In preferred embodiments, $N_p$ is in the range of 0.7*ONp to 1.3*ONp, wherein $$ONp = \frac{\frac{OLS \times 100}{Hr}}{GECN};$$

wherein Hr is the average of organisms/regenerate parts, which can create progeny after mutagenesis in %; and OLS is optimal library size, wherein $$OLS = \frac{\log\left(1 - \frac{PS}{100}\right)}{\log(1 - (1 - (1 - (Mf \times n))))}$$

wherein PS is the probability of success in %; and
Mf is the mutation frequency; and
n is the number of mutations screened for; and
wherein step b) or step II. comprises a step of random mutagenesis leading to a mutagenesis frequency of Mr.

In embodiments wherein the organism is not a plant, GECN is typically 1.

In embodiments wherein the organism is a microorganism, Hr is preferably identical to the survival rate in % after mutagenesis.

In embodiments wherein the organism is a plant, Hr is preferably the expected average harvest rate of said plant species after mutagenesis in %.

For some plant species, e.g. for cereals, the harvest rate is approximately the same as the germination rate, and for such plant species, the germination rate Gr may be used in stead of the harvest rate to calculate ONp.

In embodiments, wherein the organism is a microorganism it is preferred that the library size (LS) is in the range of 0.5*OLS to 5*OLS, preferably in the range of 0.5*OLS to 2*OLS, for example in the range of 0.7*OLS to 1.3*OLS, wherein $$OLS = \frac{\log\left(1 - \frac{PS}{100}\right)}{\log(1 - (1 - (1 - (Mf \times n))))}$$

wherein PS is the probability of success in %; and
Mf is the mutation frequency; and
n is the number of mutations screened for; and
wherein step b) or step II) comprises a step of random mutagenesis leading to a mutagenesis frequency of Mr.

Preferably, said mutation frequency corresponds to a low rate of mutagenesis. The rate of mutagenesis in terms of % genes free of non-synonymous mutations can be calculated based on the mutation frequency, the number of genes and the average length of genes in a particular plant using the following formula:

$$GFoNSM = Gn \times Gl \times Mf \times \frac{Nsnm}{100}$$

wherein GFoNSM is the number of genes free of non-synonymous mutations in %; and
Gn is the number of genes in the specific plant, Gl is the average length of a gene in bp (Tiessen et al 2012), Mf is the mutation frequency, Nsnm is the average number of non-synonymous mutations caused by mutagenesis in %.

Typically, Nsnm is in the range of 60 to 70%, such as 66%. If the exact Nsnm is unknown an Nsnm of 66% can be used.

In the prior art, the rate of mutagenesis is frequently described in terms of mutation frequency. For example, sometimes a mutation frequency of 1 in 500,000 in *Arabidopsis thaliana* plants of generation M2 is described. That corresponds to approx. 57 genes with coding mutations in *Arabidopsis thaliana* plants of generation M1 or to 99.79% of all genes being free of non-synonymous mutation in *Arabidopsis* plants of generation M1. Furthermore, sometimes a mutation frequency of 1 in 10,000 in *Arabidopsis thaliana* plants of generation M2 is described. That corresponds to approx. 2862 genes with coding mutations in *Arabidopsis thaliana* plants of generation M1 or to 89.65% of all genes being free of non-synonymous mutation in *Arabidopsis* plants of generation M1.

In one embodiment Np is in the range of 0.9*ONp to 1.1*ONp, preferably the Np is in the range of 0.9*ONp to 1.1*ONp.

Sometimes, the actual value of one or more of the parameters required for calculation of the ONp is unknown. In such cases, the expected value rather than the actual value may be employed. Thus, if the rate of harvest after mutagenesis is unknown, the expected rate of harvest may be used. The expected rate of harvest may be based on the knowledge of the skilled person from similar mutagenesis proceedings. Similar, if the exact mutation frequency is unknown, the expected mutation frequency may be used. The expected mutation frequency may be based on the knowledge of the skilled person from similar mutagenesis proceedings.

The person performing the methods of the invention may select a suitable probability of success. Typically, the probability of success is at least 85%, preferably at least 90%, more preferably at least 95%, such as at least 98%.

In some embodiments, the pool (i.e. $N_p$) comprises at least 5,000 microorganisms or regenerative parts, such as at least 10,000 microorganisms or regenerative parts, such as at least 15,000 microorganisms or regenerative parts, such as at least 20,000 microorganisms or regenerative parts, such as at least 25,000 microorganisms or regenerative parts, such as at least 30,000 microorganisms or regenerative parts, such as at least 40,000 microorganisms or regenerative parts, such as at least 50,000 microorganisms or regenerative parts, such as at least 60,000 microorganisms or regenerative parts, such as at least 70,000 microorganisms or regenerative parts, such as at least 80,000 microorganisms or regenerative parts, such as at least 90,000 microorganisms or regenerative parts, such as at least 100,000 microorganisms or regenerative parts, such as at least 200,000 microorganisms or regenerative parts, such as at least 300,000 microorganisms or regenerative parts, such as at least 400,000 microorganisms or regenerative parts, such as at least 500,000 microorganisms or regenerative parts, such as at least 600,000 microorganisms or regenerative parts, such as at least 700,000 microorganisms or regenerative parts, such as at least 800,000 microorganisms or regenerative parts, such as at least 900,000 microorganisms or regenerative parts, such as at least $10^6$ microorganisms or regenerative parts, such as at least $2.10^6$ microorganisms or regenerative parts, such as at least $3.10^6$ microorganisms or regenerative parts, such as at least $4.10^6$ microorganisms or regenerative parts, such as at least $5.10^6$ microorganisms or regenerative parts, such as at least $6.10^6$ microorganisms or regenerative parts, such as at least $7.10^6$ microorganisms or regenerative parts, such as at least $8.10^6$ microorganisms or regenerative parts, such as at least $9.10^6$ microorganisms or regenerative parts such as at least $10^7$ microorganisms or regenerative parts or regenerative parts of a plant or more, with different genotypes. In some embodiments, the pool comprises between 5,000 and 100,000 microorganisms or regenerative parts, such as between 10,000 and 90,000 microorganisms or regenerative parts, such as between 15,000 and 85,000 microorganisms or regenerative parts, such as between 20,000 and 80,000 microorganisms or regenerative parts, such as between 25,000 and 90,000 microorganisms or regenerative parts, such as between 30,000 and 100,000 microorganisms or regenerative parts, such as between 30,000 and 75,000 microorganisms or regenerative parts, such as between 50,000 and 75,000 microorganisms or regenerative parts, such as between 50,000 and 1,000,000 microorganisms or regenerative parts, such as between 100,000 and 500,000 microorganisms or regenerative parts, or between 500,000 and 1,000,000 microorganisms or regenerative parts, or between 600,000 and 900,000 microorganisms or regenerative parts, or between 900,000 and 1,500,000 microorganisms or regenerative parts. In some embodiments, the regenerative parts are seeds.

It is preferred that the pool of organisms comprises a sufficient number of microorganisms or regenerative parts of a plant, with different genotypes, such that the pool theoretically may comprise all possible mutations in all genes of said microorganisms or plant. For example, in embodiments of the invention, wherein the species is barley, it is believed that a pool comprising ~1,500,000 randomly mutagenized barley grains will theoretically comprise all possible mutations in all genes of said barley for a mutation density of 1 mutation in 1 500 kbp of genomic DNA. To improve the efficiency of the methods of the invention, the pool may comprise at least 2×, such as at least 3× as many microorganisms or regenerative parts of a plant, with different genotypes which are theoretically expected to comprise all possible mutations. Thus the pool may comprise at least 5,000 microorganisms or regenerative parts, such as at least 10,000 microorganisms or regenerative parts, such as at least 15,000 microorganisms or regenerative parts, such as at least 20,000 microorganisms or regenerative parts, such as at least 25,000 microorganisms or regenerative parts, such as at least 30,000 microorganisms or regenerative parts, such as at least 40,000 microorganisms or regenerative parts, such as at least 50,000 microorganisms or regenerative parts, such as at least 60,000 microorganisms or regenerative parts, such as at least 70,000 microorganisms or regenerative parts, such as at least 80,000 microorganisms or regenerative parts, such as at least 90,000 microorganisms or regenerative parts, such as at least 100,000 microorganisms or regenerative parts, such as at least 200,000 microorganisms or regenerative parts, such as at least 300,000 microorganisms or regenerative parts, such as at least 400,000 microorganisms or regenerative parts, such as at least 500,000 microorganisms or regenerative parts, such as at least 600,000 microorganisms or regenerative parts, such as at least 700,000 microorganisms or regenerative parts, such as at least 800,000 microorganisms or regenerative parts, such as at least 900,000 microorganisms or regenerative parts, such as at least $10^6$ microorganisms or regenerative parts, such as at least $2.10^6$ microorganisms or regenerative parts, such as at least $3.10^6$ microorganisms or regenerative parts, such as at least $4.10^6$ microorganisms or regenerative parts, such as at least $5.10^6$ microorganisms or regenerative parts, such as at least $6.10^6$ microorganisms or regenerative parts, such as at least $7.10^6$ microorganisms or regenerative parts, such as at least $8.10^6$ microorganisms or regenerative parts, such as at least $9.10^6$ microorganisms or regenerative parts such as at least $10^7$ microorganisms or regenerative parts or more, with different genotypes. In some embodiments, the pool comprises between 5,000 and 100,000 microorganisms or regenerative parts, such as between 10,000 and 90,000 microorganisms or regenerative parts, such as between 15,000 and 85,000 microorganisms or regenerative parts, such as between 20,000 and 80,000 microorganisms or regenerative parts, such as between 25,000 and 90,000 microorganisms or regenerative parts, such as between 30,000 and 100,000 microorganisms or regenerative parts, such as between 30,000 and 75,000 microorganisms or regenerative parts, such as between 50,000 and 75,000 regenerative parts, such as between 50,000 and 1,000,000 microorganisms or regenerative parts, such as between 100,000 and 500,000 regenerative parts, or between 500,000 and 1,000,000 microorganisms or regenerative parts, or between 600,000 and 900,000 microorganisms or regenerative parts, or between 900,000 and 1,500,000 microorganisms or regenerative parts. In some embodiments, the regenerative parts are seeds. This may, for example, be the case in embodiments, wherein the species in question is barley.

In some embodiments, the pool of regenerative parts may comprise at least 5,000,000, such as in the range of 1,000,000 to 100,000,000 regenerative parts of a plant, with different genotypes. In some embodiments, the pool of microorganisms or regenerative parts represents at least 5,000 different genotypes, such as at least 10,000 different genotypes, such as at least 15,000 different genotypes, such as at least 20,000 different genotypes, such as at least 25,000 different genotypes, such as at least 30,000 different genotypes, such as at least 40,000 different genotypes, such as at least 50,000 different genotypes, such as at least 60,000 different genotypes, such as at least 70,000 different genotypes, such as at least 80,000 different genotypes, such as at least 90,000 different genotypes, such as at least 100,000 different genotypes, such as at least 200,000 different genotypes, such as at least 300,000 different genotypes, such as at least 400,000 different genotypes, such as at least 500,000 different genotypes, such as at least 600,000 different genotypes, such as at least 700,000 different genotypes, such as at least 800,000 different genotypes, such as at least 900,000 different genotypes, such as at least $10^6$ different genotypes, such as at least $2.10^6$ different genotypes, such as at least $3.10^6$ different genotypes, such as at least $4.10^6$ different genotypes, such as at least $5.10^6$ different genotypes, such as at least $6.10^6$ different genotypes, such as at least $7.10^6$ different genotypes, such as at least $8.10^6$ different genotypes, such as at least $9.10^6$ different genotypes such as at least $10^7$ different genotypes or more. In some embodiments, the pool represents between 5,000 and 100,000 different genotypes, such as between 10,000 and 90,000 different genotypes, such as between 15,000 and 85,000 different genotypes, such as between 20,000 and 80,000 different genotypes, such as between 25,000 and 90,000 different genotypes, such as between 30,000 and 100,000, such as between 30,000 and 75,000 different genotypes, such as between 50,000 and 75,000 different genotypes, such as between 50,000 and 1,000,000 different genotypes, such as between 100,000 and 500,000 different genotypes, or between 500,000 and 1,000,000 different genotypes, or between 600,000 and 900,000 different genotypes, or between 900,000 and 1,500,000 different genotypes.

One advantage of the methods of the present invention is that the methods allow screening a large number of microorganisms or regenerative parts of a plant (such as seeds) of different genotypes. Thus, the pool may comprise a very large number of microorganisms or regenerative parts of different genotypes. Further, the methods of the invention may allow identifying a plant with a predetermined mutation in any NOI. In order to be able to identify a plant with a mutation in any NOI, this may require that the pool comprises a large number of different genotypes, such as the aforementioned numbers of different genotypes.

In a preferred embodiment of the invention, the pool of microorganisms or regenerative parts of a plant (such as seeds) is prepared by mutagenesis, in particular, by random mutagenesis. Thus, a plurality of regenerative parts may be subjected to mutagenesis in order to obtain the pool of regenerative parts. Said mutagenesis may in particular be random mutagenesis, which—for example—may be performed as described below.

It may be sufficient to subject a regenerative part of the said multicellular organism to said random mutagenesis. In such embodiments, either a plurality of regenerative parts of a plant—such as a plurality of seeds of a plant, or a mixture thereof—is subjected to random mutagenesis.

The pool may comprise a plurality of microorganisms or regenerative parts that represent a plurality of genotypes. Thus, the pool may comprise a plurality of regenerative parts, which have been subjected to mutagenesis. However, the pool may also comprise progeny of microorganisms or regenerative parts, which have been subjected to mutagenesis.

Figure 2:
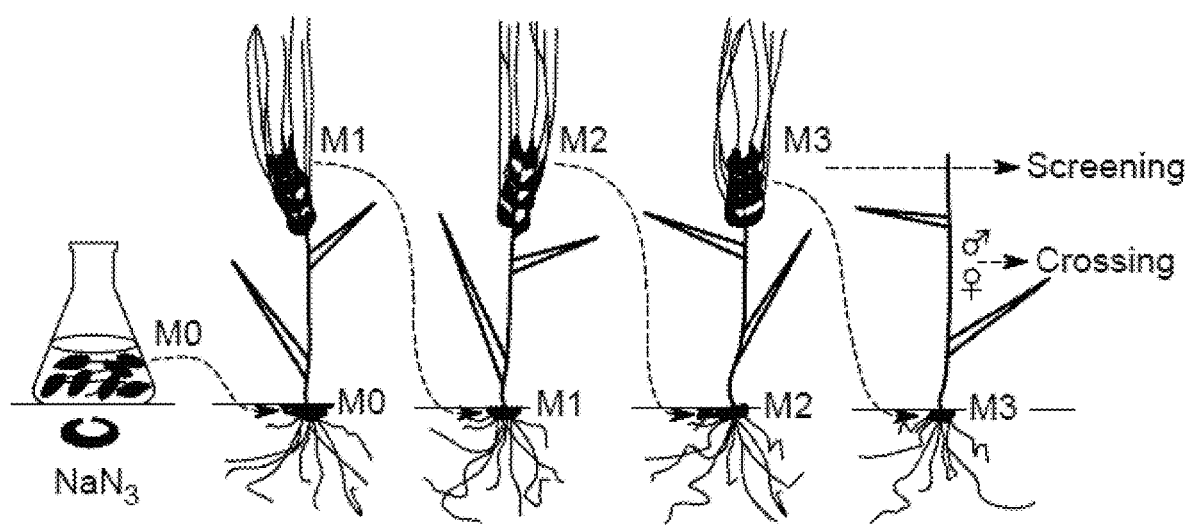
FIG. 2 Propagation of mutant barley grains. This figure exemplifies the propagation of mutant grains, here barley mutagenized with sodium azide. Mutant seeds of generation M0 give rise to a plant of generation M1. The seeds of the M1 generation plant give rise to a plant of generation M2. The seeds of the M2 plant give rise to a plant of generation M3, which can be used for screening and crossing.

Herein, regenerative parts (e.g. seeds such as cereal grains), which have been subjected to mutagenesis may be referred to as generation M0. Said regenerative parts, e.g. seeds such as cereal grains, may be sown and allowed to develop into mature plants, the regenerative parts (e.g. seeds such as cereal grains) of which are considered generation M1. Generation M1 regenerative parts, e.g. seeds, may be sown and allowed to grow into mature plants the regenerative parts (such as seeds) of which are considered generation M2 and so forth. Plants of the variety used for establishing a library, which have not yet been subjected to mutagenesis, may also be referred to as "parent plant". This is illustrated in FIG. 2.

The pool of regenerative parts may comprise regenerative parts such as seeds, e.g. cereal grains, of any of the aforementioned generations. The pool of regenerative parts may also comprise regenerative parts, e.g. seeds such as cereal grains, of generation M1, M2 or M3. It is preferred that the pool of regenerative parts comprises regenerative parts of generation M1, preferably all regenerative parts in said pool of regenerative parts are of generation M1.

Random Mutagenesis

Traditionally, an efficient mutagenesis protocol is considered a crucial, basic requirement for a successful breeding program or for developing new traits in microorganisms.

However, the present invention provides methods comprising use of "mild" mutagenesis, resulting in the generation of in the range of 1 to 30 non-synonymous mutations in coding regions per plant or other organism, e.g. microorganism.

Random mutagenesis is currently based on the use of a chemical mutagen or irradiation. Historically, the effectiveness of a mutagen has been measured in terms of biological effects. It is, however, desirable to establish a relationship between the observed biological effect to a well-defined and easily measurable physical quantity characterizing the amount of irradiation or chemical mutagen conferring the effect.

Random mutagenesis may be performed in any useful manner, e.g. by irradiation or chemical treatment. Irradiation may be UV-irradiation, X-ray irradiation or radioactive irradiation. Chemical mutagenesis may include treatment with any mutagenizing chemical, for example a chemical selected from the group consisting of sodium azide ($NaN_3$), alkylating agents such as N-ethyl-N-nitrosourea (ENU), methylnitrosoguanidine (MNNG) and ethyl methanesulfonate (EMS) or the alkylating agents mentioned below. $NaN_3$, ENU and EMS are often used to generate mutants at random.

To induce random mutations in a plant's DNA, in particular genomic DNA, kernels or regenerable vegetative plant tissues can be treated with a mutagen, or a mixture of mutagens—including, but not limited to, alkylating agents such as: sulfonates, e.g. ethylmethane sulfonate (EMS), diethyl sulfonate (DES); sulphur mustards, e.g. ethyl-2-chloroethyl sulphide; nitrogen mustards, e.g. 2-chloroethyl-dimethyl amine, and; epoxides, e.g. ethylene oxide. Others include ethyleneimine, hydroxylamine ($NH_2OH$), N-methyl-N'-nitro-N-nitrosoguanidine (MNNG), $NaN_3$ and diazomethane. The treated tissues or kernels can then be propagated to generate off-spring organisms. Such random mutagenesis may be used with plants, such as crop plants, or any of the plants described in the section "Plant".

To induce random mutations in the DNA, in particular genomic DNA, of a microorganism, typically a population of said microorganism can be treated with a mutagen, or a mixture of mutagens or they can be irradiated. Said mutagens may be any of the aforementioned mutagens, which also can be used in mutagenesis of plants. The treated microorganisms can then be propagated to generate progeny microorganisms.

The methods of the invention are not restricted to any particular type of mutagenesis, provided that it is a "mild" or "low" mutagenesis. Said low mutagenesis may be. a mutagenesis leading to a rate of mutagenesis of 1 to 30 non-synonymous mutations in coding regions per plant. In some embodiments, this corresponds to mutations of interest occurring at a frequency corresponding to 1 mutation per 1.5 bases of genomic DNA. In some embodiments, low mutagenesis in diploid plants may be that more than 99.8%, preferably more than 99.9% of all genes are free of non-synonymous mutations in M1, and low mutagenesis in plants with a higher ploidy than two may be that more than 98.0%, preferably more than 99.0% of all genes are free of non-synonymous mutations in M1. In some embodiments, low mutagenesis may be mutagenesis resulting in a survival rate of at least 30%, preferably at least 40%, even more preferably at least 45%.

Mutation rates are known for many types of mutagenesis, and the skilled person will readily be able to calculate the optimal mutagen dosage, concentration and/or exposure time for each type of mutagenesis to obtain the desired mutation density or mutation frequency. Alternatively, the skilled person can test mutagenesis to identify optimal mutagen dosage, concentration and/or exposure time to obtain a desired low rate of mutagenesis for the plant species. The present methods are based on performing mutagenesis in any of the ways described herein to obtain a low rate of mutagenesis. Said low rate of mutagenesis may in particular be a mutagenesis rate resulting in 1 to 30 non-synonymous mutations in coding regions per plant. Alternatively, the low rate of mutagenesis may be that more than 99.8%, such as 99.9% of all genes are free of non-synonymous mutations in diploid plants in M1, and the low rate of mutagenesis may be that at least 98.0%, preferably at least 99.0% of all genes are free of non-synonymous mutations in plants with a higher ploidy than two in M1. In one embodiment the low mutagenesis may be mutagenesis resulting in a survival rate of at least 30%, preferably at least 40%, even more preferably at least 45%.

For example, a library comprising plants of a given species having a given number of genes is submitted to a random mutagenesis under specific conditions, e.g. a specific concentration of a mutagen for a specific duration, as illustrated in examples 3-5. Mutants are identified e.g. in a given region of a given length as described herein. The number of mutants identified in that region can be used to calculate the mutation density for the given mutagenesis conditions used (concentration and time). For example, if a fragment of 1,000 bp is analyzed for 10,000 individuals and a total of 10 mutants are identified among the analyzed base pairs, the mutation rate under those conditions is $10/(1,000 \times 10,000) = 1 \cdot 10^{-6}$ mutation per bp. In other words, the mutation density under these conditions can be seen as equal to the number of mutants identified divided by the product of the number of elements (regenerative parts) screened with the length of the region screened, as shown below:

Mutation density=(number of identified mutants)/
((number of mutagenized individuals)×(length of the analysed region)).

In some embodiments, the mutagenesis results in 1 non-synonymous mutation in coding regions per microorganism or plant. In other embodiments, the mutagenesis results in 2, 3, 4, 5, 6, 7, 8, 9, 10, 11, 12, 13, 14, 15, 16, 17, 18, 19, 20, 21, 22, 23, 24, 25, 26, 27, 28, 29 or 30 non-synonymous mutations in coding regions per microorganism or plant. In addition to the non-synonymous mutations in coding regions, the plant may further comprise silent mutations, e.g. in non-coding regions.

In preferred embodiments, the mutagenesis step is such that the rate of mutagenesis is at the most 1 non-synonymous mutation every 1000 genes, such as at the most 1 non-synonymous mutation every 5000 genes, such as at the most 1 non-synonymous mutation every 10000 genes, such as at the most 1 non-synonymous mutation every 20,000 genes, such as at the most 1 non-synonymous mutation every 30,000 genes, such as at the most 1 non-synonymous mutation every 5,000 genes. 1 non-synonymous mutation every 1000 genes means that if the plant has 6000 genes 6 genes are expected to carry non-synonymous mutations while 5994 genes are expected to be devoid of non-synonymous mutations in coding regions, but may still comprise other mutations, for example synonymous mutations, outside the coding regions. In other preferred embodiments the mutagenesis step is such that the rate of mutagenesis is that at least 99.8%, preferably at least 99.9% of all genes are free of non-synonymous mutations in diploid plants in M1, and the low rate of mutagenesis may be that at least 98.0%, preferably at least 99.0% of all genes are free of non-synonymous mutations in plants with a higher ploidy than two in M1. In some embodiments, a low rate of mutagenesis may be that at least 95%, such as at least 96%, for example at least 97%, such as at least 98%, for example at least 99% of the genes of the microorganisms are free of non-synonymous mutations In some embodiments, the mutagenesis step translates to at the most 30 non-synonymous mutations in coding regions, such as at the most 25 non-synonymous mutations in coding regions, such as at the most 20 non-synonymous mutations in coding regions, such as at the most 15 non-synonymous mutations in coding regions, such as at the most 10 non-synonymous mutations in coding regions, such as at the most 5 non-synonymous mutations in coding regions, such as at the most 4 non-synonymous mutations in coding regions, such as at the most 3 non-synonymous mutations in coding regions, such as at the most 2 non-synonymous mutations in coding regions, such as 1 non silent-mutation in a coding region in plants of generation M1 or M(1+X).

Methods involving mutagenesis have often been performed under conditions such that a notable fraction (up to 50%) of the mutagenized organisms are not viable and die. By contrast, since the present methods can be performed on a great number of plants or regenerative parts thereof, it is advantageous to perform the random mutagenesis in conditions such that most plants survive. Preferably, the mutagenesis is performed in conditions such that 90% of the regenerative parts survive the step of mutagenesis, such as at least 91%, of the regenerative parts, such as at least 92% of the regenerative parts, such as at least 93% of the regenerative parts, such as at least 94% of the regenerative parts, such as at least 95% of the regenerative parts, such as at least 96% of the regenerative parts, such as at least 97% of the regenerative parts, such as at least 98% of the regenerative parts, or such as at least 99% of the regenerative parts survive the step of mutagenesis.

Traditional mutagenesis of microorganisms has been performed under conditions where more than 99% of the mutagenized microorganisms are not viable and die from mutagenesis. In embodiments of the invention, where the organism is a microorganism, the mutagenesis is preferably performed under conditions such that at least 30% of the microorganisms survive the step of mutagenesis, preferably at least 40%, of the microorganisms, even more preferably at least 45% of the microorganisms survive the step of mutagenesis. In other words, low mutagenesis results in a survival rate of at least 30%, preferably at least 40%, even more preferably at least 45% of the microorganisms.

For most crops, ethyl methanesulfonate (EMS) is often the mutagen of choice. However, mutagenesis of barley is typically performed using a sodium azide ($NaN_3$) based mutagenesis treatment.

Sodium azide (1.5 mM for 2 hours) treatment of barley typically leads to mutation densities of 1 mutation every 500,000 bp (Szurman-Zubrzycka et al., 2018). This number is typically determined by analysing sequencing data from various genes within a population. At a mutation density of 1:500,000 bp, and a barley genome of 5.3 GB, each barley plant will carry approx. 10,000 mutations. The coding sequence of barley is ca. 65 Mb, which is between 1-2% of the total genome. Based on that it can be assumed that ca. 100-200 of the 10,000 induced mutations are in coding regions.

Approximately one third of mutations, e.g. sodium azide mutations in a coding region, lead to a silent nucleotide substitution. Thus, if mutagenesis is performed using sodium azide the Nsnm is typically 66%. It can therefore be assumed that 50-100 mutations of the 10,000 induced mutations will cause a non-synonymous mutation in a coding region. Since mutations occur randomly across the genome it can be assumed that the 50-100 amino acid substitutions in coding regions, are in different coding regions, or genes, across the genome. Mutation density is crop and treatment dependent. In other crops, the mutation density in a typical TILLING library can range from 1 in every 20,000 bp to 1 in every 1 million bp of total genomic DNA.

In some embodiments, the mutagen is $NaN_3$. In such embodiments, $NaN_3$ is used preferably at a concentration of less than 1 mM or less for 2 hours or less, such as 0.9 mM or less, such as 0.8 mM or less, such as 0.7 mM or less, such as 0.6 mM or less, such as 0.5 mM or less, such as 0.4 mM or less, such as 0.3 mM or less. In one embodiment, $NaN_3$ is used preferably at a concentration of approximately 0.3 mM for in the range of 1.5 to 2.5 hours.

The step of random mutagenesis may also be performed with EMS, preferably at a concentration of 4% or less for 2 hours or less, such as 3% or less, such as 2% or less, such as 1.5% or less, such as 1% or less, such as 0.75% or less, such as 0.5% or less, such as 0.4% or less, such as 0.3% or less, such as 0.2% or less, such as 0.1% or less, such as 0.1% for 24 hours or less.

When subjecting microorganisms, such as bacteria, e.g. *Lactobacillus* to random mutagenesis it may be performed by subjecting said bacteria to in the range of 0.5 to 2% EMS, such as to in the range of 1 to 2% EMS, for example in the range of 1.2 to 1.6% EMS for in the range of 10 min to 3 hours, such as in the range of 10 min. to 2 hours, for example in the range of 20 min. to 2 hours, such as in the range of 20 min. to 1 hour, for example in the range of 20 to 40 min.

The random mutagenesis may also be performed by other methods known in the art, such as random CRISPR mutagenesis, in which specific CRISPR arrays can be used to randomly mutagenize populations of plants (Lu et al., 2017) or of microorganisms. For example, arrays of CRISPR guide RNAs can be synthesized and randomly transformed into plants, thus generating a library of plants each carrying a CRISPR-induced mutation in the genome.

Dividing a Pool of Regenerative Parts into Sub-Pools

The methods of the invention may comprise a step of dividing the pool of regenerative parts of a plant such as seeds, of generation M1 or M(1+X) into one or more sub-pools, wherein each sub-pool comprises a plurality of regenerative parts of a plant, such as seeds. Each sub-pool comprises regenerative parts of a plant representing a plurality of genotypes—importantly, each sub-pool comprises all the regenerative parts from one given mature plant.

In some embodiments, where the regenerative parts are of generation M(1+X), it may be preferred that all regenerative parts of all progeny of a given M0 generation plant are placed in the same sub-pool.

In practice, taking an example where the regenerative parts are seeds of plants grown in a field, once the pool of mutagenized seeds (of generation M0) has been obtained, the entire pool is sawn in the field. The entire field represents another pool of seeds of generation M1, comprising all the seeds of the plants resulting from the pool of seeds of generation M0. The total pool of seeds of generation M1 are herein referred to as the "library". The size of the library is different to Np, based on the GECN number and the rate of harvest. The library of seeds of generation M1 are divided into sub-pools for example as follows: the field is divided in different areas, and the seeds from one area represent one sub-pool. These seeds are then in this example of generation M1. The sub-pool of seeds is then divided in fractions, as described in detail herein elsewhere.

If seeds of generation M2 or later generations are used, the plants to obtain seeds of later generations may in some embodiments preferably be grown in a manner rendering it possible to place all seeds of progeny plants of the same M0 plant into the same sub-pool.

The skilled person will be able to transfer the above example to plants grown under different conditions, such as in the green house, in separate pots etc.

The methods may also comprise a step of dividing mutagenized microorganisms into physically separated sub-pools. This may be done by any useful method, for example mutagenized microorganisms may be aliquoted into different containers or wells.

As described herein below in Example 8 an optimal size of sub-pool may be determined based on the detection sensitivity of the (sensitive) detection means employed and the GECN number. Thus, preferred embodiments, the optimal sub-pool size is determined as described in Example 8 below.

Thus, the maximum sub-pool size (SPm) may be calculated as follows:

$$SPm = \frac{Y}{GECN}$$

wherein the detection sensitivity is 1 in Y.

When the organism is not a plant, for example when the organism is a microorganism, GECN is not relevant, and there considered to be 1. In such cases, the SPm is equal to Y.

In one embodiment each sub-pool comprises regenerative parts from a number of mature plants, said number being in the range of 0.5*SPm to SPm, wherein all regenerative parts from one given mature plant are placed in the same sub-pool.

In one embodiment, each sub-pool comprises regenerative part from in the range of 0.7*SPm to SPm mature plants.

In one embodiment each sub-pool initially comprises in the range of 0.5*SPm to SPm viable microorganisms, such as in the range of 0.7*SPm to SPm viable microorganisms. In this context, the term "initially" refers to the number of viable microorganisms contained in each sub-pool prior to any reproduction. Thus, each sub-pool comprises viable microorganisms, which in principle represent aforementioned number of different genotypes.

Usually, the pool is divided into a plurality of sub-pools, preferably into at least 2 sub-pools, such as into at least 50 sub-pools, such as into at least 100 sub-pools, preferably into at least 200 sub-pools, more preferably into at least 300 sub-pools, even more preferably into at least 400 sub-pools, yet more preferably into at least 500 sub-pools, even more preferably into at least 1000 sub-pools, yet more preferably into at least 1500 sub-pools.

In some embodiments, the pool is divided into at least 500, such as at least 1000, for example at least 1500 sub-pools. This may, in particular, be the case in embodiments of the invention, wherein the pool comprises a large number of organisms of different genotypes.

There is, in principle, no upper limit to the number of sub-pools. Typically, however, the pool is divided into at the most 50,000, such as at the most 25,000, e.g. at the most 10,000 sub-pools.

In some embodiments, the pool is divided into in the range of 90 to 1000 sub-pools.

Each sub-pool preferably comprises a plurality of microorganisms or regenerative parts of a plant, representing a plurality of genotypes. Preferably, each sub-pool comprises at least 10, more preferably at least 100, even more preferably at least 200, even more preferably at least 300, even more preferably at least 400, even more preferably at least 500, yet more preferably at least 1,000, even more preferably at least 5,000 microorganisms or regenerative parts of a plant, with different genotypes. In some embodiments, each sub-pool comprises in the range of 500 to 5,000, such as in the range of 600 to 2000 microorganisms or regenerative parts with different genotypes.

In some embodiments each sub-pool comprises in the range of 1,000 to 2,000 microorganisms or regenerative parts representing different genotypes.

It is also preferred that each sub-pool comprises more than one microorganism or regenerative part of each genotype. When the organism is a plant, this may be achieved by ensuring that all regenerative parts of any given mature plant are placed in the same sub-pool. In embodiments, where the organism is a microorganism this may be ensured by subjecting the sub-pool to a step of reproduction after dividing the mutagenized microorganisms into the sub-pools.

In particular, it is preferred that each sub-pool comprises a sufficient amount of microorganisms or regenerative parts of each genotype in order to randomly divide the sub-pool into 2, 3, or 4 fractions in a manner such that each fraction, theoretically, comprises microorganisms or regenerative parts, representing each genotype of the sub-pool. Thus, it is preferred that each sub-pool comprises at least 5, preferably at least 10, even more preferably at least 15 microorganisms or regenerative parts representing each genotype. This may, in particular, be the case in embodiments of the invention, wherein the species is a cereal.

Figure 3:
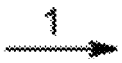
FIG. 3 Division of a pool into sub-pools. An example of a method for dividing the pool into sub-pools is provided.
Figure 3:
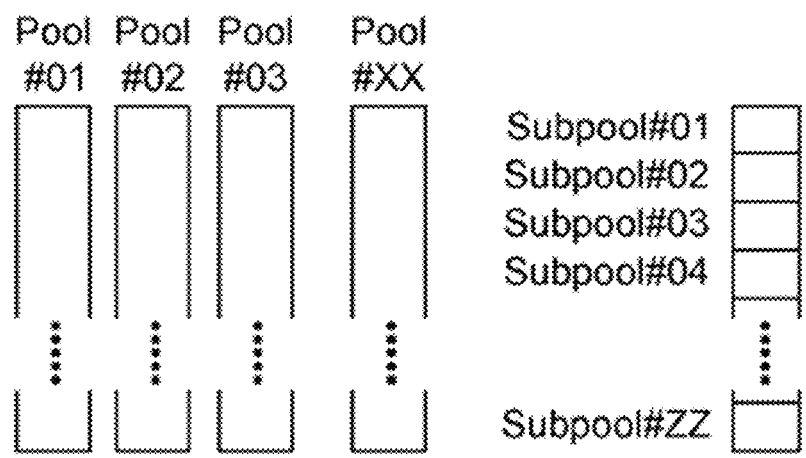

An illustration of a method for dividing the pool into sub-pools is provided in FIG. 3.

In general, the sub-pool may be prepared in a manner such that all regenerative parts of one particular plant are contained within one sub-pool. Thus, in one embodiment of the invention, the methods comprise the steps of:
  Providing a plurality of regenerative parts such as seeds of a plant, e.g. cereal grains;
  Mutagenizing said seeds, thereby obtaining regenerative parts such as seeds of generation M0;
  Growing said regenerative parts such as seeds of generation M0 into mature plants, and obtaining regenerative parts such as seeds from said mature plants, wherein said regenerative parts such as seeds are seeds of generation M1;
  Optionally repeating the previous step X times to obtain plants comprising regenerative parts such as seeds of generation M(1+X);
  Obtaining regenerative parts such as seeds of either generation M1 or M(1+X) from said mature plants, thereby obtaining a pool of regenerative parts such as seeds (e.g. a pool of cereal grains);
  Dividing said pool into sub-pools, wherein all regenerative parts such as seeds (e.g. cereal grains) from a given mature plant are placed into the same sub-pool.

These steps are illustrated in FIG. 2 using barley as an example. The method may comprise the steps illustrated in FIG. 2. The skilled person will understand that similar principles can be applied to other plants. Thus, the steps illustrated in FIG. 2 may be performed using any flowering plant, and are thus not limited to barley. Other mutagenesis protocols may be used, these are not limited to mutation with sodium azide. Also, the steps illustrated in FIG. 2 may be performed using any number of mutated plants.

Accordingly, the method may comprise the steps of:
  Providing a plurality of regenerative parts of a plant such as seeds, e.g. cereal grains;
  Mutagenizing said regenerative parts, thereby obtaining regenerative parts of generation M0;
  Optionally cultivating said regenerative parts of generation M0 into mature plants, and obtaining regenerative parts such as from said mature plants, wherein said regenerative parts are regenerative parts of generation M1;
  Optionally repeating the previous step X times to obtain plants comprising regenerative parts of generation M(1+X);
  Cultivating regenerative parts such as seeds of generation M0, M1 or M(1+X) in discrete field plots into mature plants, wherein the regenerative parts of said mature plants constitute the pool of regenerative parts;
  Dividing said areas into field sub-plots;
  Harvesting all regenerative parts such as seeds of all plants within one field sub-plot, thereby obtaining a sub-pool of regenerative parts (e.g. a sub-pool of seeds, such as cereal grains), which may be referred to as "Grain total".

Instead of cultivating regenerative parts such as seeds in field plots, these may be cultivated in any useful manner to allow dividing of the plants into sub-groups, thus obtaining sub-pools. For example, the regenerative parts may be cultivated in separate containers, each comprising one or more plants. The seeds may also be cultivated in a greenhouse.

Examples of methods for dividing a pool of regenerative parts into a sub-pool are provided in PCT/EP2017/065516, in particular in the section entitled "WS2: preparing an ordered library of grains derived from mutated cereal plants".

Identifying Sub-Pools

The methods of the invention comprise the steps of dividing a pool of microorganisms or regenerative parts such as seeds, into sub-pools. DNA samples from each sub-pool are then prepared and used to identify sub-pool(s) comprising DNA comprising the mutation(s).

Preferably, the DNA samples are prepared by a method comprising the steps of (1) dividing each sub-pool into fractions; (2) preparing DNA samples from an entire fraction.

Preferably the fractions of each sub-pool are prepared in a manner so that at least two fractions in theory comprises microorganisms or regenerative parts of a plant of all the genotypes represented in the sub-pool. Preferably, all fractions in theory comprises microorganisms or regenerative parts of all the genotypes represented in the sub-pool. This may for example be accomplished by mixing all microorganisms or regenerative parts of a sub-pool well, randomly dividing the sub-pool into in the range of 2 to 10 fractions, such as into in the range of 2 to 6 fractions, for example into in the range of 2 to 4 fractions. It is preferred that said at least 2 fractions each comprises in the range of 10 to 50%, such as in the range of 15 to 50%, for example in the range of 20 to 50% of the microorganisms or regenerative parts of the sub-pool.

Thus, the sub-pool may be divided in at least 2 fractions, such as at least 3 fractions, such as at least 4 fractions, or more, each fraction in theory comprising microorganisms or regenerative parts of all the genotypes represented in the sub-pool.

As described in Example 10, the optimal fraction size may be calculated based on the average number of regenerative parts per plant and the GECN number. Thus, in one embodiment it is preferred that a DNA sample is prepared from a fraction of the regenerative parts of a sub-pool as follows:
  i. randomly dividing each sub-pool into fractions, wherein a first fraction comprises in the range of $$\frac{GECN * 100}{RPp}\%$$

to $$\frac{GECN * 500}{RPp}\%$$

of the regenerative parts of the sub-pool; and wherein said first fraction comprises at the most 50% of said regenerative part;
  ii. preparing DNA samples of the entire first fraction of each sub-pool,
wherein RPp is the number of regenerative parts per mature plant.

Analysis of said fraction, and hence identification of the sub-pool, may comprise the steps of:
  a) Preparing DNA samples, each comprising DNA from each genotype within one fraction, which, for example, may be performed as described herein below in the section "Preparing DNA samples";
  b) Using sensitive detection means to detect the presence of the mutation(s) in the NOI(s) of interest.
Step a) may in particular comprise that DNA (or RNA) is extracted from the entire fraction.

The step of using sensitive detection means may comprise performing a plurality of PCR amplifications each comprising a plurality of compartmentalised PCR amplifications, e.g. carried out as described herein below in the section "PCR amplification comprising a plurality of compartmentalised PCR amplifications"; and detecting PCR amplification product(s) comprising the mutation(s) in the NOI(s) of interest, thereby identifying the fraction(s) of interest, and hence the sub-pool(s) of interest, e.g. done as described herein below in the section "Detecting PCR amplification product(s)".

The sub-pool may, for example, be directly identified provided that the PCR amplification product(s) comprises the mutation(s) in the NOI(s) that can be directly detected after, or during the PCR amplification. This may, for example, be done if the PCR amplification product(s) comprise(s) detection means, which give rise to one or more detectable signal(s), provided that the PCR amplification product(s) comprise(s) the target sequence(s) comprising the mutation(s) in the NOI(s). Such detection means are described in more detail below in the section "Detecting PCR product(s)", and may, for example, be mutation detection probes.

One example of a method for identification of a fraction comprising one or more specific mutation(s) comprises the following steps:
  Providing sub-pools and dividing each sub-pool into fractions;
  Preparing a sample from an entire fraction of each sub-pool;
  Preparing a DNA sample, such as genomic DNA or mRNA, from said sample;
  Preparing PCR amplifications with all of the individual DNA samples from all of the sub-pools, e.g. in individual wells of a plate, e.g. in microtiter plates;
  Selecting those samples which comprise the mutation(s) in the NOI(s).

Preparing DNA Samples

The present methods do not require that DNA samples are prepared individually for each of the microorganisms or regenerative parts comprised within one fraction. In fact it is preferred that an entire fraction is used to obtain a DNA sample, which in practice is a pooled DNA sample comprising DNA from all the genotypes comprised within the fraction. The DNA sample may be a gDNA sample or it may be cDNA, for example a cDNA sample prepared from an mRNA sample as is known in the art. Thus, preferably the methods do not comprise the step of preparing individual DNA samples for each microorganism or plant or regenerative part of one fraction or sub-pool.

The methods of the invention comprise one or more steps of preparing DNA samples, in particular gDNA or cDNA samples prepared from mRNA samples, preferably gDNA samples. In particular, the methods may comprise one step of preparing DNA samples from an entire fraction.

The methods of the invention may also comprise a step of preparing DNA samples from a secondary sub-pool.

In general, said DNA samples of sub-pools are prepared in a manner so that the DNA sample in theory comprises DNA from each genotype within a sub-pool. The DNA sample may be prepared from an entire fraction, while the potential for reproduction of microorganisms or the regenerative parts of each genotype are maintained in the other fraction(s) of the sub-pool.

Thus, each sub-pool in general comprises more than one individual microorganism or seed, or regenerative parts, of each genotype, so that when divided in fractions, each fraction comprises at least one individual microorganism or regenerative part of each genotype. In particular, it may be preferred that each sub-pool comprises a sufficient amount of regenerative parts of each genotype in order to be able to randomly divide the sub-pool or the super-pool into in the range of 2 to 10 fractions, such as in the range of 2 to 6 fractions, for example into 2, 3, or 4 fractions in a manner such that each part in theory comprises microorganisms or regenerative parts representing each genotype of the sub-pool or super-pool.

In this manner, a part of the microorganisms or regenerative parts from the sub-pool, e.g. in the range of 10 to 90%, preferably in the range 10 to 50%, such as in the range of 15 to 50%, for example in the range of 20 to 50% of the microorganisms or regenerative parts of each sub-pool may be used for preparing the DNA sample. Said part of the regenerative parts is also referred to herein as "sample of regenerative parts". Said part of the microorganisms is also referred to herein as "sample of microorganisms". The remainder of the microorganisms or regenerative parts of the sub-pool may be stored under conditions maintaining the reproductive potential of said microorganisms or regenerative parts. It may be sufficient to store seeds of said plants. Seeds, e.g. cereal grains, may frequently be stored in any dry and dark place. Microorganisms may e.g. be frozen under conditions preserving the integrity of the microorganisms.

Whereas the sub-pool preferably comprise several individual microorganisms or regenerative parts of each genotype as noted herein elsewhere, then the secondary sub-pool frequently may comprise only a few—sometimes even only one—individual microorganisms or regenerative parts of each genotype. This may particularly be the case, when the organism is a plant.

As explained above, when obtaining DNA from sub-pools, typically the DNA is extracted from entire fractions of the sub-pools. However, when obtaining DNA from the secondary sub-pools, said DNA may also be obtained from samples from individual regenerative parts. When samples are obtained from individual regenerative parts it may be preferred that the samples are obtained in a manner not significantly impairing said regenerative parts, with respect to the potential for reproduction. Thus, the DNA sample may be prepared from a sample comprising or consisting of a part of the regenerative part, such as a seed, that is not essential for reproduction. The sample may be obtained in any useful manner depending on the species, e.g. by using biopsy, cutting, drilling, grating, tearing or by applying a syringe equipped with a needle. By way of example, in embodiments where the species is a cereal, then said sample preferably comprises a part of the cereal grain, which is not essential for reproduction. The sample may be obtained in different manners, e.g. by cutting-off part(s) of the grain using any sharp instrument, such as a knife, scalpel or scissors, grating-off part of the grain, or it may be obtained by drilling a hole into the grain. In the latter case, the sample may be the flour obtained after drilling.

When obtaining DNA from secondary sub-pools of microorganisms, said DNA may also be obtained by a method comprising:
 i. Reproducing microorganisms of the secondary sub-pool in a clonal manner, wherein clones are spatially separated from each other
 ii. Extracting DNA from part of each clone.

Once either the fraction of regenerative parts, or the sample obtained from the regenerative parts, or parts thereof, or the sample of microorganisms is available (herein also collectively referred to as "sample"), the DNA sample may be prepared from said samples in any useful manner. If said samples contain large structures, e.g. entire seeds, the first step for preparing a DNA sample such as a gDNA sample will typically involve dividing said contents of said sample into smaller parts, for example, by physical means, e.g. by crushing or milling. Methods of preparing the DNA sample typically comprise the steps of disrupting cells and/or tissues, e.g. by detergent, by enzymes (e.g. lyticase), by ultrasound or by combinations thereof—thereby creating a crude lysate. Said lysate may be separated from any remaining debris by any useful means. The crude lysate may constitute the DNA sample comprising a gDNA sample. Alternatively, the DNA, e.g. the gDNA or mRNA to be used to obtain a cDNA sample, may be further purified, e.g. by separating said DNA from the remainder of the lysate, e.g. by binding to a selective matrix, centrifugation, gradient centrifugation and/or precipitation (e.g. using a precipitating agent, such as a salt, an alcohol or magnetic beads). Prior to such separation, other components of the lysate—including proteins and/or nucleoproteins—may be denatured or destroyed, e.g. by use of enzymes and/or denaturing agents. Other RNA-containing molecules may be removed, e.g. with the aid of enzymes. Useful methods for preparing DNA samples such as cDNA samples or gDNA samples are, for example, described in Sambrook et al., Molecular Cloning—Laboratory Manual, ISBN 978-1-936113-42-2.

Sensitive Detection Means

The methods of the invention comprise a step of identifying a fraction of a sub-pool, and hence identifying the corresponding sub-pool of interest, using detection means for detecting nucleic acid sequences, preferably sensitive detection means. The term "sensitive detection means" refers to detection means such that they allow detection of one mutant organism in a library of at least 300 organisms, even in cases where the mutant organism's genotype differs from the genotypes of the non-mutant organisms by at the most one nucleotide. Preferably the detection means are sensitive enough to allow detection of one mutant genome in a library of 300 genomes, even when the mutant genome only differs from the 299 other genomes by only one nucleotide. In some embodiments, the detection means allow detection of one mutant organism such as a plant in a library of at least 300 organisms such as plants, for example one mutant in a library of at least 400 organisms, for example one mutant in a library of at least 500 organisms, for example one mutant in a library of at least 600 organisms, for example one mutant in a library of at least 700 organisms, for example one mutant in a library of at least 800 organisms, for example one mutant in a library of at least 900 organisms, for example one mutant in a library of at least 1,000 organisms, for example one mutant in a library of at least 1,100 organisms, for example one mutant in a library of at least 1,200 organisms, for example one mutant in a library of at least 1,300 organisms, for example one mutant in a library of at least 1,400 organisms, for example one mutant in a library of at least 1,500 organisms, for example one mutant in a library of at least 1,600 organisms, for example one mutant in a library of at least 1,700 organisms, for example one mutant in a library of at least 1,800 organisms, for example one mutant in a library of at least 1,900 organisms, for example one mutant in a library of at least 2,000 organisms, for example one mutant in a library of at least 2,500 organisms, for example one mutant in a library of at least 3,000 organisms, for example one mutant in a library of at least 4000 organisms, for example one mutant in a library of at least 5,000 organisms, or more.

For example, the sensitive detection means have a detection sensitivity of 1 in at least 1,000, such as a detection sensitivity of 1 to in the range of 1,000 to 10,000 for example a detection sensitivity of 1 to in the range of 1,000 to 5,000.

For example, the methods of the invention may comprise a step of performing a plurality of PCR amplifications each comprising a DNA sample from one fraction, i.e. from all the microorganisms or regenerative parts present in one fraction (for example prepared as described in the sections above), thereby amplifying the target sequence. Each PCR amplification may comprise a plurality of compartmentalised PCR amplifications each comprising part of said DNA sample, one or more set(s) of primers flanking the target sequence and PCR reagents.

RNase H2-dependent PCR (rhPCR) may improve the specificity of PCR by incorporating blocked primers containing a single ribonucleotide residue, which are activated via enzymatic cleavage. Specifically, blocked primers for rhPCR contain a single ribonucleotide residue that induce cleavage by RNase H2 following perfect hybridization to the target DNA. Cleavage occurs on the 5' side of the RNA base, thus releasing the RNA base together with the 3' blocking moiety, permitting selective amplification of target DNA fragments. A tail sequence can be incorporated into the amplicon to combine the use of a 5'-nuclease assay based reporter system with rhPCR. In some embodiments, the PCR reaction is an rhPCR reaction, e.g. as described in example 2.

In another instance, Cas nucleases with trans-cleavage activity, like Cas12a, can be utilized as sensitive detection means (Chen et al., 2018). Recently several Cas nucleases with trans-cleavage activity were reported, that can be utilized to detect nucleotide substitutions in complex samples. The method takes advantage of CRISPR's ability to guide a molecule, in this case a Cas12a nuclease, to a specific stretch of DNA or RNA. The CRISPR molecule can be designed to be specific for a target sequence containing a NOI. Upon binding to the target sequence including the NOI, Cas12a will cleave the specific RNA or DNA strand. Unlike conventional CRISPR associated nucleases like Cas9, Cas12a will also start to cleave single stranded DNA or RNA molecules that are in close proximity to the nuclease. Here a single stranded DNA or RNA strand, a reporter molecule, labelled with a fluorescent marker and a quencher are utilized as a substrate for Cas12a trans-cleavage. In this example, CRISPR-Cas12a specifically binds to a DNA or RNA sequence that contain a NOI only, and starts cleaving a reporter molecule that is in close proximity. Cleavage of the reporter molecule will release the fluorophore and signal the presence of a DNA or RNA molecule containing a NOI. If the reaction only contains a target sequence without the NOI, the CRISPR-Cas12a complex does not bind to the target and therefore will not initiate trans-cleavage of the reporter molecules, which remain quenched.

The entire PCR reaction comprising a plurality of compartmentalised PCR amplifications may be prepared in a number of different manners. In one embodiment, the PCR amplification comprising a plurality of compartmentalised PCR amplifications may be conducted as a digital PCR (dPCR) amplification. Any dPCR amplification known to the skilled person may be used with the invention. In general, at least one dPCR amplification comprising a plurality of compartmentalised PCR amplifications will be prepared for each DNA sample prepared. Thus, at least one dPCR amplification comprising a plurality of compartmentalised dPCR amplifications will be prepared per fraction of each sub-pool.

In general, the compartmentalised dPCR amplification is prepared in a method comprising the steps of:
  Preparing a dPCR amplification comprising the DNA sample, a set of primers flanking the target sequence and PCR reagents;
  Partitioning said dPCR amplification so that nucleic acid molecules within the sample are localized and concentrated within a plurality of spatially separated compartments;
  Performing a dPCR amplification;
  Detecting dPCR-based amplification products.

The DNA sample may a gDNA sample or a cDNA sample obtained from an mRNA sample. In some embodiments, the DNA sample is a gDNA sample.

Said separated compartments may be any separate compartments in which PCR amplifications can be performed. For example, it may be well of a plate, e.g. a well of a micro well plate or a microtiter plate, it may be microfluidic chambers, it may be capillaries, it may be the dispersed phase of an emulsion, or it may be a droplet or miniaturized chambers of an array of miniaturized chambers. The separated compartments may also be discrete spots on a solid support, e.g. discrete nucleic acid binding surfaces.

It is generally preferred that the DNA sample is distributed randomly into the samples for compartmentalised dPCR amplification. It is also preferred that each compartmentalised dPCR amplification only comprises a small number of nucleic acids comprising the target sequence. Due to the nature of random distribution, there may be some variation in the number of nucleic acid molecules comprised in each compartmentalised dPCR amplification. In one embodiment, each compartmentalised dPCR amplification comprises, in average, at the most 10, such as at the most 5 nucleic acid molecules comprising the target sequence.

In one preferred embodiment of the invention, the dPCR amplification comprising a plurality of compartmentalised PCR amplification is a droplet digital polymerase chain reaction (ddPCR). ddPCR is a method to perform dPCR that is based on water-oil emulsion droplet technology. The PCR amplification is fractionated into a plurality of micro-droplets, and PCR amplification of the target sequence occurs in each individual droplet. In general, ddPCR technology uses PCR reagents and work flows similar to those used for performing conventional PCRs. Thus, the partitioning of the PCR amplification is a key aspect of the ddPCR technique.

Accordingly, compartmentalised ddPCR amplifications may be contained in droplets, which may, for example, include emulsion compositions, or mixtures of two or more immiscible fluids (for example as described in U.S. Pat. No. 7,622,280 or as described in the examples herein below). The droplets can be generated by devices described in WO/2010/036352. In particular, the droplets can be prepared using a droplet generator, for example QX200 Droplet Generator available from Bio-Rad Laboratories, USA (hereinafter abbreviated Bio-Rad). The term emulsion, as used herein, can refer to a mixture of immiscible liquids (such as oil and water). The emulsions may, for example, be water in oil droplets, e.g. as described in Hindson et al. (2011). The emulsions can thus comprise aqueous droplets within a continuous oil phase. The emulsions can also be oil-in-water emulsions, wherein the droplets are oil droplets within a continuous aqueous phase. The droplets used herein are normally designed to prevent mixing between compartments, with the content of an individual compartment not only being protected from evaporation, but also from coalescing with the contents of other compartments. Thus, each droplet can be regarded as a spatially separated compartment.

Each droplet for ddPCR may have any useful volume. Preferably, however, the droplets have a volume in the nL-range. Accordingly, it is preferred that the droplet volume, on average, is in the range of 0.1 to 10 nL.

Microfluidic methods of producing emulsion droplets using microchannel cross-flow focusing or physical agitation are known to produce either monodisperse or polydisperse emulsions. The droplets can be monodisperse droplets. Also, the droplets can be generated such that their sizes do not vary by more than ±5% of the average size of the droplets. In some cases, the droplets are generated such that the droplet sizes only vary with ±2% of the average size of droplets.

Higher mechanical stability can be useful for microfluidic manipulations and higher-shear fluidic processing (e.g. in microfluidic capillaries or through 90° turns, such as valves in fluidic paths). Pre- and post-thermally treated droplets, or capsules, can be mechanically stable to standard pipet manipulations and centrifugation.

A droplet can be formed by flowing an oil phase through an aqueous sample. The aqueous phase can comprise, or consist, of components in a PCR amplification, e.g. a PCR amplification comprising the DNA sample, a set of primers flanking the target sequence and PCR reagents, such as any of the PCR reagents described herein below in the section "PCR reagents".

The oil phase can comprise a fluorinated base oil, which can be additionally stabilized by combination with a fluorinated surfactant such as a perfluorinated polyether. In some cases, the base oil can be one or more of HFE 7500, FC-40, FC-43, FC-70, or other common fluorinated oil. In some cases, the anionic surfactant is Ammonium Krytox (Krytox-AM), the ammonium salt of Krytox FSH, or morpholino derivative of Krytox-FSH.

The oil phase can further comprise an additive for tuning the oil properties, such as vapor pressure, viscosity or surface tension. Non-limiting examples include perfluorooctanol and 1H,1H,2H,2H-Perfluorodecanol. The oil phase may also be a droplet generating oil, e.g. the Droplet Generation Oil available from Bio-Rad.

The emulsion can formulated to produce highly monodisperse droplets having a liquid-like interfacial film that can be converted by heating into micro-capsules having a solid-like interfacial film; such micro-capsules can behave as bioreactors that retain their contents through a reaction process, such as PCR amplification. The conversion to microcapsule form can occur upon heating. For example, such conversion can occur at a temperature of greater than 50, 60, 70, 80, 90, or 95° C. In some cases, this heating occurs using a thermocycler. During the heating process, a fluid or mineral oil overlay can be used to prevent evaporation.

In some cases, the droplet is generated using a commercially available droplet generator, such as Bio-Rad QX100™ Droplet Generator or Bio-Rad QX200™ Droplet Generator. The ddPCR and subsequent detection may be carried out using a commercially available droplet reader, such as Bio-Rad QX100 or QX200™ Droplet Reader.

Each PCR amplification can be compartmentalized into any suitable number of compartments. However, in one preferred embodiment, each PCR amplification is compartmentalized into in the range of 1,000 to 100,000 compartments (e.g. droplets). For example, each PCR amplification may be compartmentalized into in the range of 10,000 to 50,000 compartments (e.g. droplets). For example, each PCR amplification may be compartmentalized into in the range of 15,000 to 25,000 compartments (e.g. droplets). Further, each PCR amplification may be compartmentalized into approximately 20,000 compartments (e.g. droplets).

Organisation of Sub-Pools

Prior to the step of identifying sub-pools, the methods of the invention may also comprise a step of organising said sub-pools in a manner, which eases the identification of a sub-pool comprising regenerative parts such as seeds comprising the mutation of interest.

For example, fractions of DNA samples from several sub-pools may be combined into "Super-pools". Super-pools comprising DNA comprising the mutation of interest may then be identified using extremely sensitive detection means. Afterwards only sub-pools comprised in super-pools, comprising the DNA with the mutation of interest must be tested. Useful methods for preparing and testing super-pools are described in international patent application WO 2018/001884.

In another example sub-pools are placed into multi-dimensional grids, and super-pools are prepared of the sub-pools in each dimension. This is easiest explained using a 2 dimensional grid as example. Each sub-pool given a coordinate (x,y) in said grid. Fractions of DNA samples of all sub-pools with a given coordinate X are pooled and tested for the presence of DNA comprising the mutation of interest. Similarly, fractions of DNA samples of all sub-pools with a given coordinate Y are pooled and tested for the presence of DNA comprising the mutation of interest. Once super-pools comprising DNA samples from a given coordinate X and a given coordinate Y are identified as comprising DNA with the mutation of interest, a sub-pool comprising said DNA can be identified based on its coordinates X and Y. The skilled person will understand that a similar system can be made using multiple dimensions, rather than only two.

Thus, rather than testing each sub-pool for the presence of DNA comprising the mutation of interest it is also comprised within the methods of the invention, that the sub-pools are organised so that groups of sub-pools can be tested together. The testing may for example be done using any of the sensitive detection means described herein.

PCR Reagents

In some embodiments, the method encompasses performing several PCR amplifications, wherein at least some of these PCRs may comprise a plurality of compartmentalised PCR amplifications.

Regardless of whether said PCR comprises compartmentalised PCR amplifications or not, then the PCR amplifications will in general comprise a DNA sample, a set of primers flanking the target sequence and PCR reagents. Said PCR reagents may be any of the PCR reagents described herein in this section.

The PCR reagents, in general, comprise at least nucleotides and a nucleic acid polymerase. The nucleotides may be deoxy-ribonucleotide triphosphate molecules, and preferably the PCR reagents comprise at least dATP, dCTP, dGTP and dTTP. In some cases, the PCR reagents also comprise dUTP.

The nucleic acid polymerase may be any enzyme capable of catalysing template-dependent polymerisation of nucleotides, i.e. replication. The nucleic acid polymerase should tolerate the temperatures used for the PCR amplification, and it should have catalytic activity at the elongation temperature. Several thermostable nucleic acid polymerases are known to the skilled person.

In some embodiments of the invention, the nucleic acid polymerase has 5'-3' nuclease activity and can thus be used in the amplification reaction with a TaqMan® probe.

The nucleic acid polymerase may be Escherichia coli DNA polymerase I. The nucleic acid polymerase may also be Taq DNA polymerase, which has a DNA synthesis-dependent strand replacing 5'-3' exonuclease activity. Other polymerases having 5'-3' nuclease activity include, but are not limited to, rTth DNA polymerase. The Taq DNA polymerase, e.g. obtained from New England Biolabs, can include Crimon LongAmp® Taq DNA polymerase, Crimson Taq DNA Polymerase, Hemo KlenTaq™, or LongAmp® Taq.

In some cases, the nucleic acid polymerase can be, e.g. E. coli DNA polymerase, Klenow fragment of E. coli DNA polymerase I, T7 DNA polymerase, T4 DNA polymerase, Taq polymerase, Pfu DNA polymerase, Vent DNA polymerase, bacteriophage 29, REDTaq™, Genomic DNA polymerase, or Sequenase. DNA polymerases are described, e.g. in U.S. Patent Application Publication No. 20120258501.

In addition, the PCR reagents may comprise salts, buffers and detection means. The buffer may be any useful buffer, e.g. TRIS. The salt may be any useful salt, e.g. potassium chloride, magnesium chloride or magnesium acetate or magnesium sulphate.

The PCR reagents may comprise a non-specific blocking agent, such as BSA, gelatin from bovine skin, beta-lactoglobulin, casein, dry milk, salmon sperm DNA or other common blocking agents.

The PCR reagents may also comprise bio-preservatives (e.g. $NaN_3$), PCR enhancers (e.g. betaine, trehalose, etc.) and inhibitors (e.g. RNase inhibitors). Other additives can include dimethyl sulfoxide (DMSO), glycerol, betaine (mono)-hydrate, trehalose, 7-deaza-2'-deoxyguanosine triphosphate (7-deaza-2'-dGTP), bovine serum albumin (BSA), formamide (methanamide), tetramethylammonium chloride (TMAC), other tetraalkylammonium derivaties [e.g. tetraethyammonium chloride (TEA-Cl)]; tetrapropylammonium chloride (TPrA-Cl) or non-ionic detergent, e.g. Triton X-100, Tween 20, Nonidet P-40 (NP-40) or PREX-CEL-Q.

Furthermore, the PCR reagents may also comprise one or more means for detection of PCR amplification product(s) comprising the mutation(s) in the NOI(s). Said means may be any detectable means, and they may be added as individual compounds or be associated with, or even covalently linked to, one of the primers. Detectable means include, but are not limited to, dyes, radioactive compounds, bioluminescent and fluorescent compounds. In a preferred embodiment, the means for detection is one or more probes. Thus, it is preferred that the PCR reagent comprises one or more detection probes, for example any of the probes described herein below in the section "Detecting PCR product(s)".

Primers Flanking the Target Sequence

The methods of the invention involve the use of one or more primer set(s) that flank the target sequence. A discrete "set of primers" that flanks a target sequence includes one primer comprising a sequence identical to the 5' end of the target sequence (also referred to as "forward primer"), and one primer comprising a sequence complementary to the 3' end of the target sequence (also referred to as "reverse primer"). The primer set is capable of amplifying the target sequence when added to a PCR together with a nucleic acid comprising the target sequence and PCR reagents under conditions allowing amplification of said target sequence. The same primer set may be used for all PCR amplifications of the methods according to the invention, even though it is also possible that different sets of primers are used for the PCR amplifications of the different steps of the invention.

In addition to the sequence identical to the 5' end of the target sequence, the forward primer may comprise additional sequences. Similarly, in addition to the sequence complementary to the 3' end of the target sequence, the reverse primer may comprise additional sequences. For example, the primers can at the 5' end contain an additional nucleic acid sequence, which does not hybridize to a target nucleic acid, but which facilitates handling of the primer or the PCR amplification product, e.g. detection of said product.

The length of the forward primer and the reverse primer can depend on the sequence of the target sequence. For example, the length of the primers can be adjusted to achieve a desirable melting temperature, $T_m$, of the primers. Thus, the length of the forward primer and reverse primer can, individually, be in the range of 10 to 100 nucleotides, for example in the range of 10 to 50 nucleotides, such as in the range of 15 to 20 nucleotides, such as in the range of 15 to 25 nucleotides, such as in the range of 15 to 30 nucleotides, such as in the range of 15 to 40 nucleotides, such as in the range of 15 to 45 nucleotides, such as in the range of 15 to 50 nucleotides in length. $T_m$ of the forward primer and the reverse primer is typically adjusted to in the range of 40 to 70° C.

Primer concentration within the aqueous phase of the PCR amplifications can, for example, be in the range of 0.05 to 2.0 µM, such as in the range of 0.1 to 1.0 µM, such as in the range of 0.2 to 1.0 µM, such as in the range of 0.3 to 1.0 µM, such as in the range of 0.4 to 1.0 µM or in the range of 0.5 to 1.0 µM.

The forward primer and reverse primer in general, comprise—or even consist—of oligonucleotides. However, in some cases, the primers may comprise nucleotide analogues. Numerous nucleotide analogues are known to the skilled person and include derivatives, wherein a sugar is modified, as in 2'-O-methyl, 2'-deoxy-2'-fluoro, and 2',3'-dideoxynucleoside derivatives, nucleic acid analogues based on other sugar backbones, such as threose, locked nucleic acids (LNA), LNA derivatives, peptide nucleic acids (PNA), glycol nucleic acid (GNA), threose nucleic acid (TNA), bicyclo sugars, or hexose, glycerol and glycol sugars, nucleic acid analogues based on non-ionic backbones, or nucleic acids and their analogues in non-linear topologies, such as dendrimers, comb-structures, and nanostructures.

The primers may also be linked to various tags (e.g. fluorescent tags, functionalized tags or binding tags), which can optionally be bound to their ends, sugars, or nucleobases.

Primers can be prepared by a variety of methods, including—but not limited to—cloning of appropriate sequences and direct chemical synthesis using methods well known in the art [Narang et al., Methods Enzymol. 68:90 (1979); Brown et al., Methods Enzymol. 68:109 (1979)]. Primers can also be obtained from commercial sources.

The forward primer and reverse primer can have an identical melting temperature or a similar melting temperature, e.g. a melting temperature of ±5° C. The lengths of the primers can be extended or shortened at the 5' and/or 3' end(s) to produce a primer set with the desired melting temperatures. Accordingly, one of the primers of a primer pair can be longer than the other primer.

Primers may be designed based on melting temperature. An equation for determining the melting temperature of primers smaller than 25 bp is known as the Wallace Rule [$T_d=2\times(A+T)+4\times(G+C)$]. Here, $T_d$ is the temperature at a particular salt concentration at which 50% of an oligonucleotide and its perfect filter-bound complement are in duplex conformation. Typically, $T_d$ is determined in 0.9 M NaCl. However, other considerations are also relevant when designing a primer, e.g. its predicted secondary structure. Several computer programs and on-line services are available for the design of primers.

In one embodiment, the set of primers may be designed in a manner, wherein the primers specifically are capable of amplification of the target sequence comprising the mutation in the NOI, but are not capable of amplifying the target sequence comprising the reference NOI. This may, for example, be achieved by designing the forward primer to comprise a sequence identical to the NOI(s) comprising the mutation(s), and/or it may be done by designing the reverse primer so that it comprises one or more sequences complementary to the NOI comprising the mutation(s).

In other embodiments, the set of primers may be designed in manners, wherein the primers specifically are capable of amplification of the target sequence comprising the reference NOI, but are not capable of amplifying the target sequence comprising the mutation(s) in the NOI(s). This may, for example, be achieved by designing the forward primer such that it comprises a sequence identical to the reference NOI, and/or by designing the reverse primer that comprises a sequence complementary to the reference NOI.

However, in some embodiments of the invention, the sets of primers are capable of amplifying both the target sequence that comprise the mutation(s) in the NOI(s), and the target sequence comprising the reference NOI.

It is notable that the methods of the invention comprise PCR amplifications with more than one set of primers, e.g. 2 sets of primers, such as 3 sets of primers, for example in the range of 2 to 10 sets of primers. Thus, each PCR amplification may comprise several sets of primers flanking different target sequences. This allows detection of more than one different mutation during one PCR amplification.

In embodiments where the PCR is an rhPCR, the PCR reaction is preferably performed in the presence of blocked primers containing a single ribonucleotide residue. Such blocked primers are activated by enzymatic cleavage by RNase HE2 following perfect hybridization to the target DNA. Cleavage occurs on the 5' side of the RNA base, thus releasing the RNA base together with the 3' blocking moiety, permitting selective amplification of target DNA fragments. A tail sequence can be incorporated into the amplicon to combine the use of a 5'-nuclease assay based reporter system with rhPCR.

Detecting PCR Product(s)

In some embodiments, the methods of the invention comprise the step of detecting PCR amplification product(s) comprising target sequence(s) that comprise mutation(s) in NOI(s) of interest. The PCR amplification product(s) may be detected by any useful means.

As described above, said mutation(s) may be substitution(s), deletion(s) and/or insertion(s), involving from only one or a few nucleotide(s) to a large number of nucleotide(s). Thus, the detection may be adapted to the particular mutation specified by the NOI.

In some embodiments, the set of primers are designed in a manner, wherein the primers specifically are capable of amplifying of the target sequence comprising the mutation(s) in the NOI(s), but are not capable of amplification of the target sequence comprising the reference NOI. In other embodiments, the set of primers may be designed in a manner, wherein these specifically are capable of amplifying the target sequence comprising the reference NOI, but not the target sequence comprising the mutation(s) in the NOI(s). In such embodiments, the detection may simply be based on detecting the presence or absence of a PCR amplification product. This may, in particular, be the case in embodiments of the invention, wherein the mutation is a mutation of a larger number of NOIs.

In preferred embodiments, the PCR amplification products are detected with the aid of detection probe(s). This may, in particular, be the case when the mutation(s) is mutation of a smaller number of NOI(s), for example one or more point mutations.

The detection probe may be an oligonucleotide comprising a sequence that is identical to the NOI comprising the mutation. In addition, said probe usually also comprises sequences identical to the regions of the target sequence that flank the NOI. Similarly, the detection probe may be an oligonucleotide comprising a sequence that is complementary to the NOI comprising the mutation, and in addition said probe may also comprise sequences complementary to the regions of the target sequence flanking the NOI. Said regions flanking the NOI may be the sequence(s) immediately 5' and/or 3' of the NOI(s), respectively. Such probes will preferably anneal to PCR amplification products comprising the mutation in the NOI, but not to PCR amplification products comprising the reference NOI. Such detection probes are also referred to as "mutant detection probes" herein. The mutant detection probe typically comprises in the range of 10 to 30 nucleotides. In particular, the mutant detection probe may comprise a consecutive sequence of in the range of 10 to 30 nucleotides identical, or complementary, to the target sequence comprising the mutation in the NOI.

The detection probe may also be an oligonucleotide comprising a sequence that is identical to the reference NOI. In addition, said probe usually also comprises sequences identical to the regions of the target sequence flanking the NOI. Similarly, the detection probe may be an oligonucleotide comprising a sequence that is complementary to the reference NOI, and said probe may in addition also comprise sequences complementary to the regions of the target sequence flanking the NOI. Such probes will preferably anneal to PCR amplification products comprising the reference NOI, but not to these amplification products comprising the mutation in the NOI. Such detection probes are also referred to as "reference detection probes" herein. The reference detection probe typically comprises in the range of 10 to 30 nucleotides. In particular, the reference detection probe may comprise a consecutive sequence of in the range of 10 to 30 nucleotides identical to, or complementary to, the target sequence comprising the reference NOI.

In some embodiments, the PCR reagents comprise a set of probes consisting of a mutant detection probe and a reference detection probe. The "set of probes" is preferably capable of competing for the binding site(s) at the NOI(s) when added to a PCR amplification together with a nucleic acid comprising the target sequence, PCR reagents and the set of primers under conditions allowing amplification of said target sequence. As noted above, the detection probes are typically oligonucleotides. In particular, they may be short nucleotide stretches of single-stranded DNA. The detection probes may be associated with, or even covalently linked to detectable means—including, but not limited to, reporters, dyes, radioactive compounds, bioluminescent compounds, fluorescent compounds and fluorophore/quencher pairs.

In some embodiments the most 5' nucleotide of the detection probe is not a G. Thus, the mutation detection probe may comprise an oligonucleotide, wherein the most 5' nucleotide is not a G. Similarly, the reference detection probe may comprise an oligonucleotide, wherein the most 5' nucleotide is not a G.

The methods of the invention may comprise use of both a mutant detection probe and a reference detection probe. In such cases, preferably, the probes are differentially labelled, e.g. such that one of the probes is associated with, or covalently linked to, detectable means, whereas the other is not. It is also possible that both probes are associated with, or covalently linked to, detectable means, wherein said detectable means are different.

In one embodiment, the reference detection probe is labelled with a fluorophore at the 5' end and with a quencher at the 3' end. Said fluorophore and quencher may, for example, be HEX and Black-Hole Quencher, respectively. In one embodiment, the mutant detection probe is labelled with a fluorophore at the 5' end and with a quencher on the 3' end. Said fluorophore and quencher may, for example, be FAM and Black-Hole Quencher, respectively.

The PCR reactions may comprise a similar amount of the mutant detection probe and the wild-type detection probe. However in some embodiments it may be preferred that an excess of mutant detection probe is employed. This may in particular be the case for detecting PCR product(s) after PCR amplification on a super-pool. In such cases, the PCR may reactions comprise at least 2-fold, more preferably at least 4-fold excess of the mutant detection probe compared to the reference detection probe.

In some embodiments, the detection probe is a TaqMan® probe (Heid et. al, 1996), which takes advantage of the 5' exonuclease activity of a nucleic acid polymerase. This is why the PCR reagents preferably comprise a nucleic acid polymerase with 5' exonuclease activity (e.g. Taq polymerase). Typically, the TaqMan® probe may be either a mutant detection probe, as described above, or a reference detection probe, as described above, covalently linked to a fluorophore/quencher pair. Thus, the probe may contain a fluorophore, usually at or near the 5' base. In addition, the TaqMan® probes may contain a quencher, which can be at or near the 3' base, and capable of quenching the fluorescence of said fluorophore Tyagi et al. (1998)]. When irradiated, the excited fluorophore transfers energy to the nearby quencher rather than fluorescing [Forster or fluorescence resonance energy transfer (FRET)]. Thus, a close proximity of the fluorophore and quencher can prevent emission of any fluorescence, while the probe is intact. However, when the TaqMan® probe anneals to an internal region of the target sequence and the polymerase replicates a template on which a TaqMan® probe is bound, its 5' exo-nuclease activity can cleave the probe. This series of events abolish the functionality of quenching, i.e. no FRET, and the fluorophore starts to emit fluorescence, which can be measured by any useful means.

Notably, as emphasized above, it is also comprised within the invention that the methods may be used for identifying more than one different mutation. This may be achieved by using a plurality of sets of primers as described above. However, this may also be achieved by using several different detection probes. Thus, in one embodiment, the methods may be used for identifying more than one different mutation within NOIs in the target sequence. In such embodiments, the PCR reagents may comprise a reference detection probe and several mutation detection probes, wherein each mutation detection probe comprises an oligonucleotide having a sequence identical to or complementary to one of the mutations. Preferably, the reference detection probe and the mutation detection probes are linked to different detection means. All the mutation detection probes may be linked to the same detection means, or to similar detection means or to different detection means.

In some cases, the detection probe is a molecular beacon (MB), i.e. a probe comprising complementary sequences capable of self-hybridisation (also referred to as "stem"), resulting in a "hairpin loop" structure. The loop of the MB can contain sequences complementary to, or identical to, the NOI(s), either mutant or reference NOI(s). Furthermore, the MB typically comprises a fluorophore and a quencher positioned at either end of the MB, so that they are proximal to one another, when the probe is hybridised to itself. The MB may be either a mutant detection probe as described above or a reference detection probe as described above covalently linked to a fluorophore/quencher pair, and to stem sequence(s) providing the complementary regions of the MB. Further details regarding standard methods of making and using MBs are well established in the literature and MBs are available from a number of commercial reagent sources.

In some cases, a primer/probe is used; in some cases, the primer/probe is a Scorpions™ probe, which can provide a FRET-based stem-loop detection mechanism similar to MB, except that the probe also has a segment attached that serves as either forward or reverse primer (Whitcombe et al. (1999); U.S. Pat. No. 6,326,145). A Scorpions™ probe can maintain a stem-loop configuration in the unhybridized state, with the fluorophore quenched. A Scorpions™ probe can have a longer multi-component structure, e.g. a 5' fluorophore, then a target-specific stem-loop section, then a quencher, then a blocker [e.g. hexethelene glycol (HEG)], and finally a 3' primer sequence. The blocker can prevent reverse extension of the product onto the probe.

In some cases, a primer/probe is a Sunrise™ probe, which comprises a primer attached to a hairpin probe that is extended during amplification. This arrangement can separate an internal quencher from a 5' terminal fluorophore (Nazarenko et al. (1997)).

The detection probe can be of any useful length, for example in the range of 10 to 60 nucleotides in length. The oligonucleotide probe can also be in the range of 10 to 30 nucleotides in length. The precise sequence and length of an oligonucleotide probe can depend in part on the nature of the target polynucleotide to which it binds. The binding location and length can be varied to achieve appropriate annealing and melting properties for a particular situation. For example, the detection probe may be designed to have a melting temperature in the same range as the forward primer and/or the reverse primer, e.g. within +10° C., such as within ±5° C.

The 3' terminal nucleotide of the detection probe(s) can be blocked or rendered incapable of extension by a nucleic acid polymerase. Such blocking can be conveniently carried out by the attachment of detectable means, either through a fluorophore or quencher to the terminal 3' base of the oligonucleotide probe by a linking moiety.

There is a great deal of practical guidance available in the literature describing useful fluorophore-quencher pairs, including methods for selecting fluorophore-quencher pairs, as exemplified herein below:

Clegg, Meth. Enzymol., 211: 353-388 (1992); Wo et al., Anal. Biochem., 218: 1-13 (1994); Pesce et al., editors, Fluorescence Spectroscopy (Marcel Dekker, New York, 1971); White et al., Fluorescence Analysis: A Practical Approach (Marcel Dekker, New York, 1970); and the like;

The literature also includes references providing exhaustive lists of fluorescent and chromogenic molecules and their relevant optical properties for choosing reporter-quencher pairs, e.g. Berlman, Handbook of Fluorescence Spectra of Aromatic Molecules, 2nd Edition (Academic Press, New York, 1971); Griffiths, Colour and Constitution of Organic Molecules (Academic Press, New York, 1976); Bishop, editor, Indicators (Pergamon Press, Oxford, 1972); Haugland, Handbook of Fluorescent Probes and Research Chemicals (Molecular Probes, Eugene, 1992) Pringsheim, Fluorescence and Phosphorescence (Interscience Publishers, New York, 1949); and the like.

Further, there is extensive guidance in the literature for derivatizing reporter and quencher molecules for covalent attachment via common reactive groups that can be added to an oligonucleotide, as exemplified by the following references: Haugland (cited above); Ullman et al., U.S. Pat. No. 3,996,345; Khanna et al., U.S. Pat. No. 4,351,760; and the like.

Fluorophores and quenchers can, for example, be selected from fluorescein and rhodamine dyes. These dyes, combined with appropriate linking methodologies for attachment to oligonucleotides are described in many references, e.g. Khanna et al. (cited above); Marshall, Histochemical J., 7:299-303 (1975); Menchen et al., U.S. Pat. No. 5,188,934; Menchen et al., European Patent Application 87310256.0; and Bergot et al., International Application PCT/US90/05565. The latter four documents are hereby incorporated by reference.

A fluorophore/quencher pair can use a fluorophore, such as EDANS or fluorescein, e.g. on the 5'-end and a quencher such as Dabcyl, e.g. at the 3'-end.

Detection of PCR amplification product(s) may involve a step of comparing the signal obtained in a PCR amplification comprising a given DNA sample with the signal obtained in a control PCR amplification. The signal may typically relate to the detectable means associated with a mutant detection probe and/or a wild-type detection probe. Thus, if said probes are associated with a fluorophore, the signal may be fluorescence. The control PCR amplification may be a PCR amplification performed under the same conditions, but lacking a DNA sample—i.e. said control PCR amplification may lack a DNA template, or it may contain only a control DNA comprising only the reference target sequence, e.g.

wild-type DNA. In some embodiments, any signal which is stronger than the signal from the control PCR amplification may be considered a positive signal, i.e. a signal indicating the presence of a target sequence comprising one or more mutations in the NOI.

In one embodiment any signal which is above a given threshold may be considered a positive signal. The threshold can be determined by any useful manner, typically by using a suitable software, e.g. the QX200™ Droplet Reader and Quantasoft™ Software available from Biorad.

In embodiments of the invention, wherein mutation detection reference detection probes are employed, the fractional abundance between the signal obtained from the mutation detection probe and that of the reference detection probe may be determined, and used to assess the presence of a PCR product. The fractional abundance may be determined as: [Signal of ("mutant detection probe")] divided by [Signals of ("reference detection probe"+"mutant detection probe")].

A sample may, for example, be assumed to contain target DNA comprising the mutation in the NOI, provided that it in a comparison with a control PCR amplification is characterized by:

1) An increased fractional abundance, and/or;
2) Increased concentration of mutant droplets, and/or;
3) Increased number of mutant events at a scale of 50% or higher above average.

Mutant droplets may be droplets giving a positive signal from the mutant detection probe. Herein, "mutant event" equals the number of mutant droplets.

Identifying Microorganisms or Regenerative Parts within a Sub-Pool

Once a sub-pool comprising microorganisms or regenerative parts with the DNA comprising the mutation(s) of interest has been identified, the methods in general comprise a step of identifying microorganisms or regenerative parts within said sub-pool comprising said mutation.

This may be done in any conventional way. If the sub-pool is sufficiently small, this may simply be done by testing each seed or progeny thereof within said sub-pool for the presence of the mutation. For example, a sample may be taken from each regenerative part or each regenerative part may be grown into a plant, and a sample from said plant may be used for detecting, whether said plant carries the mutation. If the sub-pool contains microorganisms, this may be done by clonal expansion of each microorganism in the sub-pool, and subsequent identification of a clone comprising the mutation.

Frequently, however, less labor intensive methods for identifying microorganisms or regenerative parts within a sub-pool carrying the mutation may be employed. For example, the sub-pool may be divided into secondary sub-pools, and secondary sub-pool(s) comprising microorganisms or regenerative parts with the DNA comprising the mutation(s) of interest may be identified. This may be done essentially in the same manner as described herein above for identification of a sub-pool comprising a regenerative part of interest. However, since the secondary sub-pool typically is significantly smaller than the initial sub-pool, less sensitive methods may also be employed.

In one embodiment regenerative parts of interest are identified by a method comprising the steps of Providing a sub-pool comprising a plurality of regenerative parts of a plant, wherein said sub-pool comprises regenerative part(s) comprising one or several mutation(s) of the NOI(s);
Dividing the regenerative parts of said sub-pool into secondary sub-pools;
Obtaining a sample from each regenerative part of the secondary sub-pools—in a manner leaving the regenerative parts sufficiently intact to develop into a plant—and combining all samples from all regenerative parts of each secondary sub-pool;
Preparing a DNA sample from said combined samples;
Identifying secondary sub-pool(s) comprising DNA comprising the mutation(s)
Identifying regenerative part(s) within said secondary sub-pool comprising said mutation.

In one embodiment the step of identifying regenerative parts within said secondary sub-pool comprising said mutation involves testing each regenerative part such as each seed or progeny thereof within said secondary sub-pool for the presence of the mutation. For example, each regenerative part may be grown into a plant, and a sample from said plant may be used to detect whether said plant carries the mutation.

In one embodiment microorganisms of interest are identified by a method comprising the steps of Providing a sub-pool comprising a plurality of microorganisms, wherein said sub-pool comprises microorganism(s) comprising one or several mutation(s) of the NOI(s);
Dividing the microorganisms of said sub-pool into secondary sub-pools;
Subjecting each secondary sub-pool to a step of reproduction in a clonal manner thereby obtaining clones of each microorganism contained in the secondary sub-pool,
Obtaining a sample from a fraction of each clone, wherein the remainder of each clone is capable of reproduction;
Preparing a DNA samples from either each fraction of each clone individually or combining said samples and preparing DNA samples from said combined samples;
Identifying secondary sub-pool(s) comprising DNA comprising the mutation(s)
Identifying clones within said secondary sub-pool comprising said mutation.

In one embodiment microorganisms of interest are identified by a method comprising the steps of Providing a sub-pool comprising a plurality of microorganisms, wherein said sub-pool comprises microorganism(s) comprising one or several mutation(s) of the NOI(s);
Dividing the microorganisms of said sub-pool into secondary sub-pools;
Subjecting each secondary sub-pool to a step of reproduction so that each sub-pool in theory comprises more than one microorganisms of each genotype,
dividing each secondary sub-pool into fractions, wherein at least two fractions each in theory comprise microorganisms of each genotype of the secondary sub-pool,
preparing DNA samples, such as cDNA samples prepared from mRNA samples or gDNA samples, from an entire fraction of said secondary sub-pool;
identifying secondary sub-pool(s) comprising DNA comprising the mutation(s).

If needed above mentioned procedure may be repeated by dividing secondary sub-pools comprising the microorganism of interest into further sub-pools.

Once a secondary or further sub-pool comprising microorganisms carrying a mutation in the NOI, the individual microorganism carrying the mutation in the NOI may be identified as outlined below. Alternatively, the individual microorganism carrying the mutation in the NOI may be identified directly from the sub-pool omitting the step of generating secondary sub-pools.

Regardless of whether the microorganism carrying the mutation in the NOI is identified from a sub-pool or from a secondary or further sub-pool, this may for example be done as follows:

Providing a sub-pool or a secondary sub-pool or a further sub-pool comprising a plurality of microorganisms, wherein said sub-pool comprises microorganism(s) comprising one or several mutation(s) of the NOI(s);

Reproducing the microorganisms of said sub-pool or secondary sub-pool or further sub-pool in a clonal manner, thereby preferably obtaining clones of each microorganism, Obtaining a sample from a fraction of each clone, wherein the remainder of each clone is capable of reproduction;

Preparing a DNA sample from said samples,

Identifying sub-pool(s), secondary sub-pools or further sub-pools comprising DNA comprising the mutation(s)

Identifying clones comprising said mutation.

Plant Phenotype and Altered Trait(s)

The present methods allow using the best cultivars and most advanced breeding lines for library construction. This ensures that the desired traits are introduced into a desirable background, e.g. of region-adapted, high-yielding, climate-resilient and/or disease-resistant breeding stock. As explained above, the present methods reduce or eliminate the necessity for backcrossing. The present methods are based on random mutagenesis. In contrast, GM or gene-editing technologies generally require a transformation step and are therefore limited to species that can be transformed, or to non-elite, transformable varieties that grow vigorously in tissue culture but are poorly adapted to the local environment.

The term phenotype of a plant is a term used to describe observational characteristics, such as height, yield, grains size, leaf shape, biomass etc. of the plant. The phenotype of a plant is normally determined as the collective expression of the genotype of the plant, in combination with the environmental effect on the plant's observational characteristics.

In some cases, plants of the same genotype interacting with the environment may manifest different phenotypes. In other cases, plants may have the same phenotype but different genotypes.

After mutagenesis and selection of a plant with a specific desired mutation, the mutant plant of the present invention has a different genotype compared to the parent plant. In particular, the mutant plant comprises 1 to 30 non-synonymous mutations in coding regions as detailed herein above.

In one embodiment, the mutant plant and the parent plant may have the same phenotype. In another embodiment, the plants have different phenotypes. It is preferred that the mutant plant has the same observational characteristics as the parent plant, except for the characteristic/trait caused by the mutation(s) in the NOI(s). In other words, it is preferred that the mutagenized plant has the same phenotype as the parent plant, except from the desired mutagenized trait.

Thus, the mutation(s) results in one or more specific trait(s), which will preferably be the only trait that differs between the mutant plant and the plant of generation M0 (i.e. prior to mutagenesis). This is possible due to the low mutagenesis rates used in the present methods.

In some embodiments, one or more of the appearance, height, biomass, leaf shape and taste of the mutant plant is the same as in the parent plant, preferably all of the appearance, height, biomass, yield, grain size, leaf shape and taste of the mutant plant are the same as in the parent plant.

Yield, Grain Quality, Sterility and Other Traits

High mutagenesis rate often leads to a plant with a yield penalty. Since the present methods are based on low mutagenesis rates, as described herein above, mutagenized plants having a similar yield as the parent plant can be obtained. The mutant plant may in particular produce a yield which is at least 90%, such as at least 91%, such as at least 92%, such as at least 93%, such as at least 94%, such as at least 95%, such as at least 96%, such as at least 97%, such as at least 98%, such as at least 99%, or such as 100% of the total (crop) yield of the parent plant, or more. In some embodiments, the mutant plant may have a yield which is higher than the total yield of the parent plant. Thus in some embodiments, the mutant plant may produce a yield which is 105% of the total yield of the parent plant or more, such as 110% or more, such as 120% or more, such as 130% or more, such as 140% or more, such as 150% or more, such as 175% or more, such as 200% or more.

In another embodiment of the invention, the NOI is predetermined to affect the yield of the mutant plant, thus in this embodiment the yield of the mutant plant will be altered compared to the yield of the parent plant. In a preferred embodiment the yield of the mutant plant is at least the same as or greater than the yield of the parent plant. Since yield may vary depending on the growth conditions or nature of the soil, the yields of the mutant plant and of the parent plant should preferably be compared for plants growing under similar conditions.

The mutant plants obtained by the present methods preferably have a grain quality which is substantially the same as or greater than the grain quality of the parent plant.

Thus in some embodiments, the mutation of interest is not detrimental to grain quality. Accordingly, one or more of the moisture content of the grain, the test weight, the percentage of discolored, broken or damage kernels, the breakability of the grain, the milling quality, the protein and oil content, and the viability of the grain, are the same as or greater than the corresponding features in the parent plant. Also, one or more of grain color, composition, bulk density, odor and aroma, size and shape are preferably the same as or better than the corresponding features in the parent plant.

Preferably, the desired mutations do not, or only moderately, increase sterility of the plants. Thus in some embodiments the mutant plants obtained by the present methods, i.e. the percentage of sterile flowers per spike, have a sterility below 30%.

Microorganism Phenotype and Altered Trait(s)

The present methods allow targeted modification of naturally occurring microorganisms and/or elite microorganisms with beneficial properties. This ensures that the desired traits are introduced into a desirable background. As explained above, the present methods reduce or eliminate the necessity for backcrossing, which is highly desirable in prokaryotes and in other species of microorganisms that mainly reproduce asexually.

The present methods are based on random mutagenesis. In contrast, GM or gene-editing technologies generally require a transformation step, which is often undesirable and for some species also technically challenging.

The term phenotype of a microorganism is a term used to describe observational characteristics, such as size, shape, growth characteristics, metabolism etc. The phenotype is normally determined as the collective expression of the genotype of the microorganism, in combination with the environmental effect.

After mutagenesis and selection of a microorganism with a specific desired mutation, the mutant microorganism of the present invention has a different genotype compared to the parent. In particular, the mutant microorganism comprises 1 to 30 non-synonymous mutations in coding regions as detailed herein above.

In one embodiment, the mutant microorganism and the parent microorganism may have the same phenotype. In another embodiment, the microorganisms have different phenotypes. It is preferred that the mutant microorganism has the same observational characteristics as the parent microorganism, except for the characteristic/trait caused by the mutation(s) in the NOI(s).

EXAMPLES

Example 1—Low Mutation Density Protocol

To induce mutations, kernels collected from barley plants were incubated in a solution with the mutagen sodium azide (NaN$_3$), according to the details provided by both Kleinhofs et al. (1978) and those provided in U.S. Pat. No. 7,838,053 with the following changes: The concentration of sodium azide used for the mutagenizes was reduced to 0.3 mM for 2 hours.

This procedure induces point mutations in the barley grains' genomic DNA (gDNA), typically conferring randomly distributed codons for amino acid substitutions or translational stops of the protein-encoding DNA, i.e. leading to protein changes and truncations in proteins encoded by the mutagenized DNA, respectively. However, the methods of the invention also are useful for producing cereal plants with point mutations in the gDNA of non-protein coding regions, e.g. promoters, terminators and introns.

15 kg of grains were mutagenized and planted in 30 plots of 7.5 m$^2$ each. The plots were then divided into 17 sub-plots, each corresponding to a sub-pool, from which seed banks and DNA samples were generated.

Example 2—RNase H2-Dependent PCR (rhPCR) to Detect Mutant(s) in a Mutant Library RNase H2-dependent PCR (rhPCR) (Dobosy et al., 2011) can improve the specificity of a PCR amplification by utilizing so called 'blocked primers'. These primers contain a single ribonucleotide residue and a 3'-blocking moiety, which prevents extension of the primer during the PCR. The primers may, however, be activated by RNase H2, which then allows them to be extended during the PCR amplification. RNase H2 cleavage will only occur if the blocked primer binds to a perfect match. Even a mismatch of only a nucleotide change can inhibit cleavage significantly. This means that blocked primers can be designed to specifically block the amplification of unspecific or undesired amplicons, thus providing a very sensitive tool to detect rare, specific nucleotide substitutions. A fluorophore labeled probe, complementary to the 5'-end of the rhPCR primer, enables the quantification of successful primer extension during rhPCR of a specific amplicon.

A unique rhPCR assay is designed (rhAmp® SNP Genotyping System, Integrated DNA Technologies) to distinguish between a mutant allele and wild-type allele of a *Hordeum vulgare* gene. The rhPCR mutant detection primer is complementary to the coding sequence including the NOI. The rhPCR reference detection primer is complementary to the coding sequence. The rhPCR reference and mutation detection primer are additionally labelled, e.g. with the fluorophore FAM and Yakima Yellow, respectively.

This assay is used to screen a library of sub-pools originating from a pool of M2 individuals. Purified gDNA is added to a PCR mixture containing the required reagents. Samples are thermally cycled using standard PCR conditions. Reaction products are quantified on a fluorescence reader.

The data from the fluorescence reader is analyzed by comparing the average fluorescence signal of all screened sub-pools with the fluorescence signal of individual sub-pools. A positive sub-pool is considered a candidate when the individual fluorescence signal is at least 2-fold higher than the average fluorescence signal of all sub-pools.

Sub-pools showing a fluorescence higher than the average fluorescence signal are considered to contain a mutant. To confirm the presence of a mutant in a sub-pool, a fraction of said sub-pool is subjected to a non-destructive DNA isolation. Here tissue samples from individual barley grains are removed and subjected to DNA analysis in pools. Each of these DNA pools is analysed with the same rhPCR assay as described above. DNA pools having a fluorescence signal at least 2-fold higher than the average fluorescence signal for the remaining DNA pools are identified. The mutation signal in those pools confirms the presence of the desired mutant.

Example 3—Direct Sequencing of Low Mutagenized Barley Plants

We have sequenced a library of 6000 barley plants (cv. Quench). The grains were mutated using 0.3 mM sodium azide for 2 hours. A library was constructed consisting of 6000 individual M3 spikes. One grain per spike was utilized for DNA extraction.

We have amplified a 790 bp fragment of a gene of interest in order to analyse 645 bp of exon 3 of that gene. Amplicons for all 6000 lines were analysed for polymorphisms. We have identified 3 individual mutants within the 645 bp for the 6000 lines. That corresponds to 3/(645×6000)=1 mutant in every 1.29 million bp corresponding to about 24 non-synonymous mutations in coding regions.

The three mutants corresponded to the following mutation sites:
1. Nucleotide G989>A (cDNA) corresponding to amino acid change S330>N (protein)
2. Nucleotide C1091>T (cDNA) corresponding to amino acid change P364>L (protein)
3. Nucleotide C858>T (cDNA) did not cause an amino acid change We have amplified a 860 bp fragment of the gene AAP3 (HvAAP3) in order to analyse 648 bp of exon 6 of that gene. Amplicons for all 6000 lines were analysed for polymorphisms. We have identified 3 individual mutants within the 648 bp for the 6000 lines. That corresponds to 1 mutant in every 1.296 million bp corresponding to about 24 non-synonymous mutations in coding regions, which correspond to 99.94% genes being free of non-synonymous mutations.

The three mutants corresponded to the following mutation sites:
4. Nucleotide C982>T (cDNA) corresponding to amino acid change H328>Y (protein)
5. Nucleotide G820>A (cDNA) corresponding to amino acid change A274>T (protein)
6. Nucleotide C851>T (cDNA) corresponding to amino acid change A284>V (protein)

Example 4—Screening for Barley Mutants with a Premature Stop in Amino Acid Permease 3 (HvAAP3)

Mutagenesis of barley cv. Planet was performed as described in Example 1 to reach a mutation density of about 1 mutation in 1.3 million bp, corresponding to about 24 non-synonymous mutations in coding regions, corresponding to 99.94% genes being free of non-synonymous mutations.

With reference to Example 6 below, the optimal library size is approx. 520.000, if a probability of success of >94% is desired and 7 different mutations are searched for. Thus, the optimal number of regenerative parts to cultivate is 99.640 if calculated according to Example 7 below.

Screening was performed using a ddPCR protocol having a detection sensitivity of 1 in 2000, Barley has a GECN number of 5-6. On this basis the theoretical maximal sub-pool size calculated as outlined in Example 8 below was 363.

Thus, a library of 374 sub-pools was screened originating from a pool of 110,000 plants to identify one positive sub-pool. Thus, each sub-pool contained grains of generation M1 from approx. 294 plants. A fraction of the positive sub-pool was then screened again to identify the mutant grain. Screening was performed with ddPCR as described in PCT/EP2017/065516. The mutation searched for was a stop codon, and accordingly 7 different mutations were acceptable. One of the desired mutants has a nucleotide change at position 820 from guanine to adenine of the coding sequence of HvAAP3, which is available under HORVU.MOREX.r2.7HG0553990.1 on the IPK Barley Blast Server by the International Barley Sequencing Consortium (29 Sep. 2019), that causes an amino acid change at position 274 that leads to an amino acid change from alanine to threonine in the protein sequence, which is available under HORVU.MOREX.r2.7HG0553990.1 on the IPK Barley Blast Server by the International Barley Sequencing Consortium (29 Sep. 2019). In order to identify the mutant, a target specific forward primer (CCGGCCGAGAACAAG (SEQ ID NO: 1)), a target-specific reverse primer (CGTGGTGGTGGAGAC (SEQ ID NO: 2)), a mutant-specific detection probe (AGGAAGACAAACCTACTGG (SEQ ID NO: 3)) labelled with 6-carboxyfluorescein (FAM) and a reference-specific detection probe (AGGAAGGCAAACCTACTG (SEQ ID NO: 4)) labelled with hexachlorofluorescein (HEX) were designed.

Example 5—Screening for Barley Mutants with a Premature Stop in the Glycine-Rich RNA-Binding Protein (HvGR-RBP1)

Mutagenesis of barley cv. Paustian was performed as described in example 1 to reach a mutation rate of about 1 mutation in 1.3 million bp, corresponding to about 25 non-synonymous mutations in coding regions. We screened a library of 374 sub-pools originating from a pool of 110,000 M1 individuals to identify one positive sub-pool. A sub-fraction of the positive sub-pool was then screened again to identify the mutant grain. Screening was performed with ddPCR as described in WO 2018/001884, using primers and probes designed specifically for the identification of the desired mutant at the HvGR-RBP1 locus.

The mutation corresponded to the following mutation site: Nucleotide G54>A (cDNA) corresponding to amino acid change W18 (protein).

Mutagenesis of barley cv. Planet was performed as described in Example 1 to reach a mutation density of about 1 mutation in 1.3 million bp, corresponding to about 24 non-synonymous mutations in coding regions, corresponding to 99.94% genes being free of non-synonymous mutations.

With reference to Example 6 below, the optimal library size is 520.620, if a probability of success of >33% is desired and one mutation is searched for. Thus, the optimal number of regenerative parts to start with is 99.640 if calculated according to Example 7 below.

Screening was performed using a ddPCR protocol having a detection sensitivity of 1 in 2000, Barley has a GECN number of 5-6. On this basis the maximal sub-pool size calculated as outlined in Example 8 below was 363.

Thus, a library of 374 sub-pools was screened originating from a pool of 110,000 plants to identify one positive sub-pool. Thus, each sub-pool contained grains of generation M1 from approx. 294 M1 plants. A fraction of the positive sub-pool was then screened again to identify the mutant grain. Screening was performed with ddPCR as described in PCT/EP2017/065516. The desired mutant has a nucleotide change at position 54 from guanine to adenine of the coding sequence of HvGR-RBP1, which is available under HORVU.MOREX.r2.6HG0491380.1 on the IPK Barley Blast Server by the International Barley Sequencing Consortium (29 Sep. 2019), that causes an amino acid change at position 18 that leads to a premature stop in the protein sequence, which is available under HORVU.MOREX.r2.6HG0491380.1 on the IPK Barley Blast Server by the International Barley Sequencing Consortium (29 Sep. 2019). In order to identify the mutant, a target specific forward primer (CGCTGCTTCGTCGG (SEQ ID NO: 5)), a target-specific reverse primer (GAGCTAAAAGCAGCCTC (SEQ ID NO: 6)), a mutant-specific detection probe (CTGTCCTGAAACACCGA (SEQ ID NO: 7)) labelled with 6-carboxyfluorescein (FAM) and a reference-specific detection probe (CTGTCCTGGAACACCG (SEQ ID NO: 8)) labelled with hexachlorofluorescein (HEX) were designed.

Example 6

Determining Optimal Library Size

In order to enhance the probability of success in identifying a mutant of interest, various factors may be considered. First of all the size of the library size may be optimized. The optimal library size (OLS) is dependent on a number of factors. If the desired mutation is a translational stop mutant, several potential codons can be targeted. This means that a smaller library can translate into a higher probability of success. If the desired mutation is a specific nucleotide change or a codon for an amino acid change, then only one, sometimes few, event(s) will give the desired outcome, and a larger library is preferable to enhance the probability of success.

In general, the optimal library size preferably reflects the total amount of mutated genomes that need to be screened in order to identify at least one desired mutant. The probability of identifying a specific mutation in a certain library of mutated genomes can be calculated using the mutation frequency ($M_f$). If several mutations are screened for simultaneously (e.g. if there are several potential stop codons, which are equally desirable), then the probability increases. The number of mutations screened for is also referred to as n herein.

The probability to identify at least one desired mutation using a library of library size LS and a mutation frequency Mf can thus be calculated as:

$$PS = 1 - Mf^{LS}$$

By way of example, in a library of M1 seeds from 1.000.000 mutagenized rapeseed plants (each with a mutation frequency of ⅟500 kbp) there is a probability of 0.86 to identify at least one a specific nucleotide at a targeted locus as calculated below:

$$PS = 1 - (499999/500000)^{1000000} = 0.86$$

This formula can also be used to determine the optimal size of a library required in order to achieve a certain probability. The optimal library size is equal to the maximum size of the library, which in the example above is equal to 1.000.000 unique genomes.

Thus, the optimal library size can be calculated as follows:

$$\text{Optimal library size } (OLS) = \frac{\log\left(1 - \frac{PS}{100}\right)}{\log(1 - (1 - (1 - (Mf \times n))))}$$

wherein
OLS is the optimal library size;
PS is the probability of success in %
Mf is the mutation frequency and
n is the number of mutations screened for.

By way of example, at least one specific nucleotide change in a library of plants each with a mutation frequency of ⅟500 kbp can be identified with a probability of 95%, if the library equals 1.497.864 mutated genomes.

Optimal library size $(OLS) =$ $$\frac{\log\left(1 - \frac{PS}{100}\right)}{\log(1 - (1 - (1 - (1/500000 \times 1))))} = 1.497.864$$

The mutation frequency can be determined using the total number of nucleotides screened in a genome and the total number of genetic variants identified among the number of nucleotides screened. Thus, the mutation frequency can be calculated as:

$$Mf = \frac{Nnc}{Nna}$$

wherein
$N_{nc}$ is the total number of nucleotide changes
$N_{na}$ is the number of nucleotides analysed.

By way of example, if one analyses 1,000,000 nucleotides in a mutated genome and non-mutated genome, and identifies 2 nucleotides that differ among them, then the mutation frequency is one in 500,000.

$$Mf = \frac{2}{1,000,000} = \frac{1}{500,000}$$

Example 7

Determining the Optimal Number of Regenerative Parts (Np) to Start with

The optimal library size may be determined as described in Example 1.

The optimal number of regenerative parts (ONp) to be subjected to random mutagenesis for the methods of the invention may then be determined. In other words, ONp is equal to the optimal number of regenerative parts (e.g. seeds) to be mutated in order to achieved a predetermined probability of success. The optimal ONp can be calculated utilizing the optimal library size, the number of germline cells (GECN) and the germination rate of the material as follows:

$$ONp = \frac{\frac{OLS \times 100}{Gr}}{GECN}$$

wherein
OLS is the optimal library size calculated as described in Example 6;
Gr is the expected germination rate in % after random mutagenesis; and
GECN is the number of germline cells.

For barley, the harvest rate and the germination rate are approximately the same, and thus the germination rate can be used in place of the harvest rate to calculate ONp.

By way of example, assuming an average germination rate of 95% and a GECN number of 2, 526.315 seeds need to be mutated in order to establish a library of 1.000.000 genomes.

$$ONp = \frac{\frac{1,000,000 \times 100}{95}}{2} = 526,314$$

Example 8

Determining the Number and Size of Sub-Pools

In order to screen large libraries in the most effective manner, the present invention proposes a multi-step method comprising at least the steps of dividing the initial pool into sub-pools, a step of screening to identify sub-pools comprising regenerative part(s) comprising the mutation screened for, followed by a subsequent step of identifying the specific regenerative parts comprising the mutation screened for within the identified sub-pool. The method of the invention allows screening very large numbers of regenerative parts within a reasonable time frame and work effort.

One major limiting factor with respect to determining the size of sub-pools is the detection limit of the screening method employed. If the detection sensitivity is endless, then the total size of the library is the biggest possible sub-pool. However, even in this scenario, it would be more beneficial to split the total library (the total pool) into sub-pools, otherwise every screen of the total pool results in a positive outcome and it will generally be very difficult and time consuming to identify the individual regenerative part responsible for the positive outcome.

If the detection sensitivity is 1 genome in Y genomes, then the maximum sub-pool size is in principle Y. By way of example, if the detection sensitivity is 1 in 2000 genomes, then the maximum sub-pool size is in principle a sub-pool comprising 2000 different genomes. If the total number different genomes per sub-pool is the same as the detection sensitivity, then every genome needs to be represented in roughly equal amounts within said sub-pool. This means that the samples preferably are collected in a way that a pooled DNA extraction will lead to an equal DNA contribution of every genotype. By placing all regenerative part of any given plant into the same sub-pool, the sub-pools will comprise roughly the same amount of regenerative part from each plant.

A sub-pool that is smaller than the maximum sub-pool size (determined based on the detection sensitivity of the screening technique), has the advantage that it can be less uniform, which greatly simplifies the preparation of sub-pools. For example, if a pool of 200 individuals is established, with each individual contributing 10 seeds, the total pool consists of 2000 seeds. A detection sensitivity of 1/2000 would allow 1999 seeds to be wild type and 1 mutated in order to identify it. Accordingly, with this pool it would have been feasible to harvest 90% less material of one individual while harvesting the same or more seeds for the remaining 199 individuals, still being able to detect the mutant in the final pool.

Thus, the sub-pool should have an adequate size for the specific detection sensitivity. The final number of sub-pools may be determined by the size of the total pool (i.e. Np) divided by the number of plants per sub-pool, based on the detection sensitivity and the amount of flexibility required for a non-uniform DNA pool.

The methods of the invention in general comprises a step of growing regenerative part into mature plants, and dividing regenerative part from said mature plants into sub-pools in a manner, so that all regenerative part from one mature plant is placed into the same sub-pool. Preparing sub-pools in this manner ensures that the sub-pools comprise roughly the same number regenerative parts of each genotype. If the plants comprise several germline cells per plant, each mature plant contributes regenerative part of more than one different genotype.

Thus, the maximal number of mature plants to provide regenerative part to a given sub-pool (herein referred to as the maximal sub-pool size (SPm)) can be calculated as follows:

$$SPm = \frac{Y}{GECN}$$

wherein
the detection sensitivity is 1 in Y; and
GECN is the number of germline cells By way of example, if the detection sensitivity is 1 in 2000, and assuming a GECN number of 5, the maximal sub-pool size is $$400 = \frac{2000}{5}$$

If the number of regenerative parts subjected to random mutagenesis was 526,315, and the maximal sub-pool size is 400, the pool of regenerative parts of M1, should be divided into at least 526,315/400=1315 sub-pools, wherein each sub-pool comprises regenerative parts from 400 plants. It may be preferred to reduce the size of the sub-pool, and accordingly the actual sub-pool size (Np) may be smaller than the optional sub-pool size (ONp).

Example 9

Determining the Size of the Optimal Number of Regenerative Parts (Np) to Start with and the Optimal Sub-Pool Size There are many plant-specific factors that may limit the size of a pool for screening. These factors can be:
the cost of storing a pool of a certain size
the ease in which a single plant or regenerative part thereof can be identified from a certain pool size
the speed in which a single plant can be identified from a certain pool size
the cost of identifying a single plant All of these factors are highly variable and plant-specific. For example, the propagation of individual plants of some crops is more expensive than the screening, for other plants vice versa. A person familiar with a specific crop would be able to judge all the factors and determine a comfortable size of a total pool. This size is the maximum size of a pool for practical rather than technical reasons.

For example, big plants (e.g. banana plants or trees) or plants with big fruits (e.g. water melons) take up a lot of space, and a rate limiting factor is thus the total number of plants, which can be grown. Accordingly, if the plant is a water melon, even though the number of seeds to reach an optimal library size may be high, a lower amount may be used for the method.

If the plant is grown in the field, typically large quantities of plants can be grown at low cost. Thus, the number of seeds propagated are not a limiting factor.

A notable, limiting factor relates to the number of grains that can be harvested per plant. If a plant only generates 10 grains and the number of germline cells is 5, then each germline cell will be represented by 2 grains only. In a self-pollinating crop only 75% of the grains from one germline will carry the desired mutation, and; in a cross pollinated crop only 50%. If it's necessary to split the pool at any stage, then this number becomes important.

Example 10

Preparing a DNA Sample

Once sub-pools have been generated, the method of the invention comprise a step of preparing a DNA sample. In general the DNA sample is prepared by dividing the entire sub-pool in a random number of fractions, and then preparing DNA from an entire fraction. Depending on the plant, each sub-pool will comprise a number of regenerative parts with the same genotype. The number will depend on the total number of regenerative parts per mature plant ($RP_p$), as well as the GECN number. If the GECN number is 1, the sub-pool will comprise $RP_p$ regenerative parts with the same genotype.

The optimal fraction size is a fraction size, wherein—in theory—each genotype is represented by one regenerative part. Thus, the optional fraction size may be calculated as follows:

$$\text{Optimal fraction size (\%)} = \frac{GECN * 100}{RPp}$$

By way of example, the following applies for a barley variety, which in average contains 20 seeds per plant, and which has a GECN number of 5. Thus, each M1 barley plant will comprise 20 seeds of each genotype. The sub-pools comprises all seeds of a mature barley plants. Thus, in principle, a random fraction the optimal fraction size (=25%) of the barley seeds of a given sub-pool will comprise 1 seed representing each genotype.

$$\text{Optimal fraction size (\%)} = \frac{5*100}{20} = 25\%$$

Example 11—Low Rate of Mutagenesis

A "low rate of mutagenesis" varies from crop to crop. In particular the ploidy of a crop plays an important role in how severe a crop reacts to a specific mutation treatment (Tsai et al 2013). This can also be observed based on the number of mutations tolerated (mutation frequency) in a hexaploid, tetraploid or diploid genome (Kurowska et al 2013). As explained above the mutation frequency is provided herein as mutations in a conventionally mutagenized hexaploid genome. For the purpose of constructing a low mutagenesis library, a low rate of mutagenesis in a diploid crop is comparable to <0.1% of genes with non-synonymous mutations in generation M1. In polyploid crops, like hexaploid wheat, a low mutation frequency is considered <1% of genes with non-synonymous mutations in generation M1.

The % genes free of non-synonymous mutations (GFoNSM) can be calculated according to the following formula:

$$GFoNSM = Gn \times Gl \times Mf \times \frac{Nsnm}{100}$$

Wherein Gn is the number of genes, Gl is the average gene length, Mf is the mutation frequency and Nsnm is the average number of non-synonymous mutations caused by mutagenesis in %. In this example Nsnm is 66%.

| Crop | Common name | Ploidy | Number of genes | Average gene length | Nucleotides per mutation M1 (25% less of M2) | Nucleotides per mutation M2 | mutations in coding regions in M1 | % of genes free of non-synonymous mutations in M1 | % of genes free of non-synonymous mutations in M1 |
|---|---|---|---|---|---|---|---|---|---|
| | | | | | | | | Conventional (high) mutagenesis | Low mutagenesis |
| Arabidopsis thaliana | Thale cress | diploid | 27655 | 1176 | 225000 | 300000 | 95 | 99.7 | >99.9 |
| Triticum durum | Durum wheat | tetraploid | 36434 | 1176 | 30000 | 40000 | 943 | 97.4 | >99 |
| Triticum aestivum | Wheat | hexaploid | 107891 | 1176 | 18000 | 24000 | 4652 | 95.7 | >99 |

$$Mf = \cdot \frac{1}{\text{Number of nucleotides per mutation}}.$$

| Crop | Common name | Ploidy | Conventional number of nucleotides per mutation in M2 |
|---|---|---|---|
| Arabidopsis thaliana | thale cress | diploid | 300.000 |
| Triticum durum | durum wheat | tetraploid | 40.000 |
| Triticum aestivum | Wheat | hexaploid | 24.000 |

The number of nucleotides per mutation in M2 plants is in general 25% lower than the number of nucleotides per mutation in the corresponding M1 plants, due to a selfing event which normally results in a loss of 25% of all heterozygous mutations.

In order to determine low and high rates of mutagenesis, we compare the number of genes that are free of any coding mutations in M1 plants. The number of genes that are free of any coding mutations is based on the number of genes in a given genome, the mutation frequency and the average length of a plant protein (Tiessen et al 2012). In diploid crops, a few hundred genes may contain coding mutations after the treatment with high, conventional mutation doses. In contrast, several thousand genes typically contain coding

Example 12

Developing a population of mutagenized *Brassica napus* and screening for mutants with a specific mutation in the gene for sinapaldehyde dehydrogenase/coniferaldehyde dehydrogenase (REF1)

Optimal Library Size and Optimal Number of Plants

The REF1 gene plays a role in the biosynthesis of sinapine, a major antinutritional compound in rapeseed (Emrani et al., 2015). We aimed to identify a REF1 knockout in a library of mildly mutagenized *Brassica napus* plants (i.e. low rate of mutagenesis). In a conventional mutagenized library of this tetraploid crop, >3.5% of all genes contain coding mutations. In a mildly mutagenized library fewer than 1% of all genes contain a mutation in a coding region. We have used a GBS sequencing approach to identify the number of mutations and the number of mutation origins in our population. A commercially available GBS sequencing approach was used to sequence 12 plants derived from a mutated *Brassica napus* individual. We utilized the following filters for the data analysis:

- Removal of loci from analysis who are not covered by at least 8 sequence reads in all analysed samples.
- Removal of loci with changes from the analysis who have additional changes within 50 basepairs distance as interpreted on the reference genome.
- Removal of samples from analysis, which are determined to be outliers.
- Disregarding loci changes in analysis when the locus show changes in any number of control samples.

Disregarding loci changes in analysis from loci who do not show changes in 25% or more of the sequence reads.

Disregarding loci changes in analysis for loci who show changes in sample group as well as in control samples.

Disregarding loci changes in analysis for loci who do not show changes in more than one sample in the sample group.

A total of 6.018.138 loci were included in the analysis. An average of 65.75 mutations were identified per plant, corresponding to an average mutation frequency of 1 mutation in 86.607 base pairs. We have identified 4 mutation origins, or genetically effective cells, in this group of plants, i.e. the GECN number is 4. This number can be calculated as follows. The unique mutations identified in the entire set of 12 samples all represent mutation events that occurred in the parental plant from which all samples originated.

The sum of unique mutations in the sample set then corresponds to the sum of identified heritable mutations that was present in the parental plant in the examined areas of the genome ($Sum_{par}$).

If all mutations occurred in a single heritable origin in the parental plant, the same mutations will be identified in all samples, and the ratio between the sum of unique mutations in the whole sample set and the average mutations in a single sample ($avg._{sam}$) will be 1. Assuming that all 12 samples in the sample set originate from different mutation origins, this ratio would be 12, as all identified mutations would be unique.

The number of different origins of mutations in the parental plants can then be deduced as being the ratio between the sum of unique parental mutations and the average number of mutations in a single sample.

Mutation origins=$Sum_{par}/Avg_{sam}$

Mutation origins=272/65.8=4.12

We identified 272 unique mutations in the 12 samples, with an average number of mutations per sample of 65.8, corresponding to a mutation origin number (or GECN) of 4.14.

This information can be used to determine the optimal library size that gives a 95% probability to identify at least one nucleotide substitution that leads to a premature stop in REF1.

$$OLS = \frac{\log\left(1 - \left(\frac{PS}{100}\right)\right)}{\log(1 - (1 - (Mf \times n))))}$$

$$OLS = \frac{\log\left(1 - \left(\frac{95}{100}\right)\right)}{\log(1 - (1 - (1/86607 \times 4))))} = 129,724$$

In order to have a 95% probability to identify one out of two stop codons in REF1, a library of 129,724 individuals is required. In order to calculate how many regenerative parts are required to obtain a library of 129,724 genotypes we can utilize the following formula:

$$ONp = \frac{\frac{OLS \times 100}{Hr}}{GeCN}$$

$$ONp = \frac{\frac{129724 \times 100}{17}}{4} = 190,771$$

When cultivating rapeseed, typically a lot more plants are sowed than harvested, and the harvest rate for rapeseed is thus rather low being approx. 17%. With a harvest rate of 17% and a GECN number of 4, 190.771 are the optimal number of seeds to be mutagenized to build a library that has a probability of 95% to identify at least one nucleotide substitution that leads to a premature stop in REF1.

Library Construction and Mutant Identification

A mutagenized library of *Brassica napus* cv. Epure was prepared. The library was organised using the pooling and splitting method described in PCT/EP2017/065516. A pool of 200.000 seeds was treated with 0.25% EMS for 16 hours at room temperature and propagated in a field using standard practices. 34.992 plants were harvested in pools of approximately 300 plants. DNA was extracted from 25% of the harvested material and utilized for the library screening.

Mutant identification was performed according to the ddPCR screening method described in PCT/EP2017/065516. Primers and probes were designed for the identification of a specific mutant at the REF1-locus. The desired mutant has a nucleotide change at position 504 from guanine to adenine of the coding sequence of REF-1, which is available under GenBank accession number NCBI: FN995990.1, that causes an amino acid change at position 168 that leads to a premature stop in the protein sequence, which is available under GenBank accession number NCBI: FN995990.1. In order to identify the mutant, a target specific forward primer (TATTGGAGTGGTCGGTC (SEQ ID NO: 9)), a target-specific reverse primer (CACTTTCATGGCAAACATAAT (SEQ ID NO: 10)), a mutant-specific detection probe (ATAATCCCTTGAAATTTTCCAAG (SEQ ID NO: 11)) labelled with 6-carboxyfluorescein (FAM) and a reference-specific detection probe (ATAATCCCTTGGAATTTTCCAA (SEQ ID NO: 12)) labelled with hexachlorofluorescein (HEX) were designed.

Example 13

This example describes developing a population of mildly mutagenized *Lactobacillus pasteurii* (Accession number with DMSZ—German Collection of Microorganisms and Cell Cultures: DSM 23907) and screening for mutants with a specific mutation in the gene for Galactose-1-phosphate uridylyltransferase (galP). The genomic sequence of the galP gene of *Lactobacillus pasteurii* is accessible at the European Nucleotide Archive under accession number CC184538, and references herein refer to version CC184538.1 available on 28 Mar. 2022. The protein sequence of galP of *Lactobacillus pasteurii* is accessible at the UniProt database under accession number 17LD34 and the references herein refer to version 17LD34_9LACO available on 28 Mar. 2022.

Optimal Library Size and Optimal Number of Cells

The aim of this example was to identify a galP knock-out in a library of mildly mutagenized *Lactobacillus pasteurii* cells. In a conventional mutagenized library of this haploid strain, a kill rate of 99% is desirable (Chen et al 2017). In mildly mutagenized haploid cells, the desired kill rate is between 20-50%. In this example, mutagenesis was performed to obtain a survival rate of approx. 75%, corresponding to an Hr of 75%. The genome of *Lactobacillus pasteurii* is ca. 1.900.000 base pairs (Cousin et al 2013). A mild mutagenesis library in that strain would have less than 25 coding mutations corresponding to a mutation frequency of 1 mutation in 76.000 base pairs. This corresponds to approximately 25 mutations per genome. Assuming that the entire genome consists of genes, and that the mutations are distributed throughout the genome, this mutagenesis corresponds to 16 genes comprising non-synonymous mutations, and approx. 99.2% of genes being free of non-synonymous mutations. The GECN number for prokaryotes is always 1. In this example two specific knock-out mutations were screened for, and thus n=2. This information can be used to determine the optimal library size that gives a 95% probability to identify at least one nucleotide substitution that leads to a premature stop in galP.

$$OLS = \frac{\log\left(1 - \left(\frac{PS}{100}\right)\right)}{\log(1 - (1 - (1 - (Mf \times n))))}$$

$$OLS = \frac{\log\left(1 - \left(\frac{95}{100}\right)\right)}{\log(1 - (1 - (1 - (1/76000 \times 2))))} = 113,836$$

In order to have a 95% probability to identify one out of two stop codons in galP, the Optimal library size (OLS) is 113,836 individuals.

The optimal number of organisms to be mutagenized (ONp) was 151,781, when calculated using the formula:

$$ONp = \frac{\frac{OLS \times 100}{Hr}}{GeCN}$$

In the present example, a library of 144,000 cells was used. The library size was determined as live cells after mutagenesis, and thus the calculated Np was 192,000.

The ddPCR assay used with the present example has a detection sensitivity of 2000. Thus, the maximum sub-pool size is 2000. In the present example, sub-pools of 1500 are used.

Library Construction and Mutant Identification

A mutagenized library of Lactobacillus pasteurii was developed essentially using a pooling and splitting method described in international patent application WO 2018/001884 with the amendments outlined below. In brief, Lactobacillus pasteurii was grown overnight in LB medium into stationary phase. The bacteria were subjected to a mild mutagenesis by adding 14 µl EMS to 1 ml of cells in a 2 ml safe-lock reaction tube, and incubating cells for approx. 30 minutes at 30° C. and 1000 rpm on an Eppendorf Thermomixer comfort (1.5 ml), which usually resulted in a killing rate of 25%, and hence a survival rate of approx. 75%. To stop the mutagenesis, cells were pelleted by brief centrifugation and washed three times with freshly prepared, sterile 5% sodium thiosulfate solution, and one time with sterile, distilled water and finally re-suspended in 1 ml LB. The viable cell titer was determined by plating respective dilutions on LB agar plates. Subsequently, approx. 1500 live cells were aliquoted into individual wells of one 96 well plate corresponding to a library size after mutagenesis of 96×1500=144.000 and an Np of 192,000.

The 96 well plate was incubated at 30° C. overnight allowing the cells to grow into stationary phase. The cells of each well were randomly divided into two fractions each containing approx. half of the cells. DNA was extracted in one batch from all cells of one of fractions and said DNA was subsequently screened for specific mutation events. Mutant identification was performed according to the ddPCR screening method described in international patent application WO 2018/001884. Primers and probes were designed for the identification of a specific mutant at two independent galP-loci, each causing a loss-of-function of the protein. One specific mutant has a nucleotide change at position 442 from cytosine to tyrosine of the galP gene, the sequence of which is accessible under accession number CC184538.1 in the European Nucleotide Archive. The mutation causes an amino acid change at position 148 of galP that leads to a premature stop in the protein sequence of galP that is available under accession number 17LD34_9LACO in the UniProt database. The other specific mutant has a nucleotide change at position 787 from cytosine to tyrosine of the galP gene, the sequence of which is accessible under accession number CC184538.1 in the European Nucleotide Archive. The mutation causes an amino acid change at position 263 that leads to a premature stop in the protein sequence of galP that is available under accession number 17LD34_9LACO in the UniProt database. In order to identify the mutants, a target specific forward primer, a target-specific reverse primer, a mutant-specific detection probe labelled with 6-carboxyfluorescein (FAM) and a reference-specific detection probe labelled with hexachlorofluorescein (HEX) were designed for each target loci, which can be obtained from BioRad with assay ID dMDS968002337 (C442T) and dMDS395817510 (C787T). Screening of the library of 96×1500 cells (total library size 144.000) resulted in the identification of 1 of the two designed assays (C442T), which confirms the OLS of 113,836 events for a 95% probability to identify a specific mutant.

Example 14

This example describes developing a population of mildly mutagenized diploid Saccharomyces cerevisiae (strain 6D4) and screening for mutants with a specific mutation in the gene for Isoamyl acetate-hydrolyzing esterase (IAH1). The genomic sequence of the IAH1 gene in Saccharomyces cerevisiae is accessible at the European Nucleotide Archive under accession number X92662 available on 30 Mar. 2022. The protein sequence of IAH1 of Saccharomyces cerevisiae is accessible at the UniProt database under accession number P41734 available on 30 Mar. 2022.

Optimal Library Size and Optimal Number of Cells

The aim of this example was to identify a IAH1 knock-out in a library of mildly mutagenized Saccharomyces cerevisiae cells. In a conventional mutagenized library of this haploid strain, a kill rate of 99% is desirable (Chen et al 2017). In mildly mutagenized diploid cells, the desired kill rate is preferably between 40-60%. In this example, mutagenesis was performed to obtain a survival rate of approx. 45% The genome of Saccharomyces cerevisiae is ca. 12.000.000 base pairs. A mild mutagenesis library in that strain would have less than 250 mutations per genome corresponding to a mutation frequency of 1 mutation in 48.000 base pairs. The number of genes in S. cerevisiae has been estimated to be around 5400 genes having an average length of 1400 bp. On this basis it is estimated that mutagenesis performed as described in this example results in 104 genes carrying non-synonymous mutations, and thus approximately 98% genes being free of non.synonymous mutations. The GECN number for yeast is always 1. In this example specific knock-out mutation was screened for, and thus n=1. This information can be used to determine the optimal library size that gives a 95% probability to identify at least one nucleotide substitution that leads to a premature stop in IAH1.

$$OLS = \frac{\log\left(1 - \left(\frac{PS}{100}\right)\right)}{\log(1 - (1 - (1 - (Mf \times n))))}$$

$$OLS = \frac{\log\left(1 - \left(\frac{95}{100}\right)\right)}{\log(1 - (1 - (1 - (1/48000 \times 1))))} = 143{,}793$$

In order to have a 95% probability to identify one out of two stop codons in IAH1, the Optimal library size (OLS) is 143,793 individuals.

The optimal number of organisms to be mutagenized (ONp) was 319,541, when calculated using the formula:

$$ONp = \frac{\frac{OLS \times 100}{Hr}}{GECN}$$

based on the survival rate and thus Hr being 45%.

In the present example, a library of 144,000 cells was used. The library size was determined as live cells after mutagenesis, and thus the calculated Np was 320,000.

The ddPCR assay used with the present example has a detection sensitivity of 2000. Thus, the maximum sub-pool size is 2000. In the present example, sub-pools of 300 are used.

Library Construction and Mutant Identification

A mutagenized library of *Saccharomyces cerevisiae* was developed essentially using a pooling and splitting method described in international patent application WO 2018/001884 with the amendments outlined below. In brief, *Saccharomyces cerevisiae* was grown overnight in YPD medium into stationary phase. The yeast were subjected to a mild mutagenesis by adding 14 µl EMS to 1 ml of cells in a 2 ml safe-lock reaction tube, and incubating cells for approx. 1 hr 10 mins minutes at 30° C. and 1000 rpm on an Eppendorf Thermomixer comfort (1.5 ml), which usually resulted in a killing rate of 55%, and hence a survival rate of approx. 45%. To stop the mutagenesis, cells were pelleted by brief centrifugation and washed three times with freshly prepared, sterile 5% sodium thiosulfate solution, and one time with sterile, distilled water and finally re-suspended in 1 ml YPD. The viable cell titer was determined by plating respective dilutions on YPD agar plates. Subsequently, approx. 300 live cells were aliquoted into individual wells of five 96 well plate corresponding to a library size after mutagenesis of 96×300*5=144.000 and an Np of 320,000.

The 96 well plate was incubated at 23° C. allowing the cells to grow into stationary phase. The cells of each well were randomly divided into two fractions each containing approx. half of the cells. DNA was extracted in one batch from all cells of one of fractions and said DNA was subsequently screened for specific mutation events. Mutant identification was performed according to the ddPCR screening method described in international patent application WO 2018/001884. Primers and probes were designed for the identification of a specific mutant at two independent IAH1-loci, each causing a loss-of-function of the protein. One specific mutant has a nucleotide change at position 174 from tryptophan to stop codon of the IAH1 gene, the sequence of which is accessible under accession number X92662 in the European Nucleotide Archive. The mutation causes an amino acid change at position 58 of IAH1 that leads to a premature stop in the protein sequence of IAH1 that is available under accession number P41734 in the UniProt database. The other specific mutant has a nucleotide change at position 142 from glutamine to stop of the IAH1 gene, the sequence of which is accessible under accession number X92662 in the European Nucleotide Archive. The mutation causes an amino acid change at position 48 that leads to a premature stop in the protein sequence of IAH1 that is available under accession number P41734 in the UniProt database. In order to identify the mutants, a target specific forward primer, a target-specific reverse primer, a mutant-specific detection probe labelled with 6-carboxyfluorescein (FAM) and a reference-specific detection probe labelled with hexachlorofluorescein (HEX) were designed for each target loci, which can be obtained from BioRad with assay ID dMDS655670975 (G174A) and dMDS779469993 (C142T). Screening of the library of 96×300×5 cells (total library size 144.000) resulted in the identification of the designed mutant, which confirms the OLS of 143,793 events for a 95% probability to identify a specific mutant.

Items

1. A method for identifying a mutant plant of a predefined species carrying one or more mutation(s) in nucleotide(s) of interest [NOI(s)], in a predetermined target sequence, said method comprising the steps of:
   a) providing $N_p$ regenerative parts of a parent plant of said species, wherein Np is a integer >5,000, such as >10,000, such as >15,000, such as >20,000, such as >25,000, such as >30,000;
   b) subjecting said regenerative parts to a step of mutagenesis, preferably of random mutagenesis, thereby generating a pool of regenerative parts of generation M0 representing a plurality of genotypes;
   c) growing said regenerative parts of generation M0 into mature plants of generation M1 and obtaining regenerative parts of generation M1 from said mature plants;
   d) optionally repeating the previous step X times to obtain plants of generation M(1+X) comprising regenerative parts of generation M(1+X);
   e) dividing regenerative parts of a plurality of generation M1 or M(1+X) plants into sub-pools, each sub-pool comprising regenerative parts representing a plurality of genotypes, wherein all regenerative parts from one given mature plant are placed in the same sub-pool;
   f) preparing DNA samples, such as gDNA samples or cDNA samples obtained from mRNA samples, from each sub-pool;
   g) identifying sub-pool(s) comprising DNA comprising the mutation(s) using sensitive detection means;
   h) identifying regenerative parts within said sub-pool comprising said mutation, thereby identifying said mutant plant,
   wherein said step of mutagenesis leads to a rate of mutagenesis of 1 to 30 non-synonymous mutations per cell of a regenerative part of generation M1.

2. A method for identifying a mutant plant of a predefined species carrying one or more mutation(s) in nucleotide(s) of interest [NOI(s)], in a predetermined target sequence, said method comprising the steps of:
   a) providing Np regenerative parts of a parent plant of said species, wherein Np is an integer of at least 5,000, such as at least 10,000, such as at least 15,000, such as at least 20,000, such as at least 25,000, such as at least 30,000;
b) subjecting said regenerative parts to a step of mutagenesis, preferably of random mutagenesis, leading to a low rate of mutagenesis, thereby generating a pool of regenerative parts of generation M0 representing a plurality of genotypes;
c) growing said regenerative parts of generation M0 into mature plants of generation M1 and obtaining regenerative parts of generation M1 from said mature plants;
d) optionally repeating the previous step X times to obtain plants of generation M(1+X) comprising regenerative parts of generation M(1+X);
e) dividing regenerative parts of a plurality of generation M1 or M(1+X) plants into sub-pools, each sub-pool comprising regenerative parts representing a plurality of genotypes, wherein all regenerative parts from one given mature plant are placed in the same sub-pool;
f) preparing DNA samples, such as gDNA samples or cDNA samples obtained from mRNA samples, from each sub-pool;
g) identifying sub-pool(s) comprising DNA comprising the mutation(s) using sensitive detection means;
h) identifying regenerative parts within said sub-pool comprising said mutation, thereby identifying said mutant plant,
wherein a low rate of mutagenesis in diploid plants is that in average at least 99.8%, preferably at least 99.9% of all genes are free of non-synonymous mutations and in plants of higher ploidy that in average at least 98.0%, preferably at least 99.0% of all genes are free of non-synonymous mutations in a regenerative part of generation M1, preferably wherein the regenerative part is a vegetative tissue, a seed, a grain, a germline cell in a seed, a grain or an embryo of said plant, pollen or an embryo, preferably the regenerative part is a seed.

3. A method for identifying a mutant microorganism of a predefined species carrying one or more mutation(s) in nucleotide(s) of interest [NOI(s)], in a predetermined target sequence, said method comprising the steps of:
I. providing $N_p$ microorganisms of said species, wherein $N_p$ is an integer of at least 5000;
II. subjecting said microorganisms to a step of mutagenesis, preferably of random mutagenesis, leading to a low rate of mutagenesis, wherein said mutagenesis leads to a survival rate of at least 30%, thereby generating a pool of microorganisms representing a plurality of genotypes;
III. dividing said mutagenized microorganisms into physically separated sub-pools;
IV. subjecting each sub-pool to a step of reproduction so that each sub-pool in theory comprises more than one microorganisms of each genotype,
V. preparing DNA samples, such as cDNA samples prepared from mRNA samples or gDNA samples, from each sub-pool;
VI. identifying sub-pool(s) comprising DNA comprising the mutation(s) using sensitive detection means;
VII. identifying microrganisms within said sub-pool comprising said mutation.

4. The method according to item 3, wherein the step of reproduction of the sub-pools is performed in a manner so that each viable microorganism within the sub-pool is reproduced at least once.

5. The method according to any one of items 3 to 4, wherein the sub-pools are reproduced in a manner, so that each sub-pool in theory comprises at least 2, such as at least 4, for example at least 10, such as in the range of 2 to 100 microorganisms of each genotype represented in the sub-pool.

6. The method according to any one of items 3 to 5, wherein the microorganism is a unicellular organism.

7. The method according to any one of items 3 to 6, wherein the microorganisms are selected from the group consisting of prokaryotes, yeasts, fungi and algae.

8. The method according to any one of the preceding items, wherein step e) is performed by a method comprising the steps of
i. determining the optimal size of the sub-pool, wherein the maximum sub-pool size (SPm)

$$SPm = \frac{Y}{GRCN} \quad SPM = \frac{Y}{GECN}$$

ii. dividing said regenerative parts into sub-pools, wherein each sub-pool comprises regenerative parts from a number of mature plants, said number being in the range of 0.5*SPm to 1.1*$_{Spm}$SPm, wherein all regenerative parts from one given mature plant are placed in the same sub-pool;
wherein the detection sensitivity of sensitive detection means is 1 in Y, and wherein the plants have a genetically effective cell number of GECN.

9. A method of identifying a plant, or regenerative parts thereof, of a predefined plant species having a genetically effective cell number (GECN), wherein the plant carries at least one of n predetermined mutation(s) in nucleotide(s) of interest [NOI(s)], in a target sequence, said method employing detection means for detecting nucleic acid sequences with a detection sensitivity of 1 in Y, comprising the steps of:
a) providing $N_p$ regenerative parts of plants of said species, wherein $N_p$ is an integer >1000, for example at least 5,000, such as at least 10,000, such as at least 15,000, such as at least 20,000, such as at least 25,000, such as at least 30,000,
b) subjecting said regenerative parts to a step of mutagenesis, preferably of random mutagenesis, thereby generating a pool of regenerative parts of generation M0 representing a plurality of genotypes;
c) growing said regenerative parts of generation M0 into mature plants and obtaining regenerative parts of generation M1 from said mature plants;
d) optionally repeating the previous step X times to obtain plants comprising regenerative parts of generation M(1+X);
e) dividing said regenerative parts of generation M1 or M(1+X) into sub-pools by a method comprising the steps of:
i) determining the optimal size of the sub-pool, wherein the maximum sub-pool size (SPm)

$$SPm = \frac{Y}{GECN}$$

ii) dividing said regenerative parts into sub-pools, wherein each sub-pool comprises regenerative parts from a number of mature plants, said number being in the range of 0.5*SPm to 1.1*SPm, wherein all regenerative parts from one given mature plant are placed in the same sub-pool;

f) preparing a DNA sample, such as a gDNA sample or a cDNA sample, from each sub-pool;

g) identifying sub-pool(s) comprising regenerative parts comprising the mutation(s) using said detection means;

h) identifying regenerative parts within said sub-pool comprising said mutation, thereby identifying said mutant plant.

10. The method according to any one of the preceding items, wherein the detection means for detecting nucleic acid sequences are sensitive detection means.

11. The method according to any one of the preceding items, wherein each sub-pool comprises regenerative part from in the range of 0.5*SPm to SPm mature plants.

12. The method according to any one of the preceding items, wherein each sub-pool comprises regenerative part from in the range of 0.7*SPm to SPm mature plants.

13. The method according to any one of the preceding items, wherein the species is a microorganism and each sub-pool initially comprises in the range of 0.5*SPm to SPm viable microorganisms, such as in the range of 0.7*SPm to SPmSPm viable microorganisms.

14. The method according to any one of items 3 to 12, wherein the species is a microorganism and said microorganisms are not incubated under conditions allowing reproduction in the interim between mutagenesis and dividing microorganisms into sub-pools.

15. The method according to any one of the preceding items, wherein $N_p$ is in the range of 0.7*ONp to 1.3*ONp, wherein $$ONp = \frac{\frac{OLS \times 100}{Hr}}{GECN};$$

and wherein Hr is the expected average harvest rate of said plant species after mutagenesis in % or the survival rate of said microorganism in %; and OLS is optimal library size, wherein $$OLS = \frac{\log\left(1 - \frac{PS}{100}\right)}{\log(1 - (1 - (1 - (Mf \times n))))}$$

wherein PS is PS is the probability of success in %; and
Mf is the mutation frequency; and
n is the number of mutations screened for; and
wherein step b) or step II) comprises a step of random mutagenesis leading to a mutagenesis frequency of Mr.

16. The method according to any one of the preceding items, wherein the library size (LS) is in the range of 0.5*OLS to 5*OLS, preferably in the range of 0.5*OLS to 2*OLS, for example in the range of 0.7*OLS to 1.3*OLS, wherein $$OLS = \frac{\log\left(1 - \frac{PS}{100}\right)}{\log(1 - (1 - (1 - (Mf \times n))))}$$

wherein PS is the probability of success in %; and
Mf is the mutation frequency; and
n is the number of mutations screened for.

17. The method according to item 16, wherein the species is a microorganism and LS is the total the number of viable microorganisms, which are divided into the sub-pools.

18. The method according to item 15, wherein the harvest rate is the germination rate of said plant species after mutagenesis in %.

19. The method according to item 15, wherein the species is a microorganism and Hr is the survival rate of said microorganism after mutagenesis in %.

20. The method according to any one of the preceding items, wherein Np is in the range of 0.8*ONp to 1.2*ONp.

21. The method according to any one of the preceding items, wherein Np is in the range of 0.9*ONp to 1.1*ONp.

22. The method according to any one of the preceding items, wherein the regenerative parts are seeds.

23. The method according to any one of the preceding items, wherein the probability of success is at least 85%, preferably at least 90%, more preferably at least 95%, such as at least 98%.

24. The method according to any one of the preceding items, wherein at least 30,000 regenerative parts are provided in step a), such as at least 40,000 regenerative parts, such as at least 50,000 regenerative parts, such as at least 60,000 regenerative parts, such as at least 70,000 regenerative parts, such as at least 80,000 regenerative parts, such as at least 90,000 regenerative parts, such as at least 100,000 regenerative parts, such as at least 200,000 regenerative parts, such as at least 300,000 regenerative parts, such as at least 400,000 regenerative parts, such as at least 500,000 regenerative parts, such as at least 600,000 regenerative parts, such as at least 700,000 regenerative parts, such as at least 800,000 regenerative parts, such as at least 900,000 regenerative parts, such as at least $10^6$ regenerative parts $2.10^6$ regenerative parts, such as at least $3.10^6$ regenerative parts, such as at least $4.10^6$ regenerative parts, such as at least $5.10^6$ regenerative parts, such as at least $6.10^6$ regenerative parts, such as at least $7.10^6$ regenerative parts, such as at least $8.10^6$ regenerative parts, such as at least $9.10^6$ regenerative parts such as at least $10^7$ regenerative parts or more, are provided in step a).

25. The method according to any one of the preceding items, wherein the rate of mutagenesis is at the most 1 mutation in every 1000 genes, such as at the most 1 mutation every 5000 genes, such as at the most 1 mutation every 10000 genes, such as at the most 1 mutation every 20000 genes, such as at the most 1 mutation every 30000 genes.

26. The method according to any one of the preceding items, wherein said mutagenesis leads to at the most 25 non-synonymous mutations in coding regions, such as at the most 20 non-synonymous mutations in coding regions, such as at the most 15 non-synonymous mutations in coding regions, such as at the most 10 non-synonymous mutations in coding regions, such as at the most 5 non-synonymous mutations in coding regions, such as 1 non silent-mutation in a coding region in plants of generation M1.

27. The method according to any one of the preceding items, wherein the low rate of mutagenesis in microorganism is at least 95%, such as at least 96%, for example at least 97%, such as at least 98%, for example at least 99% of the genes of the microorganism are free of non-synonymous mutations.

28. The method according to any one of the preceding items, wherein the plant is a diploid plant and said low rate of mutagenesis is a mutation frequency of 1 in at least 500,000, such as 1 in at least 750,000, for example 1 in at least 1,000,000.

29. The method according to any one of the preceding items, wherein the plant is a tetraploid plant and said low rate of mutagenesis is a mutation frequency of 1 in at least 70,000, such as 1 in at least 100,000, for example 1 in at least 300,000.

30. The method according to any one of the preceding items, wherein the plant is a hexaploid plant and said low rate of mutagenesis is a mutation frequency of 1 in at least 40,000, such as 1 in at least 80,000, for example 1 in at least 200,000.

31. The method according to any one of the preceding items, wherein the low rate of mutagenesis is mutagenesis resulting in a survival rate of at least 30%, preferably at least 40%, even more preferably at least 45%.

32. The method according to any one of the preceding items, wherein the mutagenesis is a chemical mutagenesis or irradiation-induced mutagenesis.

33. The method according to any one of the preceding items, wherein the mutagenesis is a chemical mutagenesis performed with a mutagenizing chemical such as a mutagenizing chemical selected from the group consisting of sodium azide ($NaN_3$), ethyleneimine, hydroxylamine ($NH_2OH$), N-methyl-N'-nitro-N-nitrosoguanidine (MNNG), diazomethane, methylnitrosoguanidine (MNNG) and ethyl methanesulfonate (EMS) and alkylating agents such as sulfonates, such as ethylmethane sulfonate (EMS), diethyl sulfonate (DES) or N-ethyl-N-nitrosourea (ENU), or such as sulphur mustards, such as ethyl-2-chloroethyl sulphide, or such as nitrogen mustards such as 2-chloroethyl-dimethyl amine, or such as epoxides, such as ethylene oxide.

34. The method according to any one of the preceding items, wherein the step of random mutagenesis is performed with sodium azide, preferably at a concentration of 1 mM or less for 2 hours or less, such as 0.9 mM or less, such as 0.8 mM or less, such as 0.7 mM or less, such as 0.6 mM or less, such as 0.5 mM or less, such as 0.4 mM or less, such as 0.3 mM or less.

35. The method according to any one of items 1 to 33, wherein the step of random mutagenesis is performed with EMS, preferably at a concentration of 4% or less for 2 hours or less, such as 3% or less, such as 2% or less, such as 1.5% or less, such as 1% or less, such as 0.75% or less, such as 0.5% or less, such as 0.4% or less, such as 0.3% or less, such as 0.2% or less, such as 0.1% or less, such as 0.1% for 24 hours or less.

36. The method according to any one of items 1 to 33, wherein the species is a microorganism and the step of random mutagenesis is performed with EMS, by subjecting said microorganisms to in the range of 0.5 to 2% EMS, such as to in the range of 1 to 2% EMS, for example in the range of 1.2 to 1.6% EMS for in the range of 10 min to 3 hours, such as in the range of 10 min. to 2 hours, for example in the range of 20 min. to 2 hours, such as in the range of 20 min. to 1 hour, for example in the range of 20 to 40 min.

37. The method according to any one of the preceding items, wherein the mutagenesis is performed in conditions such that at least 90% of the regenerative parts survive the step of mutagenesis, such as at least 91%, of the regenerative parts, such as at least 92% of the regenerative parts, such as at least 93% of the regenerative parts, such as at least 94% of the regenerative parts, such as at least 95% of the regenerative parts, such as at least 96% of the regenerative parts, such as at least 97% of the regenerative parts, such as at least 98% of the regenerative parts, or such as at least 99% of the regenerative parts survive the step of mutagenesis.

38. The method according to any one of the preceding items, wherein said mutant plant has the same phenotype as the parent plant, except from the phenotypic trait(s) caused by the mutation(s) in the target sequence.

39. The method according to any one of the preceding items, wherein one or more of the appearance, height, biomass, yield, grain size, fitness, leaf shape and taste of said mutant plant is the same as in the parent plant, preferably all of the appearance, height, biomass, leaf shape and taste of said mutant plant are the same as in the parent plant.

40. The method according to any one of the preceding items, wherein the (crop) yield of said mutant plant corresponds to at least 90%, such as at least 91%, such as at least 92%, such as at least 93%, such as at least 94%, such as at least 95%, such as at least 96%, such as at least 97%, such as at least 98%, such as at least 99%, such as at least 100%, such as at least 105%, such as at least 110%, such as at least 125%, such as at least 150%, such as at least 175%, such as at least 200% of the total (crop) yield of the parent plant, or more.

41. The method according to any one of the preceding items, wherein the grain quality of said mutant plant is substantially the same as or greater than the grain quality of the parent plant.

42. The method according to any one of the preceding items, wherein mutations of interest occur at a frequency corresponding to 1 mutation per 1.5 million microorganisms or plants.

43. The method according to any one of the preceding items, wherein at least 5,000 regenerative parts, such as at least 10,000 regenerative parts, such as at least 15,000 regenerative parts, such as at least 20,000 regenerative parts, such as at least 25,000 regenerative parts, such as at least 30,000 regenerative parts, such as at least 40,000 regenerative parts, such as at least 50,000 regenerative parts, such as at least 60,000 regenerative parts, such as at least 70,000 regenerative parts, such as at least 80,000 regenerative parts, such as at least 90,000 regenerative parts, such as at least 100,000 regenerative parts, such as at least 200,000 regenerative parts, such as at least 300,000 regenerative parts, such as at least 400,000 regenerative parts, such as at least 500,000 regenerative parts, such as at least 600,000 regenerative parts, such as at least 700,000 regenerative parts, such as at least 800,000 regenerative parts, such as at least 900,000 regenerative parts, such as at least $10^6$ regenerative parts, such as at least $10^6$ mature plants, such as $2.10^6$ mature plants, such as at least $3.10^6$ mature plants, such as at least $4.10^6$ mature plants, such as at least $5.10^6$ mature plants, such as at least $6.10^6$ mature plants, such as at least $7.10^6$ mature plants, such as at least $8.10^6$ mature plants, such as at least $9.10^6$ mature plants, such as at least $10^7$ mature plants are obtained in step c).

44. The method according to any one of the preceding items, wherein the viability of the regenerative parts of generation M0 is the same as or greater than the viability of the regenerative parts provided in step a).

45. The method according to any one of the preceding items, wherein the sterility of said mutant plant is below 30%.

46. The method according to any one of the preceding items, wherein the plant is a crop plant or a flowering plant, such as a plant belonging to the Brassicaceae family, the Fabaceae family, the Poaceae family, the Amaranthaceae family, the Asteraceae family, the Solanaceae family, the Rubiaceae family or the Orchidaceae family.

47. The method according to any one of the preceding items, wherein the plants is selected from the group consisting of cereals, legumes and Brassicaceae.

48. The method according to any one of the preceding items, wherein the plant is barley.

49. The method according to any one of the preceding items, wherein the plant species has an average number of regenerative parts per plant of $RP_p$, and wherein step f) comprises
    i. randomly dividing each sub-pool into fractions, wherein a first fraction comprises in the range of $$\frac{GECN*100}{RPp}\%$$

to $$\frac{GECN*500}{RPp}\%$$

of the regenerative part of the sub-pool; and wherein said first fraction comprises at the most 50% of said regenerative part;
    ii. preparing DNA samples of the entire first fraction of each sub-pool.

50. The method according to any one of the preceding items, wherein step f) or step V comprises the steps of: dividing each sub-pool into fractions; preparing DNA samples, such as gDNA samples or cDNA samples obtained from mRNA samples, of an entire fraction of each sub-pool.

51. The method according to any one of the preceding items, wherein step f) or step V is performed by dividing each sub-pool into at least 2 fractions, such as at least 3 fractions, such as at least 4 fractions, and preparing DNA samples from an entire fraction of each sub-pool.

52. The method according to any one of the preceding items, wherein the step f) or step V comprises obtaining a fraction comprising in the range of 10 to 50% of regenerative parts of each sub-pool and preparing DNA samples from the entire fractions of each sub-pool.

53. The method according to any one of the preceding items, wherein the detection means or the sensitive detection means have a detection sensitivity of 1 in at least 1000, such as a detection sensitivity of 1 to in the range of 1000 to 10,000 for example a detection sensitivity of 1 to in the range of 1000 to 5000.

54. The method according to any one of the preceding items, wherein step g) or step VI for each sub-pool comprises the steps of:
    performing one or more PCR amplifications, comprising the DNA sample from said fraction of the sub-pool, one or more set(s) of primers each set flanking the target sequence and PCR reagents, thereby amplifying the target sequence(s);
    detecting PCR amplification product(s) comprising the target sequence(s) comprising the one or more mutation(s) in the NOI(s).

55. The method according to item 54, wherein the one or more PCR amplifications are partitioned into a plurality of spatially separated compartments.

56. The method according to item 55, wherein said spatially separated compartments are droplets, such as a water-oil emulsion droplets.

57. The method according to item 56, wherein each droplet has an average volume in the range of 0.1 to 10 nL.

58. The method according to any one of items 55 to 57, wherein each PCR is compartmentalised into in the range of 1000 to 100,000 spatially separated compartments.

59. The method according to any one of items 41 to 58, wherein the PCR reagents comprises one or more mutation detection probes, wherein each mutation detection probe(s) comprise(s) an oligonucleotide optionally linked to detectable means, wherein the oligonucleotide is identical to—or complementary to—a target sequence, including a predetermined mutation of the NOI.

60. The method according to any one of items 41 to 59, wherein the PCR reagents comprises one or more reference detection probe(s), wherein each reference detection probe(s) comprise(s) an oligonucleotide optionally linked to detectable means, wherein the oligonucleotide is identical to—or complementary to—a target sequence, including a reference NOI.

61. The method according to item 60, wherein the mutant detection probe(s) is (are) linked to a fluorophore and a quencher, and the reference detection probe is linked to a different fluorophore and a quencher.

62. The method according to any one of items 60 to 61, wherein the PCR reagents comprises an at least 2-fold excess of the mutant detection probe(s) over the reference detection probe(s).

63. The method according to any one of items 53 to 62, wherein the PCR is an RNase H-dependent PCR.

64. The method according to any one of the preceding items, wherein the mutagenesis of step a) is random mutagenesis.

65. The method according to any one of the preceding items, wherein $10^6$ regenerative parts of generation M0 with different genotypes are obtained in step b), such as at least $2.10^6$ regenerative parts, such as at least $3.10^6$ regenerative parts, such as at least $4.10^6$ regenerative parts, such as at least $5.10^6$ regenerative parts, such as at least $6.10^6$ regenerative parts, such as at least $7.10^6$ regenerative parts, such as at least $8.10^6$ regenerative parts, such as at least $9.10^6$ regenerative parts such as at least $10^7$ regenerative parts or more.

66. The method according to any one of the preceding items, wherein the method comprises a step of reproduction of the organisms, or regenerative parts thereof, within the pool, and wherein said step of reproducing may be performed simultaneously with, or subsequent to, step e) of dividing the organisms into sub-pools.
67. The method according to any one of the preceding items, wherein the method comprises a step of obtaining plants of generation M(1+X), wherein all regenerative parts of all progeny of a given M0 generation plant are placed in the same sub-pool.
68. The method according to any one of the preceding items, wherein the step of identifying regenerative part within an identified sub-pool comprises the steps of
   i) growing the regenerative part into plants
   ii) preparing a DNA sample from each of said plants
   iii) identifying plants comprising the mutation.
69. The method according to any one of the preceding items, wherein the regenerative parts of step e) are of generation M2.
70. The method according to any one of the preceding items, wherein step h) comprises the following steps:
   Providing a sub-pool comprising a plurality of regenerative parts of a plant, wherein said sub-pool comprises regenerative parts comprising one or several mutation(s) of the NOI(s);
   Dividing the regenerative parts of said sub-pool into secondary sub-pools;
   Obtaining a sample from each regenerative part of the secondary sub-pools—in a manner leaving the regenerative parts sufficiently intact to develop into a plant—and combining all samples from all regenerative parts of each secondary sub-pool;
   Preparing a DNA sample from said combined samples;
   Identifying secondary sub-pool(s) comprising DNA comprising the mutation(s).
71. The method according to item 70, wherein said sample is obtained by drilling a hole into the regenerative part, preferably a seed, followed by collecting the flour obtained.
72. The method according to any one of items 70 to 71, further comprising the steps of:
   Providing the identified secondary sub-pool comprising regenerative parts comprising the mutation in the NOI, wherein the regenerative parts are seeds;
   Cultivating all seeds within said secondary sub-pool to allow germination, and optionally develop plants from each seed;
   Obtaining a sample from each germinated seed;
   Testing said sample for the presence of said mutation in the NOI, thereby identifying a plant carrying the mutation in the NOI;
   Optionally growing said plant to maturity.
73. The method according to item 72, wherein the method further comprises the following steps performed after step f):
   Obtaining a fraction of each DNA sample from each sub-pool;
   Combining a plurality of fractions into super-pools, thereby obtaining DNA super-pools comprising DNA samples from a plurality of sub-pools, wherein DNA from each sub-pool is only present in one super-pool;
   Performing a plurality of PCR amplifications, each comprising a DNA sample super-pool, wherein each PCR amplification comprises a plurality of compartmentalised PCR amplifications, each comprising part of said DNA sample, one or more set(s) of primers each set flanking a target sequence and PCR reagents, thereby amplifying the target sequence(s);
   Detecting PCR amplification product(s) comprising one or more target sequence(s) comprising the mutation(s) in the NOI(s), thereby identifying super-pool(s) comprising said mutation.
74. The method according to item 73, wherein PCR amplifications are performed only on samples of DNA from sub-pool(s) comprising one of the mutation(s).
75. The method according to any one of items 73 to 74, wherein in the range of 5 to 100 super-pools are prepared.
76. The method according to any one of items 73 to 75, wherein the PCR amplification(s) comprising a DNA sample super-pool is (are) performed by a method comprising the following steps:
   Preparing a PCR amplification comprising the DNA sample, one or more set(s) of primer(s) each set flanking a target sequence and PCR reagents;
   Partitioning said PCR amplification(s) into a plurality of spatially separated compartments, wherein each compartment has an average volume in the range of 0.1 to 10 pL;
   Performing a PCR amplification;
   Detecting PCR amplification products.
77. The method according to any one of items 73 to 76, wherein the PCR is an RNase H-dependent PCR.
78. The method according to any one of items 73 to 77, wherein each PCR is compartmentalised into at least 1,000,000 compartments, such as spatially separated compartments.
79. The method according to any one of items 73 to 78, wherein said spatially separated compartments are droplets, such as a water-oil emulsion droplets.
80. The method according to any one of the preceding items, wherein the mutation is an expected loss of function mutation in a predetermined polypeptide and the expected number of mutations screened for is 5% of the number of amino acids of said polypeptide.
81. The method according to any one of the preceding items, wherein the number of mutations screened for (n) is 1.
82. The method according to any one of the preceding items, wherein the mutation is a substitution of a single nucleotide.
83. The method according to any one of the preceding items, wherein the method is a method of identifying one predetermined mutation in a target sequence, and the method employs only one set of primers flanking said target sequence.
84. The method according to any one of items 41 to 83, wherein the PCR reagents comprise only one mutation detection probe.
85. The method according to any one of the preceding items, wherein the regenerative part is a vegetative tissue, a seed, a grain, a germline cell in a seed, a grain or an embryo of said plant, pollen or an embryo, preferably the regenerative part is a seed.

REFERENCES

Chen, J, Vestergaard., M., Jensen, T. G, Shen, J., Dufva, M., Solem., C, et al. (2017). Finding the needle in the haystack—the use of microfluidic droplet technology to identify vitamin-secreting lactic acid bacteria. mBio 8:e00526-17. doi: 10.1128/mBio.00526-17

Chen et al. (2018) CRISPR-Cas12a target binding unleashes indiscriminate single-stranded DNAse activity. Science 27: 436-439

Cousin S, Clermont D, Creno S, Ma L, Loux V, Bizet C, Bouchier C. 2013. Draft genome sequence of *Lactobacillus pasteurii* CRBIP 24.76$^T$. Genome Announc. 1(4): e00660-13. doi:10.1128/genomeA.00660-13.

Dobosy et al. (2011) RNase H-dependent PCR (rhPCR): improved specificity and single nucleotide polymorphism detection using blocked cleavable primers. BMC Biotechnology 11, 80

Emrani et al. (2015) Reduction in sinapine content in rapeseed (*Brassica napus* L.) by induced mutations in sinapine biosyntheis genes. Molecular Breeding. 35. 1-11. 10.1007/s11032-015-0236-2.

Hindson et al. (2011). High-throughput droplet digital PCR system for absolute quantitation of DNA copy number. Anal Chem 83: 8604-8610].

Kleinhofs et al. (1978) Induction and selection of specific gene mutations in Hordeum and Pisum. Mut. Res. 51: 29-35, 1978.

Kurowska et al—(2011) TILLING: a shortcut in functional genomics. *J Appl Genet. doi:*10.1007/s13353-011-0061-1

Lu et al. (2017) Genome-wide Targeted Mutagenesis in Rice Using the CRISPR/Cas9 system. Mol Plant. 2017 Sep. 12; 10(9):1242-1245.

Nazarenko et al. (1997) A closed tube format for amplification and detection of DNA based on energy transfer. Nucl. Acids Res. 1997, 25: 2516-2521

Rédei G P and Koncz C (1992). Classical mutagenesis. In: Koncz C et al. (eds.): Methods in *Arabidopsis* research, Chapter 2

Szurman-Zubrzycka et al. (2018) HorTILLUS-A Rich and Renewable Source of Induced Mutations for Forward/Reverse Genetics and Pre-breeding Programs in Barley (*Hordeum vulgare* L.). Front Plant Sci. 2018 Feb. 21; 9:216.

Tiessen et al. (2012) Mathematical modeling and comparison of protein size distribution in different plant, animal, fungal and microbial species reveals a negative correlation between protein size and protein number, thus providing insight into the evolution of proteomes. BMC Res Notes. doi:10.118611756-0500-5-85

Tsai et al. (2013) Production of a high-efficiency TILLING population through polyploidization. *Plant Physiol. doi:* 10.1104/pp. 112.213256

Tyagi et al. (1998) Multicolor molecular beacons for allele discrimination. Nature Biotechnology 16:49-53

Whitcombe et al. (1999) Detection of PCR products using selfprobing amplicons and fluorescence. Nature Biotechnol. 1999, August 17(8): 804-7.

U.S. Pat. No. 6,326,145
U.S. Pat. No. 7,838,053
WO 2018/001884

---

The invention claimed is:

1. A method for identifying a mutant plant of a predefined species carrying one or more mutation(s) in nucleotide(s) of interest [NOI(s)], in a predetermined target sequence, said method comprising:
   a) Providing Np regenerative parts of a parent plant of said species, wherein Np is the Number of regenerative parts to be mutagenized, and
      wherein Np is an integer of at least 5,000; and wherein Np further is in the range of 0.7×ONp to 1.3×ONp, wherein ONp is the Optimal Number of regenerative parts to be mutagenized and ONp=((OLS×100)/Hr)/GECN
      where Hr is the expected average harvest rate of said plant species after
      mutagenesis in %; and OLS is optimal library size, wherein OLS=log (1−PS/100)/log (1−(1−(1−(Mf×n)
      where PS is the probability of success in %, Mf is the mutation frequency, and
      n is the number of mutations screened for;
   b) subjecting said regenerative parts to a step of random mutagenesis, leading to a mutagenesis frequency of Mf, thereby generating a pool of regenerative parts of generation M0 representing a plurality of genotypes;
   c) growing said regenerative parts of generation M0 into mature plants of generation M1 and obtaining regenerative parts of generation M1 from said mature plants;
   d) optionally repeating the previous step X times to obtain plants of generation M (1+X) comprising regenerative parts of generation M (1+X);
   e) dividing regenerative parts of a plurality of generation M1 or M (1+X) plants into sub-pools, each sub-pool comprising regenerative parts representing a plurality of genotypes, wherein all regenerative parts from one given mature plant are placed in the same sub-pool;
   f) preparing DNA samples from each sub-pool;
   g) identifying sub-pool(s) comprising DNA comprising the mutation(s) using sensitive detection means; and
   h) identifying regenerative parts within said sub-pool comprising said mutation, thereby identifying said mutant plant,
      wherein a low rate of mutagenesis in diploid plants is that an average at least 99.8% of all genes are free of non-synonymous mutations and in plants of higher ploidy that an average of at least 98.0% of all genes are free of non-synonymous mutations in a regenerative part of generation M1.

2. The method according to claim 1, wherein the rate of mutagenesis is at the most 1 mutation every 1000 genes.

3. The method according to claim 1, wherein said mutagenesis leads to at the most 25 non-synonymous mutations in coding regions, in plants of generation M1.

4. The method according to claim 1, wherein the mutagenesis is an irradiation-induced mutagenesis or a chemical mutagenesis performed with a mutagenizing chemical.

5. The method according to claim 1, wherein at least 5,000 regenerative parts are obtained in step c).

6. The method according to claim 1, wherein the plant is a crop plant or a flowering plant.

7. The method according to claim 1, wherein step e) is performed by a method comprising
   i. determining the optimal size of the sub-pool, wherein the maximum sub-pool size (SPm)

$$SPm = \frac{Y}{GECN}$$

and
   ii. dividing said regenerative parts into sub-pools, wherein each sub-pool comprises regenerative parts from a number of mature plants, said number being in the range of 0.5×SPm to 1.1×SPm, wherein all regenerative parts from one given mature plant are placed in the same sub-pool;
wherein the detection sensitivity of the sensitive detection means is 1 in Y, and wherein the plants have a genetically effective cell number GECN.

8. The method according to claim 1, wherein step f) comprises:
   dividing each sub-pool into fractions; and
   preparing DNA samples of an entire fraction of each sub-pool.

9. The method according to claim 1, wherein the plant species has an average number of regenerative parts per plant of $RP_p$, and a genetically effective cell number of GECN, and wherein step f) comprises
   i. randomly dividing each sub-pool into fractions, wherein a first fraction comprises in the range of from 100% to 500% of (GECN/RP$_p$) of the regenerative parts of the sub-pool; and wherein said first fraction comprises at the most 50% of said regenerative parts; and ii. preparing DNA samples of the entire first fraction of each sub-pool.

10. The method according to claim 1, wherein step f) is performed by dividing each sub-pool into at least 2 fractions, and preparing DNA samples from an entire fraction of each sub-pool, and/or wherein step f) comprises obtaining a fraction comprising in the range of 10 to 50% of regenerative parts of each sub-pool and preparing DNA samples from the entire fractions of each sub-pool, and/or wherein step g) for each sub-pool comprises:
performing one or more PCR amplifications, comprising the DNA sample from said fraction of the sub-pool, one or more set(s) of primers each set flanking the target sequence and PCR reagents, thereby amplifying the target sequence(s); and
detecting PCR amplification product(s) comprising the target sequence(s) comprising the one or more mutation(s) in the NOI(s).

11. The method according to claim 1, wherein the method comprises a step of reproduction of the plants, or regenerative parts thereof, within the pool, and wherein said step of reproducing may be performed simultaneously with, or subsequent to, step e) of dividing the plants into sub-pools and/or wherein the regenerative parts of step e) are of generation M2.

12. The method according to claim 1, wherein step h) comprises:
Providing a sub-pool comprising a plurality of regenerative parts of a plant, wherein said sub-pool comprises regenerative parts comprising one or several mutation(s) of the NOI(s);
Dividing the regenerative parts of said sub-pool into secondary sub-pools;
Obtaining a sample from each regenerative part of the secondary sub-pools—in a manner leaving the regenerative parts sufficiently intact to develop into a plant—and combining all samples from all regenerative parts of each secondary sub-pool;
Preparing a DNA sample from said combined samples; and
Identifying secondary sub-pool(s) comprising DNA comprising the mutation(s).

13. The method according to claim 12, further comprising:
Providing the identified secondary sub-pool comprising regenerative parts comprising the mutation in the NOI, wherein the regenerative parts are seeds;
Cultivating all seeds within said secondary sub-pool to allow germination, and optionally develop plants from each seed;
Obtaining a sample from each germinated seed;
Testing said sample for the presence of said mutation in the NOI, thereby identifying a plant carrying the mutation in the NOI; and
Optionally growing said plant to maturity.

14. The method according to claim 13, wherein the method further comprises the following steps performed after step f):
Obtaining a fraction of each DNA sample from each sub-pool;
Combining a plurality of fractions into super-pools, thereby obtaining DNA super-pools comprising DNA samples from a plurality of sub-pools, wherein DNA from each sub-pool is only present in one super-pool;
Performing a plurality of PCR amplifications, each comprising a DNA sample super-pool, wherein each PCR amplification comprises a plurality of compartmentalised PCR amplifications, each comprising part of said DNA sample, one or more set(s) of primers each set flanking a target sequence and PCR reagents, thereby amplifying the target sequence(s); and
Detecting PCR amplification product(s) comprising one or more target sequence(s) comprising the mutation(s) in the NOI(s), thereby identifying super-pool(s) comprising said mutation.

15. The method according to claim 1, wherein the DNA samples of step f) are gDNA samples or cDNA samples obtained from mRNA samples.

16. The method according to claim 1, wherein the regenerative part is a seed.

17. The method according to claim 1, wherein at least 100,000 regenerative parts are obtained in step c).

18. The method according to claim 14, wherein the PCR amplifications are performed only on samples of DNA from sub-pool(s) comprising one of the mutation(s).

* * * * *